United States Patent
Murata et al.

[11] Patent Number: 6,159,902
[45] Date of Patent: Dec. 12, 2000

[54] HERBICIDES

[75] Inventors: Tetsuya Murata; Hideshi Mukaida; Yoshie Yamada; Yukiko Oe; Norishige Toshima; Sachio Kudo; Kouichi Araki; Atsushi Go; Masahito Ito, all of Ibaraki-Ken, Japan; Virginia Smith, Ongar, United Kingdom; Thomas Yarwood, Ongar, United Kingdom; Michael Gingell, Ongar, United Kingdom; Lyn Jennens, Ongar, United Kingdom

[73] Assignees: Mitsubishi Chemical Corporation, Tokyo, Japan; Rhone-Poulenc Agriculture LTD, Ongar, United Kingdom

[21] Appl. No.: 09/095,109

[22] Filed: Jun. 10, 1998

[30] Foreign Application Priority Data

Jun. 10, 1997 [GB] United Kingdom .................... 9712029
Jun. 10, 1997 [GB] United Kingdom .................... 9712031
Jun. 10, 1997 [GB] United Kingdom .................... 9712033
Jun. 10, 1997 [GP] Guadeloupe ........................... 9712032

[51] Int. Cl.⁷ .......................... A01N 43/86; C07D 265/06
[52] U.S. Cl. .............................................. 504/223; 544/97
[58] Field of Search ................................ 544/97; 504/223

[56] References Cited

U.S. PATENT DOCUMENTS 5,436,224 7/1995 Hamatani et al. ...................... 504/223
6,046,135 4/2000 Cramp et al. ........................... 504/223

FOREIGN PATENT DOCUMENTS

93/15064 8/1993 WIPO .
94/13665 6/1994 WIPO .
95/10510 4/1995 WIPO .
95/18113 7/1995 WIPO .
97/00865 1/1997 WIPO .
97/21688 6/1997 WIPO .
97/40041 10/1997 WIPO .

OTHER PUBLICATIONS

R.C. Larock, *Comprehensive Organic Transformations*, "A Guide to Functional Group Preparations," p. 838 (1989).

*Primary Examiner*—Richard L. Raymond
*Attorney, Agent, or Firm*—Burns, Doane, Swecker & Mathis, L.L.P.

[57] ABSTRACT

The invention relates to 1,3-oxazin-4-one derivatives of formula (I):

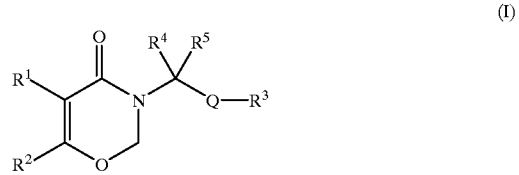

and to their use as herbicides.

31 Claims, No Drawings

HERBICIDES

CROSS-REFERENCE TO PRIORITY APPLICATIONS

This application claims priority under 35 U.S.C. §119 of United Kingdom Patent Application Nos. 97 12033.1, 97 12032.3, 97 12031.5 and 97 12029.9, all filed Jun. 10, 1997, all expressly incorporated by reference herein in their entireties and relied upon.

This invention relates to novel 1,3-oxazin-4-one derivatives, compositions containing them, processes for their preparation, and their use as herbicides.

Certain types of 1,3-oxazin-4-one derivatives, such as 2,3-dihydro-6-methyl-3-(1-methyl-1-phenylethyl)-5-phenyl-4H-1,3-oxazin-4-one, and their herbicidal activities are disclosed in for example International Patent Publication No. WO 93/15064. However, the compounds described in the above-mentioned publication do not have a ketone functionality in the group attached to the nitrogen atom at the 3-position of the 1,3-oxazine ring.

According to the present invention, there are provided 1,3-oxazin-4-one derivatives of formula I:

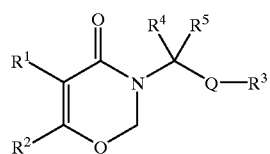

(I)

wherein:

$R^1$ represents:

—$CH_2R^6$; or phenyl optionally substituted by from one to five groups which may be the same or different selected from halogen, hydroxy, lower alkyl, lower haloalkyl, lower alkoxy, lower haloalkoxy, —$S(O)_mR^7$, —$CO_2R_7$, —$COR^7$, cyano, nitro, —$O(CH_2)_nCO_2R^7$, —$OR^6$, —$CH_2OR^7$, —$CH_2S(O)_pR^7$, —$CH_2N(R^7)SO_2R^{7a}$, —$CH_2CN$, —$CH_2P(=O)(OR^7)(OR^{7a})$, —$CH_2P(=O)(OR^7)R^{7a}$, lower alkenyl, lower haloalkenyl, $R^6$, $R^8$, $NR^9R^{10}$ and $NHCOR^7$; or a five to seven membered heteroaromatic ring having from one to four ring heteroatoms which may be the same or different selected from nitrogen, oxygen and sulphur (for example thienyl), said ring being optionally substituted by from one to four groups which may be the same or different selected from halogen, hydroxy, lower alkyl, lower haloalkyl, lower alkoxy, lower haloalkoxy, —$S(O)_mR^7$, —$CO_2R^7$, —$COR^7$, cyano, nitro, —$O(CH_2)_nCO_2R^7$ and phenoxy; or a straight- or branched-chain optionally halogenated alkyl, alkenyl or alkynyl group containing up to ten carbon atoms;

$R^4$ and $R^5$ independently represent lower alkyl;

Q represents —C(=O)— or —$C(OR^{14})(OR^{14a})$— wherein $R^{14}$ and $R^{14a}$ represent lower alkyl or the group —$C(OR^{14})(OR^{14a})$— represents a five or six membered cyclic ketal, namely a 1,3-dioxolane or 1,3-dioxane ring of formula —$C(OR^{14b})(OR^{14c})$— wherein $R^{14b}$ and $R^{14c}$ together represent a C2 or C3 alkylene chain which is optionally substituted by lower alkyl;

$R^6$ represents phenyl optionally substituted by one or more groups which may be the same or different selected from halogen, lower alkyl, lower haloalkyl, lower alkoxy, lower haloalkoxy, —$S(O)_mR^7$, cyano and nitro;

$R^7$ and $R^{7a}$ independently represent lower alkyl or lower haloalkyl;

$R^8$ represents a five to seven membered heteroaromatic ring having from one to four ring heteroatoms which may be the same or different selected from nitrogen, oxygen and sulphur, said ring being optionally substituted by from one to four groups which may be the same or different selected from halogen, hydroxy, lower alkyl, lower haloalkyl, lower alkoxy, lower haloalkoxy, and —$S(O)_mR^7$;

$R^9$ and $R^{10}$ represent hydrogen, lower alkyl or lower haloalkyl; and i):

$R^2$ represents:

a hydrogen atom; or a straight- or branched-chain optionally halogenated alkyl, alkenyl or alkynyl group having up to ten carbon atoms;

a straight- or branched-chain optionally halogenated alkyl group containing from one to six carbon atoms which is substituted by a group $R^{11}$;

or a group selected from cyano, —CHO, —$COR^7$, —$CO_2H$, —$CO_2R^7$, —$COSR^7$, —$CONR^9R^{10}$, —CH=NOH, —CH=$NOR^7$, —CH=$NOCOR^7$, —CH=$NNR^9R^{10}$, —$CONHR^6$, —$CONR^6R^7$, —$CO_2R^6$, oxiranyl and $R^{12}$;

and $R^3$ represents:

cycloalkyl containing from three to eight carbon atoms or cycloalkenyl containing four to eight carbon atoms, wherein the ring systems are substituted by a group E which is selected from $CO_2H$, $CO_2R^7$, lower alkenyl, lower haloalkenyl, $R^6$, $NR^9R^{10}$, lower alkoxy, lower haloalkoxy, $S(O)_mR^7$, $COR^7$, $COR^6$, $CH_2COR^6$, $COCH_2R^6$, $CO_2CH_2R^6$, $S(O)_qR^6$, CN, $S(O)_qCH_2R^6$, $S(O)_qR^{15}$, $CH_2OR^7$, CHO, $COR^{12}$, $NO_2$, $CONHR^6$, $CONR^6R^7$, $CH_2OH$, —$CH(OR^{14})(OR^{14a})$ (optionally the group —$CH(OR^{14})(OR^{14a})$ represents a five or six membered cyclic acetal optionally substituted by one or more $R^7$ groups), or one of the cycloalkyl carbon atoms forms part of a carbonyl group (optionally the above defined cycloalkyl or cycloalkenyl rings may contain in addition to E one or more halogen or $R^7$ groups), and preferably the substituent E is attached to the carbon atom by which the cycloalkyl or cycloalkenyl group is attached to Q; or represents cycloalkyl containing from five to seven carbon atoms or cycloalkenyl containing five or six carbon atoms, the ring systems of which are optionally substituted by one or more groups $R^{13}$, and wherein the ring systems are fused to a phenyl ring (for example indanyl) optionally substituted by from one to four groups which may be the same or different selected from halogen, lower alkyl, lower haloalkyl, lower alkoxy, lower haloalkoxy, —$S(O)_mR^7$, cyano or nitro (it is understood that for fused ring systems it is the cycloalkyl or cycloalkenyl ring which is linked to the group Q);

or:

$R^3$ represents lower alkyl or lower haloalkyl which are substituted by one or two $R^{13a}$ groups, optionally together with an $R^{14d}$ group; or lower alkenyl or lower haloalkenyl which are substituted by one or two $R^{13a}$ groups, optionally together with a group selected from $R^6$, $R^{15a}$ and $R^{15}$; or lower alkynyl substituted by a group $R^{13a}$ (preferably an $R^{13a}$ group in the above definitions is located on the carbon atom of $R^3$ which is alpha or beta to the group Q);

or:

$R^3$ represents a phenyl or naphthyl ring which is substituted by a group selected from:
—$OCOR^7$, $NR^9R^{10}$, $NHR^6$, —$CH_2NR^9R^{10}$, —$CONR^9R^{10}$, —$CONHR^6$, —$OSO_2R^7$, —$OSO_2R^6$, —$OCOR^6$, —$OCH_2COR^6$, —$OCH_2R^6$, —$S(O)_qR^6$, $R^6$, —$P(=O)(OR^7)(OR^{7a})$, —$P(=O)(OR^7)R^{7a}$, —$CH_2P(=O)(OR^7)(OR^{7a})$, —$CH_2P(=O)(OR^7)R^{7a}$, $CO_2R^6$, —$CH_2S(O)_nR^7$, —$CH_2S(O)_qR^6$, —$CH_2OR^7$, —$CH_2OR^6$, $CH_2OCOR^6$, $CH_2OSO_2R^6$ or lower alkenyl (optionally the phenyl or naphthyl rings may in addition be substituted by one or more halogen or $R^7$ groups);

or represents a phenyl ring optionally substituted by from one to five groups which may be the same or different selected from halogen, lower alkyl, lower haloalkyl, lower alkoxy, lower haloalkoxy, —$S(O)_mR^7$, CN and $NO_2$, and which is fused to a second five or six membered cycloalkyl or cycloalkenyl ring, or to a saturated five or six membered heterocyclic ring (for example to give a 1,3-benzodioxole or 1,4-benzodioxane ring) which contains one to three heteroatoms which may be the same or different selected from nitrogen, oxygen and sulphur, said ring systems being optionally substituted by one or more groups $R^{13}$ or optionally one of the carbon atoms in the cycloalkyl, cycloalkenyl or saturated five or six membered heterocyclic ring may form a carbonyl group (it is understood that for fused ring systems it is the phenyl ring which is linked to the group Q); or represents a phenanthrene or anthracene ring optionally substituted by one or more groups selected from halogen, lower alkyl, lower haloalkyl, lower alkoxy, lower haloalkoxy, —$S(O)_mR^7$, CN and $NO_2$;

or:

$R^3$ represents a bicyclo-alkane, a bicyclo-alkene, a spiro-alkane or a spiro-alkene, the ring systems of which contain from six to nine carbon atoms and are optionally substituted by one or more lower alkyl groups; or $R^3$ represents optionally halogenated lower alkyl substituted by a cycloalkyl ring containing from three to six carbon atoms or by a cycloalkenyl ring containing five or six carbon atoms, the ring systems of which are substituted by a group selected from lower alkyl, lower haloalkyl, halogen, —$S(O)_mR^7$, CN, $NO_2$ and —$CO_2R^7$; or $R^3$ represents —$CH(OH)R^{18}$, —$CH(OH)R^{18a}$, —$COR^{18}$ or —$COR^{18a}$; or $R^3$ represents lower alkyl substituted by —$S(O)_u(CH_2)_vR^{18a}$, —$S(O)_uR^{20}$, —$OR^{15}$, —$O(CH_2)_wR^{18}$, —$O(CH_2)_wR^{18a}$, —$OR^{20}$, —$NR^{21}R^{22}$, or —$P(=O)(OR^9)R^{23}$; or $R^3$ represents cycloalkyl containing from three to eight carbon atoms substituted by an exocyclic optionally halogenated alkylidene group which contains from one to six carbon atoms (optionally the cycloalkyl ring may be substituted by one or more lower alkyl groups: optionally when the alkylidene group represents methylidene, both vacant positions of the exocyclic carbon atom may be linked by an alkylene chain which together with the methylidene carbon atom forms a three to six membered cycloalkyl ring);

or ii):

$R^2$ represents:

lower alkyl or lower haloalkyl which are substituted by one or two groups $R^{11a}$; or represents a group selected from $R^{12}$, —$CONHR^6$, —$CONR^6R^7$ and $CO_2R^6$;

and $R^3$ represents —$(CH_2)_r$-(phenyl or naphthyl optionally substituted by from one to five groups which may be the same or different selected from halogen, hydroxy, lower alkyl, lower haloalkyl, lower alkoxy, lower haloalkoxy, —$S(O)_mR^7$, —$CO_2R^7$, —$COR^7$, CN, $NO_2$, —$O(CH_2)_nCO_2R^7$, phenoxy and —$SF_5$); or —$(CH_2)_s$-(five to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system, the monocyclic ring or either ring in the bicyclic system being optionally substituted by from one to four groups which may be the same or different selected from halogen, OH, lower alkyl, lower haloalkyl, lower alkoxy, lower haloalkoxy, —$S(O)_mR^7$, —$CO_2R^7$, —$COR^7$, CN, $NO_2$, —$O(CH_2)_nCO_2R^7$ and phenoxy); or a straight- or branched-chain optionally halogenated alkyl, alkenyl or alkynyl group containing up to ten carbon atoms; or a straight- or branched-chain optionally halogenated alkyl, alkenyl or alkynyl group containing up to ten carbon atoms which is substituted by cycloalkyl containing from three to six carbon atoms; or cycloalkyl containing from three to six carbon atoms or cycloalkenyl containing five or six carbon atoms, the ring systems of which are optionally substituted by a group $R^7$ or one or more halogen atoms which may be the same or different;

$R^{11}$ represents —OH, —$OR^7$, —$OCOR^7$, —$S(O)_mR^7$, —$NR^9R^{10}$, azide, —$CONR^9R^{10}$, —$CONHR^6$, —$CONR^6R^7$, —$OR^6$, —$OSO_2R^7$, —$OSO_2R^6$, —$OCOR^6$, —$OCH_2COR^6$, —$S(O)_qR^6$, $R^6$, $R^{12}$, —$P(=O)(OR^7)(OR^{7a})$, —$P(=O)(OR^7)R^{7a}$, —$CO_2H$, —$CO_2R^7$, —$CO_2R^6$, CN, $NO_2$, CHO, $COR^7$, $COSR^7$, —$S(O)_rR^{15}$ or —$CO_2R^{15}$;

$R^{11a}$ represents —$CONR^9R^{10}$, —$CONHR^6$, —$CONR^6R^7$, —$OR^6$, —$OSO_2R^7$, —$OSO_2R^6$, —$OCOR^6$, —$OCH_2COR^6$, —$S(O)_qR^6$, $R^6$, $R^{12}$, —$P(=O)(OR^7)(OR^{7a})$, —$P(=O)(OR^7)R^{7a}$, —$CO_2H$, —$CO_2R^7$, —$CO_2R^6$, CHO, $COR^7$, $COR^6$, $COSR^7$, —$S(O)_rR^{15}$ or —$CO_2R^{15}$;

$R^{12}$ represents cycloalkyl containing from three to seven carbon atoms or cycloalkenyl containing five or six carbon atoms, wherein the ring systems are optionally substituted by one or more groups $R^{13}$;

$R^{13}$ represents halogen, lower alkyl or lower haloalkyl;

$R^{13a}$ represents —OH, —$OR^7$, —$S(O)_mR^7$, —$S(O)_qR^6$, —$CO_2R^7$, —$CO_2CH_2R^6$, CN, $NO_2$, CHO, $COR^7$, $COR^6$, $COCH_2R^6$, —$CO_2H$, $CONR^9R^{10}$, —$S(O)_qCH_2R^6$, —$S(O)_rR^{15}$ or a five or six membered cyclic acetal group optionally substituted by one or more $R^7$ groups;

$R^{14d}$ represents $R^6$, lower alkynyl, or a three to six membered cycloalkyl ring optionally substituted by one or more $R^7$ or halogen groups;

$R^{15}$ represents cycloalkyl containing from three to seven carbon atoms optionally substituted by one or more groups $R^{13}$;

$R^{15a}$ represents a thienyl or furyl ring optionally substituted by one or more groups $R^{13}$;

$R^{18}$ represents phenyl optionally substituted by from one to five $R^{19}$ groups which may be the same or different;

$R^{18a}$ represents a naphthyl ring or a five to seven membered heteroaromatic ring having from one to four ring heteroatoms which may be the same or different selected from nitrogen, oxygen and sulphur, the ring systems of which are optionally substituted by from one to four $R^{19}$ groups which may be the same or different;

$R^{19}$ represents halogen, lower alkyl, lower haloalkyl, lower alkoxy, lower haloalkoxy, $-S(O)_mR^7$, $NO_2$ or -phenoxy;

$R^{20}$ represents lower alkenyl, lower haloalkenyl, lower alkynyl or lower haloalkynyl;

$R^{21}$ and $R^{22}$ independently represent hydrogen, $R^7$, $R^{15}$, $R^{18}$, $R^{18a}$ or $R^{20}$;

$R^{23}$ represents hydroxy, lower alkyl, lower haloalkyl, lower alkoxy or lower haloalkoxy;

m, p, q, r, t and u represent zero, one or two;

n represents one or two;

s, v and w represent zero or one;

and agriculturally acceptable salts thereof, which possess valuable herbicidal properties.

By the term "agriculturally acceptable salts" is meant salts, the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, e.g. formed by compounds of formula I containing an amino group, include salts with inorganic acids, for example hydrochlorides, sulphates, phosphates and nitrates and salts with organic acids for example acetic acid. The salts may be prepared by known methods.

In certain cases the groups $R^1$ to $R^{23}$ may give rise to stereoisomers and geometric isomers. All such forms and mixtures thereof are embraced by the present invention.

In the description unless otherwise specified the following terms are generally defined thus:

'lower alky' means a straight- or branched-chain alkyl group having one to six carbon atoms;

'lower haloalkyl' means a straight- or branched-chain alkyl group having one to six carbon atoms, substituted by one or more halogens;

'lower alkoxy' means a straight- or branched-chain alkoxy group having one to six carbon atoms;

'lower haloalkoxy' means a straight- or branched-chain alkoxy group having one to six carbon atoms, substituted by one or more halogens;

'lower alkenyl' means a straight- or branched-chain alkenyl group having two to six carbon atoms;

'lower haloalkenyl' means a straight- or branched-chain alkenyl group having two to six carbon atoms, substituted by one or more halogens;

'lower alkynyl' means a straight- or branched-chain alkynyl group having two to six carbon atoms;

'halogen' means a fluorine, chlorine, bromine or iodine atom.

The compounds are particularly useful in the control of weeds found in rice for example Echinochloa species.

The invention also provides compounds of formula (Ia) which conform to formula (I) wherein:

$R^2$ represents:

a hydrogen atom; or a straight- or branched-chain optionally halogenated alkyl, alkenyl or alkynyl group having up to ten carbon atoms;

a straight- or branched-chain optionally halogenated alkyl group containing from one to six carbon atoms which is substituted by a group $R^{11}$;

or a group selected from cyano, —CHO, —COR$^7$, —CO$_2$H, —CO$_2$R$^7$, —COSR$^7$, —CONR$^9$R$^{10}$, —CH=NOH, —CH=NOR$^7$, —CH=NOCOR$^7$, —CH=NNR$^9$R$^{10}$, —CONHR$^6$, —CONR$^6$R$^7$, —CO$_2$R$^6$, oxiranyl and $R^{12}$; and $R^3$ represents:

cycloalkyl containing from three to eight carbon atoms or cycloalkenyl containing four to eight carbon atoms, wherein the ring systems are substituted by a group E which is selected from CO$_2$H, CO$_2$R$^7$, lower alkenyl, lower haloalkenyl, R$^6$, NR$^9$R$^{10}$, lower alkoxy, lower haloalkoxy, S(O)$_m$R$^7$, COR$^7$, COR$^6$, CH$_2$COR$^6$, COCH$_2$R$^6$, CO$_2$CH$_2$R$^6$, S(O)$_q$R$^6$, CN, S(O)$_q$CH$_2$R$^6$, S(O)$_r$R$^{15}$, CH$_2$OR$^7$, CHO, COR$^{12}$, NO$_2$, CONHR$^6$, CONR$^6$R$^7$, CH$_2$OH, —CH(OR$^{14}$)(OR$^{14a}$) (optionally the group —CH(OR$^{14}$)(OR$^{14a}$) represents a five or six membered cyclic acetal optionally substituted by one or more $R^7$ groups), or one of the cycloalkyl carbon atoms forms part of a carbonyl group (optionally the above defined cycloalkyl or cycloalkenyl rings may contain in addition to E one or more halogen or $R^7$ groups), and preferably the substituent E is attached to the carbon atom by which the cycloalkyl or cycloalkenyl group is attached to Q; or represents cycloalkyl containing from five to seven carbon atoms or cycloalkenyl containing five or six carbon atoms, the ring systems of which are optionally substituted by one or more groups $R^{13}$, and wherein the ring systems are fused to a phenyl ring (for example indanyl) optionally substituted by from one to four groups which may be the same or different selected from halogen, lower alkyl, lower haloalkyl, lower alkoxy, lower haloalkoxy, —S(O)$_m$R$^7$, cyano or nitro (it is understood that for fused ring systems it is the cycloalkyl or cycloalkenyl ring which is linked to the group Q);

and compounds of formula (Ib) which conform to formula (I) wherein $R^2$ is as defined above for formula (Ia) and $R^3$ represents lower alkyl or lower haloalkyl which are substituted by one or two $R^{13a}$ groups, optionally together with an $R^{14d}$ group; or lower alkenyl or lower haloalkenyl which are substituted by one or two $R^{13a}$ groups, optionally together with a group selected from $R^6$, $R^{15a}$ and $R^{15}$; or lower alkynyl substituted by a group $R^{13a}$ (preferably an $R^{13a}$ group in the above definitions is located on the carbon atom of $R^3$ which is alpha or beta to the group Q);

and compounds of formula (Ic) which conform to formula (I) wherein $R^2$ is as defined above for formula (Ia) and R$^3$ represents a phenyl or naphthyl ring which is substituted by a group selected from:
—OCOR$^7$, NR$^9$R$^{10}$, NHR$^6$, —CH$_2$NR$^9$R$^{10}$, —CONR$^9$R$^{10}$, —CONHR$^6$, —OSO$_2$R$^7$, —OSO$_2$R$^6$, —OCOR$^6$, —OCH$_2$COR$^6$, —OCH$_2$R$^6$, —S(O)$_q$R$^6$, R$^6$, —P(=O)(OR$^7$)(OR$^{7a}$), —P(=O)(OR$^7$)R$^{7a}$, —CH$_2$P(=O)(OR$^7$)(OR$^{7a}$), —CH$_2$P(=O)(OR$^7$)R$^{7a}$, —CO$_2$R$^6$, —CH$_2$S(O)$_n$R$^7$, —CH$_2$S(O)$_q$R$^6$, —CH$_2$OR$^7$, —CH$_2$OR$^6$, —CH$_2$OCOR$^6$, CH$_2$OSO$_2$R$^6$ or lower alkenyl (optionally the phenyl or naphthyl rings may in addition be substituted by one or more halogen or R$^7$ groups);

or represents a phenyl ring optionally substituted by from one to five groups which may be the same or different selected from halogen, lower alkyl, lower haloalkyl, lower alkoxy, lower haloalkoxy, —S(O)$_m$R$^7$, CN and NO$_2$, and which is fused to a second five or six membered cycloalkyl or cycloalkenyl ring, or to a saturated five or six membered heterocyclic ring (for example to give a 1,3-benzodioxole or 1,4-benzodioxane ring) which contains one to three heteroatoms which may be the same or different selected from nitrogen, oxygen and sulphur, said ring systems being optionally substituted by one or more groups R$^{13}$ or optionally one of the carbon atoms in the cycloalkyl, cycloalkenyl or saturated five or six membered heterocyclic ring may form a carbonyl group (it is understood that for fused ring systems it is the phenyl ring which is linked to the group Q); or represents a phenanthrene or anthracene ring optionally substituted by one or more groups selected from halogen, lower alkyl, lower haloalkyl, lower alkoxy, lower haloalkoxy, —S(O)$_m$R$^7$, CN and NO$_2$;

and compounds of formula (Id) which conform to formula (I) wherein R$^2$ represents lower alkyl or lower haloalkyl which are substituted by one or two groups R$^{11a}$; or represents a group selected from R$^{12}$, —CONHR$^6$, —CONR$^6$R$^7$ and CO$_2$R$^6$;

and

R$^3$ represents —(CH$_2$)$_r$-(phenyl or naphthyl optionally substituted by from one to five groups which may be the same or different selected from halogen, hydroxy, lower alkyl, lower haloalkyl, lower alkoxy, lower haloalkoxy, —S(O)$_m$R$^7$, —CO$_2$R$^7$, —COR$^7$, CN, NO$_2$, —O(CH$_2$)$_n$CO$_2$R$^7$, phenoxy and —SF$_5$); or —(CH$_2$)$_s$-(five to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system, the monocyclic ring or either ring in the bicyclic system being optionally substituted by from one to four groups which may be the same or different selected from halogen, OH, lower alkyl, lower haloalkyl, lower alkoxy, lower haloalkoxy, —S(O)mR$^7$, —CO$_2$R$^7$, —COR$^7$, CN, NO$_2$, —O(CH$_2$)$_n$CO$_2$R$^7$ and phenoxy); or a straight- or branched-chain optionally halogenated alkyl, alkenyl or alkynyl group containing up to ten carbon atoms; or a straight- or branched-chain optionally halogenated alkyl, alkenyl or alkynyl group containing up to ten carbon atoms which is substituted by cycloalkyl containing from three to six carbon atoms; or cycloalkyl containing from three to six carbon atoms or cycloalkenyl containing five or six carbon atoms, the ring systems of which are optionally substituted by a group R$^7$ or one or more halogen atoms which may be the same or different;

and the other various symbols are as defined above for formula (I).

In the description that follows a number of preferred classes (because of their herbicidal properties) of compounds of formula I above are disclosed.

Compounds of formula (I) above in which R$^1$ represents phenyl or thienyl optionally substituted by one or more groups selected from halogen, lower alkyl and lower haloalkyl are preferred. Most preferably R$^1$ represents phenyl.

A further preferred class of compounds of formula (I) above are those wherein R$^2$ represents a straight- or branched-chain optionally halogenated alkyl group having from one to six carbon atoms, most preferably methyl.

Compounds of formula (I) above in which R$^4$ and R$^5$ each represent methyl are especially preferred.

Compounds of formula (I) above in which Q represents —C(=O)— are especially preferred because of their herbicidal activity.

Compounds of formula (Ia) above in which R$^3$ is substituted cyclopentyl are preferred.

Compounds of formula (I) above in which R$^3$ represents bicyclo[2.2.1]heptane, bicyclo[2.2.1]heptene, bicyclo[3.1.0]hexane, bicyclo[4.1.0]heptane, spiro[2.4]heptane, spiro[2.4]heptene; or lower alkyl substituted by a cycloalkyl ring which is substituted by lower alkyl or methylene; or cycloalkyl containing from three to six carbon atoms substituted by an exocyclic alkylidene group which contains from one to six carbon atoms are also preferred.

A preferred sub-class of compounds of formula (Ia) are those having the general formula (Ie):

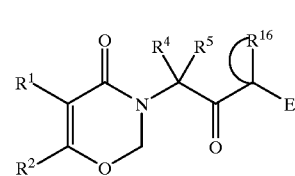

(Ie)

wherein R$^1$, R$^2$, R$^4$ and R$^5$ and E are as defined above; and

R$^{16}$ represents a C2–C7-alkylene or C3–C7 alkenylene group which are optionally substituted by one or more halogen or R$^7$ groups.

A particularly preferred class of compounds of formula (Ie) above are those wherein:
R$^1$ represents phenyl or thienyl optionally substituted by halogen or methyl;
R$^2$ represents methyl or fluoromethyl; and
R$^4$ and R$^5$ each represent methyl.

A further particularly preferred class of compounds of formula (Ie) above are those wherein:
R$^1$ represents phenyl or thienyl optionally substituted by halogen or methyl;
R$^2$ represents methyl or fluoromethyl;
E represents —CO$_2$R$^7$, —CH$_2$COR$^6$, —CN, —S(O)$_q$R$^6$, —S(O)$_m$R$^7$, —COR$^7$, —NO$_2$, —CO$_2$CH$_2$R$^6$;
R$^4$ and R$^5$ each represent methyl; and
R$^{16}$ represents C2–C7 alkylene, C3–C7 alkenylene, or an indanyl group (which groups optionally contain one or more additional halogen or R$^7$ groups).

A further particularly preferred class of compounds of formula (Ie) above are those wherein:

$R^1$ represents:
  phenyl or thienyl optionally substituted by halogen or methyl;
$R^2$, $R^4$ and $R^5$ each represent methyl;
$R^{16}$ together with the carbon atom to which it is attached represents cyclopentyl; and
E represents $CO_2R^7$.

A further preferred class of compounds of formula (Ib) above are those in which $R^3$ represents lower alkyl or lower haloalkyl which are substituted by an $R_{13a}$ group, optionally together with an $R_{14d}$ group; or
  lower alkenyl or lower haloalkenyl which are substituted by one or two $R^{13a}$ groups, optionally together with a group selected from $R^6$, $R^{15a}$ and $R^{15}$; and wherein an $R^{13a}$ group is located on the carbon atom of $R^3$ which is alpha or beta to the group Q.

A particularly preferred class of compounds of formula (Ib) above are those wherein:

$R^1$ represents phenyl or thienyl optionally substituted by halogen;
$R^2$ represents methyl or fluoromethyl;
$R^3$ represents lower alkyl or lower haloalkyl substituted by an $R^{13a}$ group, optionally together with an $R^{14d}$ group; or represents lower alkenyl substituted by an $R^{13a}$ group; and wherein the $R^{13a}$ group is located on the carbon atom of $R^3$ adjacent to the Q group;
$R^{13a}$ represents $CO_2R^7$, $CO_2CH_2R^6$, CN, $NO_2$, $COR^7$, $COR^6$, $-S(O)_mR^7$, $-S(O)_qR^6$;
$R^{14d}$ represents $OR^7$, $R^6$, lower alkynyl or a three membered cycloalkyl ring optionally substituted by one or more $R^7$ or halogen groups.
$R^4$ and $R^5$ each represent methyl; and
Q represents $-C(=O)-$.

A further particularly preferred class of compounds of formula (Ib) above are those wherein:

$R^1$ represents phenyl;
$R^2$, $R^4$ and $R^5$ each represent methyl;
Q represents $-C(=O)-$;
$R^3$ represents lower alkyl or lower haloalkyl substituted by an $R^{13a}$ group; or
  lower alkenyl substituted by a group $R^{13b}$, optionally together with a group selected from $R^6$, $R^{15a}$ and $R^{15}$;
$R^{13a}$ represents $CO_2R^7$, $COR^7$,OH or a five or six membered cyclic acetal group (i.e. a 1,3-dioxolane or 1,3-dioxane ring) which is optionally substituted by one or more $R^7$ groups;
$R^{13b}$ represents $CO_2R^7$; and wherein the groups $R^{13a}$ and $R^{13b}$ are located on the carbon atom of $R^3$ adjacent to the Q group.

Preferred compounds of formula (Ic) above are those in which $R^3$ represents a phenyl ring substituted by a group selected from $-OSO_2R^7$, $-OSO_2R^6$, $-OCOR^6$, $-OCH_2COR^6$, $-CH_2S(O)_qR^6$, $-CH_2OR^7$, $CH_2OCOR^6$, $CH_2OSO_2R^6$, $R^6$ and lower alkenyl (the phenyl ring may in addition be substituted by one or more halogen or $R^7$ groups); or
  a 1,3-benzodioxole or 1,4-benzodioxane ring optionally substituted by one or more halogen atoms; or a phenanthrene ring.

A particularly preferred class of compounds of formula (Ic) above are those wherein:

$R^1$ represents phenyl or thienyl optionally substituted by halogen;
$R^2$ represents lower alkyl, lower haloalkyl; or a methyl group substituted by a group $R^{11}$;
$R^4$ and $R^5$ each represent methyl;
$R^{11}$ represents $OR^7$ or $SO_2R^6$; and
Q represents $-C(=O)-$.

A further particularly preferred class of compounds of formula (Ic) above are those wherein:

$R^1$ represents phenyl or thienyl optionally substituted by halogen;
$R^2$ represents lower alkyl, lower haloalkyl; or a methyl group substituted by a group $R^{11}$;
$R^3$ represents a phenyl ring substituted by a group selected from $-OSO_2R^7$, $-OSO_2R^6$, $-OCOR^6$, $-OCH_2COR^6$, $-CH_2S(O)_qR^6$, $-CH_2OR^7$, $CH_2OCOR^6$, $CH_2OSO_2R^6$, $R^6$ and lower alkenyl (the phenyl ring may in addition be substituted by one or two halogen or $R^7$ groups); or an optionally halogenated 1,3-benzodioxole or 1,4-benzodioxane ring;
$R^4$ and $R^5$ each represent methyl;
$R^{11}$ represents $OR^7$ or $SO_2R^6$; and
Q represents $-C(=O)-$.

A further particularly preferred class of compounds of formula (Ic) above are those wherein:

$R^1$ represents phenyl;
$R^2$, $R^4$ and $R^5$ each represent methyl;
Q represents $-C(=O)-$;
$R^3$ represents a phenyl ring which is substituted by a group selected from lower alkenyl and phenyl optionally substituted by one or two halogen atoms (optionally the phenyl ring may in addition be substituted by one or two halogen atoms); or
  a 1,3-benzodioxole ring optionally substituted by one or more halogen atoms; or a phenanthrene ring.

A further preferred class of compounds of formula (Id) above are those wherein $R^2$ represents methyl substituted by a group $R^{11a}$ or is $-CH(CO_2R^7)_2$.

Compounds of formula (Id) above in which $R^3$ represents a phenyl ring substituted by one or more halogen, lower alkyl, lower haloalkyl, lower alkoxy, lower haloalkoxy or $SF_5$ groups; or cycloalkyl containing from three to six carbon atoms or cycloalkenyl containing five or six carbon atoms, the ring systems of which are optionally substituted by a group $R^7$ or one or more halogen atoms which may be the same or different are also preferred. Most preferably $R^3$ represents cyclopentyl.

A particularly preferred class of compounds of formula (Id) above are those wherein:

$R^1$ represents phenyl or thienyl optionally substituted by halogen or lower alkyl;
$R^2$ represents methyl substituted by one or two groups $R^{11a}$;
$R^3$ represents lower alkyl or cyclopentyl; or a phenyl ring substituted by one or two halogen lower alkyl or lower alkoxy groups;
$R^4$ and $R^5$ each represent methyl;
$R^{11a}$ represents $-CO_2R^{15}$, $-CO_2R^7$, $-CO_2H$, $R^6$, $-OSO_2R^7$, $-OSO_2R^6$, $-S(O)_qR^6$, $-COR^6$, $-OCH_2COR^6$ or $-COR^7$; and
Q represents $-C(=O)-$.

A further particularly preferred class of compounds of formula (Id) above are those wherein:

R$^1$ represents phenyl;

R$^2$ represents methyl substituted by one or two groups R$^{11}$;

R$^3$ represents a phenyl ring optionally substituted by one or two halogen atoms;

R$^4$ and R$^5$ each represent methyl;

R$^{11a}$ represents —CO$_2$R$^7$ or —CO$_2$H; and

Q represents —C(=O)—.

A further particularly preferred class of compounds of formula (I) above are those wherein:

R$^1$ represents phenyl;

R$^2$, R$^4$ and R$^5$ represent methyl;

Q represents —C(=O)—; and

R$^3$ represents bicyclo[2.2.1]heptane, bicyclo[2.2.1]heptene, bicyclo[3.1.0]hexane, bicyclo[4.1.0]heptane, spiro[2.4]heptane, spiro[2.4]heptene; or lower alkyl substituted by a cycloalkyl ring which is substituted by lower alkyl; or cycloalkyl containing from three to six carbon atoms substituted by an exocyclic methylene group (optionally the cycloalkyl ring may contain one or more lower alkyl groups).

Particularly important compounds of formula (I), in which the compound numbers are for reference purposes only, include the following:

ethyl 1-[2-(2,3-dihydro-6-methyl-4-oxo-5-phenyl-4H-1,3-oxazin-3-yl)-2-methylpropionyl]cyclopentylcarboxylate (Compound 1)

ethyl 1-[2-(2,3-dihydro-6-methyl-4-oxo-5-phenyl-4H-1,3-oxazin-3-yl)-2-methylpropionyl]cyclopent-3-enylcarboxylate (Compound 9)

methyl 1-[2-(2,3-dihydro-6-methyl-4-oxo-5-phenyl-4H-1,3-oxazin-3-yl)-2-methylpropionyl]cyclopentylcarboxylate (Compound 28)

benzyl 1-[2-(2,3-dihydro-6-methyl-4-oxo-5-phenyl-4H-1,3-oxazin-3-yl)-2-methylpropionyl]cyclopentylcarboxylate (Compound 44)

ethyl 2-bromo-4-(2,3-dihydro-6-methyl-4-oxo-5-phenyl-1,3-oxazin-3-yl)-4-methyl-3-oxo-pentanoate (Compound 190)

ethyl 2-chloro-4-(2,3-dihydro-6-methyl-4-oxo-5-phenyl-1,3-oxazin-3-yl)-4-methyl-3-oxo-pentanoate (Compound 191)

ethyl 2,2-difluoro-4-(2,3-dihydro-6-methyl-4-oxo-5-phenyl-1,3-oxazin-3-yl)-4-methyl-3-oxo-pentanoate (Compound 192)

5-(2,3-dihydro-6-methyl-4-oxo-5-phenyl-1,3-oxazin-3-yl)-5-methyl-2,4-hexanedione (Compound 193)

ethyl 4-methyl-4-(2,3-dihydro-6-methyl-4-oxo-5-phenyl-4H-1,3-oxazin-3-yl)-2-(4'-iodobutyl)-3-oxo-pentanoate (Compound 194)

ethyl 4-(2,3-dihydro-6-methyl-4-oxo-5-phenyl-4H-1,3-oxazin-3-yl)-2,4-dimethyl-3-oxo-pentanoate (Compound 195), ethyl 2-ethyl-4-(2,3-dihydro-6-methyl-4-oxo-5-phenyl-4H-1,3-oxazin-3-yl)-4-methyl-3-oxo-pentanoate (Compound 196)

ethyl 4-(2,3-dihydro-6-methyl-4-oxo-5-phenyl-4H-1,3-oxazin-3-yl)-2,2,4-trimethyl-3-oxo-pentanoate (Compound 197)

ethyl 2-ethyl-4-(2,3-dihydro-6-methyl-4-oxo-5-phenyl-4H-1,3-oxazin-3-yl)-2,4-dimethyl-3-oxo-pentanoate (Compound 198)

ethyl 2,2-diethyl-4-(2,3-dihydro-6-methyl-4-oxo-5-phenyl-4H-1,3-oxazin-3-yl)-4-methyl-3-oxo-pentanoate (Compound 199)

ethyl 4-(2,3-dihydro-6-methyl-4-oxo-5-phenyl-4H-1,3-oxazin-3-yl)-4-methyl-3-oxo-pentanoate (Compound 200)

methyl 4-(2,3-dihydro-6-methyl-4-oxo-5-phenyl-4H-1,3-oxazin-3-yl)-4-methyl-3-oxo-pentanoate (Compound 201)

t-butyl 4-(2,3-dihydro-6-methyl-4-oxo-5-phenyl-1,3-oxazin-3-yl)-4-methyl-3-oxo-pentanoate (Compound 202)

2-[4-(2,3-dihydro-6-methyl-4-oxo-5-phenyl-4H-1,3-oxazin-3-yl)-4-methylpentan-3-oyl]-2,5,5-trimethyl-1,3-dioxane (Compound 203)

2-[4-(2,3-dihydro-6-methyl-4-oxo-5-phenyl-4H-1,3-oxazin-3-yl)-4-methylpentan-3-oyl]-1,3-dioxolane (Compound 204)

6-(2,3-dihydro-6-methyl-4-oxo-5-phenyl-4H-1,3-oxazin-3-yl)-6-methylheptan-2,5-dione (Compound 205)

ethyl 4-methyl-4-(2,3-dihydro-6-methyl-5-phenyl-4-oxo-4H-1,3-oxazin-3-yl)-3-oxo-pentanoate (Compound 206)

ethyl 2-(cyclohexylmethylidene)-4-methyl-4-(2,3-dihydro-6-methyl-5-phenyl-4-oxo-4H-1,3-oxazin-3-yl)-2-(2-thienylmethylidene)-3-oxo-pentanoate (Compound 207)

methyl 2-(2-fluorobenzylidene)-4-(2,3-dihydro-6-methyl-5-phenyl-4-oxo-4H-1,3-oxazin-3-yl)-4-methyl-3-oxo-pentanoate (Compound 208)

methyl 4-(2,3-dihydro-6-methyl-5-phenyl-4-oxo-4H-1,3-oxazin-3-yl)-2-(2-furylmethylidene)-4-methyl-3-oxo-pentanoate (Compound 209)

ethyl 2-(3-chlorobenzylidene)-4-(2,3-dihydro-6-methyl-5-phenyl-4-oxo-4H-1,3-oxazin-3-yl)-4-methyl-3-oxo-pentanoate (Compound 210)

ethyl 2-(benzylidene)-4-(2,3-dihydro-6-methyl-5-phenyl-4-oxo-4H-1,3-oxazin-3-yl)-4-methyl-3-oxo-pentanoate (Compound 211)

2-(2,3-dihydro-6-methyl-4-oxo-5-phenyl-4H-1,3-oxazin-3-yl)-2-methyl-3-oxo-heptan-6-ol (Compound 212)

2-(2,3-dihydro-6-methyl-4-oxo-5-phenyl-4H-1,3-oxazin-3-yl)-2-methyl-1-(3-vinylphenyl)propan-1-one) (Compound 444)

1-(2,2-difluoro-1,3-benzodioxol-5-yl)-2-(2,3-dihydro-6-methyl-4-oxo-5-phenyl-4H-1,3-oxazin-3-yl)-2-methylpropan-1-one (Compound 445)

2-(2,3-dihydro-6-methyl-4-oxo-5-phenyl-4H-1,3-oxazin-3-yl)-1-(2-fluoro-4-biphenyl)-2-methylpropan-1-one (Compound 446)

1-(4-biphenyl)-2-(2,3-dihydro-6-methyl-4-oxo-5-phenyl-4H-1,3-oxazin-3-yl)-2-methylpropan-1-one (Compound 447)

2-(2,3-dihydro-6-methyl-4-oxo-5-phenyl-4H-1,3-oxazin-3-yl)-2-methyl-1-(9-phenanthryl)propan-1-one (Compound 448)

1-(3-biphenyl)-2-(2,3-dihydro-6-methyl-4-oxo-5-phenyl-4H-1,3-oxazin-3-yl)-2-methylpropan-1-one (Compound 449)

1-(3,5-difluorophenyl)-2-(2,3-dihydro-6-methoxycarbonylmethyl-4-oxo-5-phenyl-4H-1,3-oxazin-3-yl)-2-methylpropan-1-one (Compound 700)

1-(3,5-difluorophenyl)-2-[2,3-dihydro-6-bis(methoxycarbonyl)methyl-4-oxo-5-phenyl-4H-1,3-oxazin-3-yl]-2-methylpropan-1-one (Compound 701)

1-(3,5-difluorophenyl)-2-(2,3-dihydro-6-ethoxycarbonylmethyl-4-oxo-5-phenyl-4H-1,3-oxazin-3-yl)-2-methylpropan-1-one (Compound 702)

1-(3,5-difluorophenyl)-2-[2,3-dihydro-6-bis(ethoxycarbonyl)methyl-4-oxo-5-phenyl-4H-1,3-oxazin-3-yl]-2-methylpropan-1-one (Compound 703) and 1-(3,5-difluorophenyl)-2-(6-carboxymethyl-2,3-dihydro-4-oxo-5-phenyl-4H-1,3-oxazin-3-yl)-2-methylpropan-1-one (Compound 704)

ethyl 1-[2-(2,3-dihydro-6-ethyl-4-oxo-5-phenyl-4H-1,3-oxazin-3-yl)-2-methylpropionyl]cyclopent-3-enylcarboxylate (Compound 1065)

2-(2,3-dihydro-6-methyl-4-oxo-5-phenyl-4H-1,3-oxazin-3-yl)-2-methyl-4-(1-methylcyclopropyl)butan-3-one (Compound 1066)

2-(2,3-dihydro-6-methyl-4-oxo-5-phenyl-4H-1,3-oxazin-3-yl)-2-methyl-4-(2-methylcyclopropyl)pentan-3-one (Compound 1067)

1-(bicyclo[3.1.0]hexan-1-yl)-2-(2,3-dihydro-6-methyl-4-oxo-5-phenyl-4H-1,3-oxazin-3-yl)-2-methyl-propan-1-one (Compound 1068)

2-(2,3-dihydro-6-methyl-4-oxo-5-phenyl-4H-1,3-oxazin-3-yl)-2-methyl-1-(1-methyl-2-methylene-cyclopentyl)propan-1-one (Compound 1069)

1-(bicyclo[4.1.0]heptan-2-yl)-2-(2,3-dihydro-6-methyl-4-oxo-5-phenyl-4H-1,3-oxazin-3-yl)-2-methylpropan-1-one (Compound 1070)

2-(2,3-dihydro-6-methyl-4-oxo-5-phenyl-4H-1,3-oxazin-3-yl)-2-methyl-1-(spiro[2.4]heptan-4-yl)propan-1-one (Compound 1071)

2-(2,3-dihydro-6-methyl-4-oxo-5-phenyl-4H-1,3-oxazin-3-yl)-2-methyl-1-(2-methylenecyclopentyl)propan-1-one (Compound 1072)

2-(2,3-dihydro-6-methyl-4-oxo-5-phenyl-4H-1,3-oxazin-3-yl)-2-methyl-1-(5-methyl-2-methylenecyclopentyl)propan-1-one (Compound 1073)

2-(2,3-dihydro-6-methyl-4-oxo-5-phenyl-4H-1,3-oxazin-3-yl)-2-methyl-4-(2-methylcyclopropyl)butan-3-one (Compound 1074)

2-(2,3-dihydro-6-ethyl-4-oxo-5-phenyl-4H-1,3-oxazin-3-yl)-2-methyl-1-(2-methylenecyclopentyl)propan-1-one (Compound 1075)

2-(2,3-dihydro-6-methyl-4-oxo-5-phenyl-4H-1,3-oxazin-3-yl)-2-methyl-1-(3-methylenecyclopentyl)propan-1-one (Compound 1076)

2-(2,3-dihydro-6-methyl-4-oxo-5-phenyl-4H-1,3-oxazin-3-yl)-2-methyl-1-(endo-bicyclo[2.2.1]hept-5-en-2-yl)propan-1-one (Compound 1077)

2-(2,3-dihydro-6-methyl-4-oxo-5-phenyl-4H-1,3-oxazin-3-yl)-2-methyl-1-(exo-bicyclo[2.2.1]hept-5-en-2-yl)propan-1-one (Compound 1078)2-(2,3-dihydro-6-methyl-4-oxo-5-phenyl-4H-1,3-oxazin-3-yl)-2-methyl-1-(endo-bicyclo[2.2.1]hept-2-yl)propan-1-one (Compound 1079)

2-(2,3-dihydro-6-methyl-4-oxo-5-phenyl-4H-1,3-oxazin-3-yl)-2-methyl-1-(exo-bicyclo[2.2.1]hept-2-yl)propan-1-one (Compound 1080)

5-phenylthio-2-(2,3-dihydro-6-methyl-4-oxo-5-phenyl-4H-1,3-oxazin-3-yl)-2-methylpentan-3-one (Compound 1081)

5-(3-phenoxyphenyl)amino-2-(2,3-dihydro-6-methyl-4-oxo-5-phenyl-4H-1,3-oxazin-3-yl)-2-methylpentan-3-one (Compound 1082) 5-ethylthio-2-(2,3-dihydro-6-methyl-4-oxo-5-phenyl-4H-1,3-oxazin-3-yl)-2-methylpentan-3-one (Compound 1083)

5-(2,2,2-trifluoroethylthio)-2-(2,3-dihydro-6-methyl-4-oxo-5-phenyl-4H-1,3-oxazin-3-yl)-2-methylpentan-3-one (Compound 1084)

5-cyclohexylthio-2-(2,3-dihydro-6-methyl-4-oxo-5-phenyl-4H-1,3-oxazin-3-yl)-2-methylpentan-3-one (Compound 1085)

5-benzylthio-2-(2,3-dihydro-6-methyl-4-oxo-5-phenyl-4H-1,3-oxazin-3-yl)-2-methylpentan-3-one (Compound 1086)

5-(2-furylmethyl)thio-2-(2,3-dihydro-6-methyl-4-oxo-5-phenyl-4H-1,3-oxazin-3-yl)-2-methylpentan-3-one (Compound 1087)

5-(2-pyridyl)thio-2-(2,3-dihydro-6-methyl-4-oxo-5-phenyl-4H-1,3-oxazin-3-yl)-2-methylpentan-3-one (Compound 1088)

5-(1-naphthyl)thio-2-(2,3-dihydro-6-methyl-4-oxo-5-phenyl-4H-1,3-oxazin-3-yl)-2-methylpentan-3-one (Compound 1089).

The following compounds of formula (If) below in which $R^3$ represents —CXYZ, $R^4$ and $R^5$ represent methyl and shown in Tables 1 and 2 also form part of the present invention.

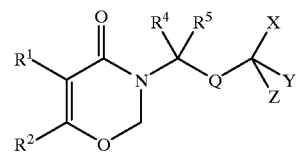

(If)

The following compounds of formula (I) in which $R^4$ and $R^5$ represent methyl, Q represents —C(=O)— and shown in Tables 3 and 5 also form part of the present invention.

The following compounds of formula (I) in which $R^4$ and $R^5$ represent methyl, Q represents —C(=O)—, r represents zero and shown in Table 4 also form part of the present invention.

In the tables below 'Ph' means phenyl, 'Me' means methyl, 'Et' means ethyl, 'Bu' means butyl and 'Bn' means benzyl. Where disubstitution of the (X+Y) ring is shown, as for example 2,3-Me cyclopropyl, it is understood to mean 2,3-dimethyl cyclopropyl. Where subscripts are omitted after atoms it will be understood that they are intended, for example CO2Et means $CO_2Et$, and CH2C2H means propynyl.

TABLE 1

| CN | R1 | R2 | Z | X + Y | Q |
|---|---|---|---|---|---|
| 1 | Ph | Me | CO2Et | cyclopentyl | CO |
| 2 | Ph | Me | CO2Et | cyclopropyl | CO |
| 3 | Ph | Me | CO2Et | cyclobutyl | CO |
| 4 | Ph | Me | CO2Et | cyclohexyl | CO |
| 5 | Ph | Me | CO2Et | cycloheptyl | CO |
| 6 | Ph | Me | CO2Et | cyclooctyl | CO |
| 7 | Ph | Me | CO2Et | 2-cyclobutenyl | CO |
| 8 | Ph | Me | CO2Et | 2-cyclopentenyl | CO |
| 9 | Ph | Me | CO2Et | 3-cyclopentenyl | CO |
| 10 | Ph | Me | CO2Et | 2-cyclohexenyl | CO |
| 11 | Ph | Me | CO2Et | 3-cyclohexenyl | CO |
| 12 | Ph | Me | CO2Et | 2-cycloheptenyl | CO |
| 13 | Ph | Me | CO2Et | 3-cycloheptenyl | CO |
| 14 | Ph | Me | CO2Et | 2-cyclooctenyl | CO |
| 15 | Ph | Me | CO2Et | 3-cyclooctenyl | CO |
| 16 | Ph | Me | CO2Et | 2-Me cyclopropyl | CO |
| 17 | Ph | Me | CO2Et | 2,3-Me cyclopropyl | CO |
| 18 | Ph | Me | CO2Et | 2-Me cyclobutyl | CO |
| 19 | Ph | Me | CO2Et | 3-Me cyclobutyl | CO |
| 20 | Ph | Me | CO2Et | 2,3-Me cyclobutyl | CO |
| 21 | Ph | Me | CO2Et | 2,4-Me cyclobutyl | CO |

TABLE 1-continued

| CN | R1 | R2 | Z | X + Y | Q |
|---|---|---|---|---|---|
| 22 | Ph | Me | CO2Et | 2-Me cyclopentyl | CO |
| 23 | Ph | Me | CO2Et | 3-Me cyclopentyl | CO |
| 24 | Ph | Me | CO2Et | 3,4-Me cyclopentyl | CO |
| 25 | Ph | Me | CO2Et | 2,5-Me cyclopentyl | CO |
| 26 | Ph | Me | CO2Et | 3,4-Me-3-cyclopentenyl | CO |
| 27 | Ph | Me | CO2Et | 2-indanyl | CO |
| 28 | Ph | Me | CO2Me | cyclopentyl | CO |
| 29 | Ph | Me | CO2Me | cyclohexyl | CO |
| 30 | Ph | Me | CO2Me | 2-cyclopentenyl | CO |
| 31 | Ph | Me | CO2Me | 3-cyclopentenyl | CO |
| 32 | Ph | Me | CO2Me | 2,3-Me cyclopropyl | CO |
| 33 | Ph | Me | CO2Me | 2-Me cyclopentyl | CO |
| 34 | Ph | Me | CO2Me | 3-methyl cyclopentyl | CO |
| 35 | Ph | Me | CO2Me | 3,4-Me cyclopentyl | CO |
| 36 | Ph | Me | CO2Me | 2,5-Me cyclopentyl | CO |
| 37 | Ph | Me | CO2t-Bu | cyclopentyl | CO |
| 38 | Ph | Me | CO2t-Bu | cyclohexyl | CO |
| 39 | Ph | Me | CO2t-Bu | 2-cyclopentenyl | CO |
| 40 | Ph | Me | CO2t-Bu | 3-cyclopentenyl | CO |
| 41 | Ph | Me | CO2t-Bu | 2-Me cyclopentyl | CO |
| 42 | Ph | Me | CO2t-Bu | 3-Me cyclopentyl | CO |
| 43 | Ph | Me | CO2t-Bu | 3,4-Me cyclopentyl | CO |
| 44 | Ph | Me | CO2Bn | cyclopentyl | CO |
| 45 | Ph | Me | CO2Bn | cyclohexyl | CO |
| 46 | Ph | Me | CO2Bn | 3-Me cyclopentyl | CO |
| 47 | Ph | Me | CO2Bn | 3,4-Me cyclopentyl | CO |
| 48 | Ph | Me | CH2COPh | cyclopentyl | CO |
| 49 | Ph | Me | CH2CO(2-Cl—Ph) | cyclopentyl | CO |
| 50 | Ph | Me | CH2CO(3-Cl—Ph) | cyclopentyl | CO |
| 51 | Ph | Me | CH2CO(4-Cl—Ph) | cyclopentyl | CO |
| 52 | 2-F Ph | Me | CO2Et | cyclopentyl | CO |
| 53 | 2-thienyl | Me | CO2Et | cyclopentyl | CO |
| 54 | Ph | CH2F | CO2Et | cyclopentyl | CO |
| 55 | Ph | Me | CN | cyclopentyl | CO |
| 56 | Ph | Me | CN | cyclopropyl | CO |
| 57 | Ph | Me | CN | cyclobutyl | CO |
| 58 | Ph | Me | CN | cyclohexyl | CO |
| 59 | Ph | Me | CN | cycloheptyl | CO |
| 60 | Ph | Me | CN | cyclooctyl | CO |
| 61 | Ph | Me | CN | 2-cyclobutenyl | CO |
| 62 | Ph | Me | CN | 2-cyclopentenyl | CO |
| 63 | Ph | Me | CN | 3-cyclopentenyl | CO |
| 64 | Ph | Me | CN | 2-cyclohexenyl | CO |
| 65 | Ph | Me | CN | 3-cyclohexenyl | CO |
| 66 | Ph | Me | CN | 2-cycloheptenyl | CO |
| 67 | Ph | Me | CN | 3-cycloheptenyl | CO |
| 68 | Ph | Me | CN | 2-cyclooctenyl | CO |
| 69 | Ph | Me | CN | 3-cyclooctenyl | CO |
| 70 | Ph | Me | CN | 2-Me cyclopropyl | CO |
| 71 | Ph | Me | CN | 2,3-Me cyclopropyl | CO |
| 72 | Ph | Me | CN | 2-Me cyclobutyl | CO |
| 73 | Ph | Me | CN | 3-Me cyclobutyl | CO |
| 74 | Ph | Me | CN | 2,3-Me cyclobutyl | CO |
| 75 | Ph | Me | CN | 2,4-Me cyclobutyl | CO |
| 76 | Ph | Me | CN | 2-Me cyclopentyl | CO |
| 77 | Ph | Me | CN | 3-Me cyclopentyl | CO |
| 78 | Ph | Me | CN | 3,4-Me cyclopentyl | CO |
| 79 | Ph | Me | CN | 2,5-Me cyclopentyl | CO |
| 80 | Ph | Me | CN | 3,4-Me-3-cyclopentenyl | CO |
| 81 | Ph | Me | CN | 2-indanyl | CO |
| 82 | Ph | Me | SO2Ph | cyclopentyl | CO |
| 83 | Ph | Me | SO2Ph | cyclopropyl | CO |
| 84 | Ph | Me | SO2Ph | cyclobutyl | CO |
| 85 | Ph | Me | SO2Ph | cyclohexyl | CO |
| 86 | Ph | Me | SO2Ph | cycloheptyl | CO |
| 87 | Ph | Me | SO2Ph | cyclooctyl | CO |
| 88 | Ph | Me | SO2Ph | 2-cyclobutenyl | CO |
| 89 | Ph | Me | SO2Ph | 2-cyclopentenyl | CO |
| 90 | Ph | Me | SO2Ph | 3-cyclopentenyl | CO |
| 91 | Ph | Me | SO2Ph | 2-cyclohexenyl | CO |
| 92 | Ph | Me | SO2Ph | 3-cyclohexenyl | CO |
| 93 | Ph | Me | SO2Ph | 2-cycloheptenyl | CO |
| 94 | Ph | Me | SO2Ph | 3-cycloheptenyl | CO |
| 95 | Ph | Me | SO2Ph | 2-cyclooctenyl | CO |
| 96 | Ph | Me | SO2Ph | 3-cyclooctenyl | CO |
| 97 | Ph | Me | SO2Ph | 2-Me cyclopropyl | CO |
| 98 | Ph | Me | SO2Ph | 2,3-Me cyclopropyl | CO |
| 99 | Ph | Me | SO2Ph | 2-Me cyclobutyl | CO |
| 100 | Ph | Me | SO2Ph | 3-Me cyclobutyl | CO |
| 101 | Ph | Me | SO2Ph | 2,3-Me cyclobutyl | CO |
| 102 | Ph | Me | SO2Ph | 2,4-Me cyclobutyl | CO |
| 103 | Ph | Me | SO2Ph | 2-Me cyclopentyl | CO |
| 104 | Ph | Me | SO2Ph | 3-Me cyclopentyl | CO |
| 105 | Ph | Me | SO2Ph | 3,4-Me cyclopentyl | CO |
| 106 | Ph | Me | SO2Ph | 2,5-Me cyclopentyl | CO |
| 107 | Ph | Me | SO2Ph | 3,4-Me-3-cyclopentenyl | CO |
| 108 | Ph | Me | SO2Ph | 2-indanyl | CO |
| 109 | Ph | Me | SO2Me | cyclopentyl | CO |
| 110 | Ph | Me | SO2Me | cyclopropyl | CO |
| 111 | Ph | Me | SO2Me | cyclobutyl | CO |
| 112 | Ph | Me | SO2Me | cyclohexyl | CO |
| 113 | Ph | Me | SO2Me | cycloheptyl | CO |
| 114 | Ph | Me | SO2Me | cyclooctyl | CO |
| 115 | Ph | Me | SO2Me | 2-cyclobutenyl | CO |
| 116 | Ph | Me | SO2Me | 2-cyclopentenyl | CO |
| 117 | Ph | Me | SO2Me | 3-cyclopentenyl | CO |
| 118 | Ph | Me | SO2Me | 2-cyclohexenyl | CO |
| 119 | Ph | Me | SO2Me | 3-cyclohexenyl | CO |
| 120 | Ph | Me | SO2Me | 2-cycloheptenyl | CO |
| 121 | Ph | Me | SO2Me | 3-cycloheptenyl | CO |
| 122 | Ph | Me | SO2Me | 2-cyclooctenyl | CO |
| 123 | Ph | Me | SO2Me | 3-cyclooctenyl | CO |
| 124 | Ph | Me | SO2Me | 2-Me cyclopropyl | CO |
| 125 | Ph | Me | SO2Me | 2,3-Me cyclopropyl | CO |
| 126 | Ph | Me | SO2Me | 2-Me cyclobutyl | CO |
| 127 | Ph | Me | SO2Me | 3-Me cyclobutyl | CO |
| 128 | Ph | Me | SO2Me | 2,3-Me cyclobutyl | CO |
| 129 | Ph | Me | SO2Me | 2,4-Me cyclobutyl | CO |
| 130 | Ph | Me | SO2Me | 2-Me cyclopentyl | CO |
| 113 | Ph | Me | SO2Me | 3-Me cyclopentyl | CO |
| 132 | Ph | Me | SO2Me | 3,4-Me cyclopentyl | CO |
| 133 | Ph | Me | SO2Me | 2,5-Me cyclopentyl | CO |
| 134 | Ph | Me | SO2Me | 3,4-Me-3-cyclopentenyl | CO |
| 135 | Ph | Me | SO2Me | 2-indanyl | CO |
| 136 | Ph | Me | COMe | cyclopentyl | CO |
| 137 | Ph | Me | COMe | cyclopropyl | CO |
| 138 | Ph | Me | COMe | cyclobutyl | CO |
| 139 | Ph | Me | COMe | cyclohexyl | CO |
| 140 | Ph | Me | COMe | cycloheptyl | CO |
| 141 | Ph | Me | COMe | cyclooctyl | CO |
| 142 | Ph | Me | COMe | 2-cyclobutenyl | CO |
| 143 | Ph | Me | COMe | 2-cyclopentenyl | CO |
| 144 | Ph | Me | COMe | 3-cyclopentenyl | CO |
| 145 | Ph | Me | COMe | 2-cyclohexenyl | CO |
| 146 | Ph | Me | COMe | 3-cyclohexenyl | CO |
| 147 | Ph | Me | COMe | 2-cycloheptenyl | CO |
| 148 | Ph | Me | COMe | 3-cycloheptenyl | CO |
| 149 | Ph | Me | COMe | 2-cyclooctenyl | CO |
| 150 | Ph | Me | COMe | 3-cyclooctenyl | CO |
| 151 | Ph | Me | COMe | 2-Me cyclopropyl | CO |
| 152 | Ph | Me | COMe | 2,3-Me cyclopropyl | CO |
| 153 | Ph | Me | COMe | 2-Me cyclobutyl | CO |
| 154 | Ph | Me | COMe | 3-Me cyclobutyl | CO |
| 155 | Ph | Me | COMe | 2,3-Me cyclobutyl | CO |
| 156 | Ph | Me | COMe | 2,4-Me cyclobutyl | CO |
| 157 | Ph | Me | COMe | 2-Me cyclopentyl | CO |
| 158 | Ph | Me | COMe | 3-Me cyclopentyl | CO |
| 159 | Ph | Me | COMe | 3,4-Me cyclopentyl | CO |
| 160 | Ph | Me | COMe | 2,5-Me cyclopentyl | CO |
| 161 | Ph | Me | COMe | 3,4-Me-3-cyclopentenyl | CO |
| 162 | Ph | Me | COMe | 2-indanyl | CO |
| 163 | Ph | Me | NO2 | cyclopentyl | CO |
| 164 | Ph | Me | NO2 | cyclopropyl | CO |
| 165 | Ph | Me | NO2 | cyclobutyl | CO |
| 166 | Ph | Me | NO2 | cyclohexyl | CO |
| 167 | Ph | Me | NO2 | cycloheptyl | CO |
| 168 | Ph | Me | NO2 | cyclooctyl | CO |
| 169 | Ph | Me | NO2 | 2-cyclobutenyl | CO |
| 170 | Ph | Me | NO2 | 2-cyclopentenyl | CO |
| 171 | Ph | Me | NO2 | 3-cyclopentenyl | CO |
| 172 | Ph | Me | NO2 | 2-cyclohexenyl | CO |

TABLE 1-continued

| CN | R1 | R2 | Z | X + Y | Q |
|---|---|---|---|---|---|
| 173 | Ph | Me | NO2 | 3-cyclohexenyl | CO |
| 174 | Ph | Me | NO2 | 2-cycloheptenyl | CO |
| 175 | Ph | Me | NO2 | 3-cycloheptenyl | CO |
| 176 | Ph | Me | NO2 | 2-cyclooctenyl | CO |
| 177 | Ph | Me | NO2 | 3-cyclooctenyl | CO |
| 178 | Ph | Me | NO2 | 2-Me cyclopropyl | CO |
| 179 | Ph | Me | NO2 | 2,3-Me cyclopropyl | CO |
| 180 | Ph | Me | NO2 | 2-Me cyclobutyl | CO |
| 181 | Ph | Me | NO2 | 3-Me cyclobutyl | CO |
| 182 | Ph | Me | NO2 | 2,3-Me cyclobutyl | CO |
| 183 | Ph | Me | NO2 | 2,4-Me cyclobutyl | CO |
| 184 | Ph | Me | NO2 | 2-Me cyclopentyl | CO |
| 185 | Ph | Me | NO2 | 3-Me cyclopentyl | CO |
| 186 | Ph | Me | NO2 | 3,4-Me cyclopentyl | CO |
| 187 | Ph | Me | NO2 | 2,5-Me cyclopentyl | CO |
| 188 | Ph | Me | NO2 | 3,4-Me-3-cyclopentenyl | CO |
| 189 | Ph | Me | NO2 | 2-indanyl | CO |

TABLE 2

| CN | R1 | R2 | Z | X | Y | Q |
|---|---|---|---|---|---|---|
| 213 | Ph | Me | CO2Et | H | i-Pr | CO |
| 214 | Ph | Me | CO2Et | H | CH2CH=CH2 | CO |
| 215 | Ph | Me | CO2Et | H | CH2C2H | CO |
| 216 | Ph | Me | CO2Et | H | Bn | CO |
| 217 | Ph | Me | CO2Et | H | Ph | CO |
| 218 | Ph | Me | CO2Et | H | 2-Cl—Ph | CO |
| 219 | Ph | Me | CO2Et | H | 3-Cl—Ph | CO |
| 220 | Ph | Me | CO2Et | H | 4-Cl—Ph | CO |
| 221 | Ph | Me | CO2Et | H | 3-CF3-Ph | CO |
| 222 | Ph | Me | CO2Et | Me | i-Pr | CO |
| 223 | Ph | Me | CO2Et | Me | CH2CH=CH2 | CO |
| 224 | Ph | Me | CO2Et | Me | CH2C2H | CO |
| 225 | Ph | Me | CO2Et | Me | CF3 | CO |
| 226 | Ph | Me | CO2Et | Me | CH2CH2OCH3 | CO |
| 227 | Ph | Me | CO2Et | Me | cyclo-Pr—Me | CO |
| 228 | Ph | Me | CO2Et | Me | Bn | CO |
| 229 | Ph | Me | CO2Et | Me | Ph | CO |
| 230 | Ph | Me | CO2Et | Me | 2-Cl—Ph | CO |
| 231 | Ph | Me | CO2Et | Me | 3-Cl—Ph | CO |
| 232 | Ph | Me | CO2Et | Me | 4-Cl—Ph | CO |
| 233 | Ph | Me | CO2Et | Me | 3-CF3-Ph | CO |
| 234 | Ph | Me | CO2Et | Et | CH2CH=CH2 | CO |
| 235 | Ph | Me | CO2Et | Et | Ph | CO |
| 236 | Ph | Me | CO2Et | F | Me | CO |
| 237 | Ph | Me | CO2Et | F | Et | CO |
| 238 | Ph | Me | CO2Et | F | Ph | CO |
| 239 | Ph | Me | CO2Me | H | Me | CO |
| 240 | Ph | Me | CO2Me | H | Et | CO |
| 241 | Ph | Me | CO2Me | Me | Me | CO |
| 242 | Ph | Me | CO2Me | Me | Et | CO |
| 243 | Ph | Me | CO2Me | Me | CH2CH=CH2 | CO |
| 244 | Ph | Me | CO2Me | Me | CH2C2H | CO |
| 245 | Ph | Me | CO2Me | Me | Ph | CO |
| 246 | Ph | Me | CO2Me | Et | Et | CO |
| 247 | Ph | Me | CO2Me | F | Me | CO |
| 248 | Ph | Me | CO2Me | F | Et | CO |
| 249 | Ph | Me | CO2Me | F | Ph | CO |
| 250 | Ph | Me | CO2t-Bu | H | Me | CO |
| 251 | Ph | Me | CO2t-Bu | H | Et | CO |
| 252 | Ph | Me | CO2t-Bu | H | i-Pr | CO |
| 253 | Ph | Me | CO2t-Bu | H | CH2CH=CH2 | CO |
| 254 | Ph | Me | CO2t-Bu | H | CH2C2H | CO |
| 255 | Ph | Me | CO2t-Bu | H | Bn | CO |
| 256 | Ph | Me | CO2t-Bu | H | Ph | CO |
| 257 | Ph | Me | CO2t-Bu | Me | Me | CO |
| 258 | Ph | Me | CO2t-Bu | Me | Et | CO |
| 259 | Ph | Me | CO2t-Bu | Me | i-Pr | CO |
| 260 | Ph | Me | CO2t-Bu | Me | CH2CH=CH2 | CO |
| 261 | Ph | Me | CO2t-Bu | Me | CH2C2H | CO |
| 262 | Ph | Me | CO2t-Bu | Me | Bn | CO |
| 263 | Ph | Me | CO2t-Bu | Me | Ph | CO |
| 264 | Ph | Me | CO2t-Bu | Et | Et | CO |
| 265 | Ph | Me | CO2t-Bu | Et | CH2CH=CH2 | CO |
| 266 | Ph | Me | CO2t-Bu | Et | Ph | CO |
| 267 | Ph | Me | CO2t-Bu | F | Me | CO |
| 268 | Ph | Me | CO2t-Bu | F | Et | CO |
| 269 | Ph | Me | CO2t-Bu | F | Ph | CO |
| 270 | Ph | Me | CO2Bn | H | H | CO |
| 271 | Ph | Me | CO2Bn | H | Me | CO |
| 272 | Ph | Me | CO2Bn | H | Et | CO |
| 273 | Ph | Me | CO2Bn | H | i-Pr | CO |
| 274 | Ph | Me | CO2Bn | H | Bn | CO |
| 275 | Ph | Me | CO2Bn | H | Ph | CO |
| 276 | Ph | Me | CO2Bn | Me | Me | CO |
| 277 | Ph | Me | CO2Bn | Me | Et | CO |
| 278 | Ph | Me | CO2Bn | Me | i-Pr | CO |
| 279 | Ph | Me | CO2Bn | Me | Bn | CO |
| 280 | Ph | Me | CO2Bn | Me | Ph | CO |
| 281 | Ph | Me | CO2Bn | Et | Et | CO |
| 282 | Ph | Me | CO2Bn | Et | Ph | CO |
| 283 | Ph | Me | CO2Bn | F | Me | CO |
| 284 | Ph | Me | CO2Bn | F | Et | CO |
| 285 | Ph | Me | CO2Bn | F | Ph | CO |
| 286 | Ph | Me | CN | H | H | CO |
| 287 | Ph | Me | CN | H | Me | CO |
| 288 | Ph | Me | CN | H | Et | CO |
| 289 | Ph | Me | CN | H | i-Pr | CO |
| 290 | Ph | Me | CN | H | CH2CH=CH2 | CO |
| 291 | Ph | Me | CN | H | CH2C2H | CO |
| 292 | Ph | Me | CN | H | Bn | CO |
| 293 | Ph | Me | CN | H | Ph | CO |
| 294 | Ph | Me | CN | Me | Me | CO |
| 295 | Ph | Me | CN | Me | Et | CO |
| 296 | Ph | Me | CN | Me | i-Pr | CO |
| 297 | Ph | Me | CN | Me | CH2CH=CH2 | CO |
| 298 | Ph | Me | CN | Me | CH2C2H | CO |
| 299 | Ph | Me | CN | Me | Ph | CO |
| 300 | Ph | Me | CN | Et | Et | CO |
| 301 | Ph | Me | CN | Et | CH2CH=CH2 | CO |
| 302 | Ph | Me | CN | F | Me | CO |
| 303 | Ph | Me | CN | F | Et | CO |
| 304 | Ph | Me | CN | F | Ph | CO |
| 305 | Ph | Me | CH2COCH3 | H | Me | CO |
| 306 | Ph | Me | CH2COCH3 | H | Et | CO |
| 307 | Ph | Me | CH2COCH3 | Me | Me | CO |
| 308 | Ph | Me | CH2COCH3 | Me | Et | CO |
| 309 | Ph | Me | CH2COCH3 | Me | i-Pr | CO |
| 310 | Ph | Me | CH2COCH3 | Me | CH2CH=CH2 | CO |
| 311 | Ph | Me | CH2COCH3 | Me | Bn | CO |
| 312 | Ph | Me | CH2COCH3 | Me | Ph | CO |
| 313 | Ph | Me | CH2COCH3 | Et | Et | CO |
| 314 | Ph | Me | CH2COCH3 | F | Me | CO |
| 315 | Ph | Me | CH2COCH3 | F | Et | CO |
| 316 | Ph | Me | CH2COPh | H | H | CO |
| 317 | Ph | Me | CH2COPh | H | Me | CO |
| 318 | Ph | Me | CH2COPh | H | Et | CO |
| 319 | Ph | Me | CH2COPh | Me | Me | CO |
| 320 | Ph | Me | CH2COPh | Me | Et | CO |
| 321 | Ph | Me | CH2COPh | Et | Et | CO |
| 322 | Ph | Me | CH2COPh | Et | CH2CH=CH2 | CO |
| 323 | Ph | Me | CH2CO(2-Cl—Ph) | H | Me | CO |
| 324 | Ph | Me | CH2CO(3-Cl—Ph) | H | Me | CO |
| 325 | Ph | Me | CH2CO(4-Cl—Ph) | H | Me | CO |
| 326 | 2-F Ph | Me | CO2Et | H | H | CO |
| 327 | 2-F Ph | Me | CO2Et | H | Me | CO |
| 328 | 2-F Ph | Me | CO2Et | H | Et | CO |
| 329 | 2-F Ph | Me | CO2Et | Me | Me | CO |
| 330 | 2-F Ph | Me | CO2Et | Me | Et | CO |
| 331 | 2-thienyl | Me | CO2Et | H | H | CO |
| 332 | 2-thienyl | Me | CO2Et | H | Me | CO |
| 333 | 2-thienyl | Me | CO2Et | H | Et | CO |
| 334 | 2-thienyl | Me | CO2Et | Me | Me | CO |
| 335 | 2-thienyl | Me | CO2Et | Me | Et | CO |
| 336 | Ph | CH2F | CO2Et | H | H | CO |

TABLE 2-continued

| CN | R1 | R2 | Z | X | Y | Q |
|---|---|---|---|---|---|---|
| 337 | Ph | CH2F | CO2Et | H | Me | CO |
| 338 | Ph | CH2F | CO2Et | H | Et | CO |
| 339 | Ph | CH2F | CO2Et | Me | Me | CO |
| 340 | Ph | CH2F | CO2Et | Me | Et | CO |
| 341 | Ph | Me | SO2Ph | H | H | CO |
| 342 | Ph | Me | SO2Ph | H | Me | CO |
| 343 | Ph | Me | SO2Ph | H | Et | CO |
| 344 | Ph | Me | SO2Ph | H | i-Pr | CO |
| 345 | Ph | Me | SO2Ph | H | CH2CH=CH2 | CO |
| 346 | Ph | Me | SO2Ph | H | CH2C2H | CO |
| 347 | Ph | Me | SO2Ph | H | Bn | CO |
| 348 | Ph | Me | SO2Ph | H | Ph | CO |
| 349 | Ph | Me | SO2Ph | H | 2-Cl—Ph | CO |
| 350 | Ph | Me | SO2Ph | H | 3-Cl—Ph | CO |
| 351 | Ph | Me | SO2Ph | H | 4-Cl—Ph | CO |
| 352 | Ph | Me | SO2Ph | H | 3-CF3-Ph | CO |
| 353 | Ph | Me | SO2Ph | Me | Me | CO |
| 354 | Ph | Me | SO2Ph | Me | Et | CO |
| 355 | Ph | Me | SO2Ph | Me | i-Pr | CO |
| 356 | Ph | Me | SO2Ph | Me | CH2CH=CH2 | CO |
| 357 | Ph | Me | SO2Ph | Me | CH2C2H | CO |
| 358 | Ph | Me | SO2Ph | Me | CF3 | CO |
| 359 | Ph | Me | SO2Ph | Me | CH2CH2OCH3 | CO |
| 360 | Ph | Me | SO2Ph | Me | cyclo-Pr—Me | CO |
| 361 | Ph | Me | SO2Ph | Me | Bn | CO |
| 362 | Ph | Me | SO2Ph | Me | Ph | CO |
| 363 | Ph | Me | SO2Ph | Me | 2-Cl—Ph | CO |
| 364 | Ph | Me | SO2Ph | Me | 3-Cl—Ph | CO |
| 365 | Ph | Me | SO2Ph | Me | 4-Cl—Ph | CO |
| 366 | Ph | Me | SO2Ph | Me | 3-CF3-Ph | CO |
| 367 | Ph | Me | SO2Me | H | H | CO |
| 368 | Ph | Me | SO2Me | H | Me | CO |
| 369 | Ph | Me | SO2Me | H | Et | CO |
| 370 | Ph | Me | SO2Me | H | i-Pr | CO |
| 371 | Ph | Me | SO2Me | H | CH2CH=CH2 | CO |
| 372 | Ph | Me | SO2Me | H | CH2C2H | CO |
| 373 | Ph | Me | SO2Me | H | Bn | CO |
| 374 | Ph | Me | SO2Me | H | Ph | CO |
| 375 | Ph | Me | SO2Me | H | 2-Cl—Ph | CO |
| 376 | Ph | Me | SO2Me | H | 3-Cl—Ph | CO |
| 377 | Ph | Me | SO2Me | H | 4-Cl—Ph | CO |
| 378 | Ph | Me | SO2Me | H | 3-CF3-Ph | CO |
| 379 | Ph | Me | SO2Me | Me | Me | CO |
| 380 | Ph | Me | SO2Me | Me | Et | CO |
| 381 | Ph | Me | SO2Me | Me | i-Pr | CO |
| 382 | Ph | Me | SO2Me | Me | CH2CH=CH2 | CO |
| 383 | Ph | Me | SO2Me | Me | CH2C2H | CO |
| 384 | Ph | Me | SO2Me | Me | CF3 | CO |
| 385 | Ph | Me | SO2Me | Me | CH2CH2OCH3 | CO |
| 386 | Ph | Me | SO2Me | Me | cyclo-Pr—Me | CO |
| 387 | Ph | Me | SO2Me | Me | Bn | CO |
| 388 | Ph | Me | SO2Me | Me | Ph | CO |
| 389 | Ph | Me | SO2Me | Me | 2-Cl—Ph | CO |
| 390 | Ph | Me | SO2Me | Me | 3-Cl—Ph | CO |
| 391 | Ph | Me | SO2Me | Me | 4-Cl—Ph | CO |
| 392 | Ph | Me | SO2Me | Me | 3-CF3-Ph | CO |
| 393 | Ph | Me | COMe | H | Me | CO |
| 394 | Ph | Me | COMe | H | Et | CO |
| 395 | Ph | Me | COMe | H | i-Pr | CO |
| 396 | Ph | Me | COMe | H | CH2CH=CH2 | CO |
| 397 | Ph | Me | COMe | H | CH2C2H | CO |
| 398 | Ph | Me | COMe | H | Bn | CO |
| 399 | Ph | Me | COMe | H | Ph | CO |
| 400 | Ph | Me | COMe | H | 2-Cl—Ph | CO |
| 401 | Ph | Me | COMe | H | 3-Cl—Ph | CO |
| 402 | Ph | Me | COMe | H | 4-Cl—Ph | CO |
| 403 | Ph | Me | COMe | H | 3-CF3-Ph | CO |
| 404 | Ph | Me | COMe | Me | Me | CO |
| 405 | Ph | Me | COMe | Me | Et | CO |
| 406 | Ph | Me | COMe | Me | i-Pr | CO |
| 407 | Ph | Me | COMe | Me | CH2CH=CH2 | CO |
| 408 | Ph | Me | COMe | Me | CH2C2H | CO |
| 409 | Ph | Me | COMe | Me | CF3 | CO |
| 410 | Ph | Me | COMe | Me | CH2CH2OCH3 | CO |
| 411 | Ph | Me | COMe | Me | cyclo-Pr—Me | CO |
| 412 | Ph | Me | COMe | Me | Bn | CO |
| 413 | Ph | Me | COMe | Me | Ph | CO |
| 414 | Ph | Me | COMe | Me | 2-Cl—Ph | CO |
| 415 | Ph | Me | COMe | Me | 3-Cl—Ph | CO |
| 416 | Ph | Me | COMe | Me | 4-Cl—Ph | CO |
| 417 | Ph | Me | COMe | Me | 3-CF3-Ph | CO |
| 418 | Ph | Me | NO2 | H | H | CO |
| 419 | Ph | Me | NO2 | H | Me | CO |
| 420 | Ph | Me | NO2 | H | Et | CO |
| 421 | Ph | Me | NO2 | H | i-Pr | CO |
| 422 | Ph | Me | NO2 | H | CH2CH=CH2 | CO |
| 423 | Ph | Me | NO2 | H | CH2C2H | CO |
| 424 | Ph | Me | NO2 | H | Bn | CO |
| 425 | Ph | Me | NO2 | H | Ph | CO |
| 426 | Ph | Me | NO2 | H | 2-Cl—Ph | CO |
| 427 | Ph | Me | NO2 | H | 3-Cl—Ph | CO |
| 428 | Ph | Me | NO2 | H | 4-Cl—Ph | CO |
| 429 | Ph | Me | NO2 | H | 3-CF3-Ph | CO |
| 430 | Ph | Me | NO2 | Me | Me | CO |
| 431 | Ph | Me | NO2 | Me | Et | CO |
| 432 | Ph | Me | NO2 | Me | i-Pr | CO |
| 433 | Ph | Me | NO2 | Me | CH2CH=CH2 | CO |
| 434 | Ph | Me | NO2 | Me | CH2C2H | CO |
| 435 | Ph | Me | NO2 | Me | CF3 | CO |
| 436 | Ph | Me | NO2 | Me | CH2CH2OCH3 | CO |
| 437 | Ph | Me | NO2 | Me | cyclo-Pr—Me | CO |
| 438 | Ph | Me | NO2 | Me | Bn | CO |
| 439 | Ph | Me | NO2 | Me | Ph | CO |
| 440 | Ph | Me | NO2 | Me | 2-Cl—Ph | CO |
| 441 | Ph | Me | NO2 | Me | 3-Cl—Ph | CO |
| 442 | Ph | Me | NO2 | Me | 4-Cl—Ph | CO |
| 443 | Ph | Me | NO2 | Me | 3-CF3-Ph | CO |

TABLE 3

| CN | R1 | R2 | R3 |
|---|---|---|---|
| 450 | Ph | Me | 3-OSO2Me Phenyl |
| 451 | Ph | Me | 3-OSO2(4-Me Ph) Phenyl |
| 452 | Ph | Me | 3-OCH2C(O)Ph Phenyl |
| 453 | Ph | Me | 3-OC(O)Ph Phenyl |
| 454 | Ph | Me | 3-CH2OMe Phenyl |
| 455 | Ph | Me | 3-CH2OSO2(4-Me Ph) Phenyl |
| 456 | Ph | Me | 3-CH2OC(O)Ph Phenyl |
| 457 | Ph | Me | 3-CH2SO2Ph |
| 458 | Ph | Me | 3,4-(—O(CH2)2O—) Phenyl |
| 459 | Ph | Me | 3,4-(—OCH2O—) Phenyl |
| 460 | 2-Cl Ph | Et | 3-OSO2Me Phenyl |
| 461 | 2-Cl Ph | Et | 3-OSO2(4-Me Ph) Phenyl |
| 462 | 2-Cl Ph | Et | 3-OCH2C(O)Ph Phenyl |
| 463 | 2-Cl Ph | Et | 3-OC(O)Ph Phenyl |
| 464 | 2-Cl Ph | Et | 3-CH2OMe Phenyl |
| 465 | 2-Cl Ph | Et | 3-CH2OSO2(4-Me Ph) Phenyl |
| 466 | 2-Cl Ph | Et | 3-CH2OC(O)Ph Phenyl |
| 467 | 2-Cl Ph | Et | 3-CH2SO2Ph |
| 468 | 2-Cl Ph | Et | 3,4-(—O(CH2)2O—) Phenyl |
| 469 | 2-Cl Ph | Et | 3,4-(—OCH2O—) Phenyl |
| 470 | 2-F Ph | CH2OMe | 3-OSO2Me Phenyl |
| 471 | 2-F Ph | CH2OMe | 3-OSO2(4-Me Ph) Phenyl |
| 472 | 2-F Ph | CH2OMe | 3-OCH2C(O)Ph Phenyl |
| 473 | 2-F Ph | CH2OMe | 3-OC(O)Ph Phenyl |
| 474 | 2-F Ph | CH2OMe | 3-CH2OMe Phenyl |
| 475 | 2-F Ph | CH2OMe | 3-CH2OSO2(4-Me Ph) Phenyl |
| 476 | 2-F Ph | CH2OMe | 3-CH2OC(O)Ph Phenyl |
| 477 | 2-F Ph | CH2OMe | 3-CH2SO2Ph |
| 478 | 2-F Ph | CH2OMe | 3,4-(—O(CH2)2O—) Phenyl |
| 479 | 2-F Ph | CH2OMe | 3,4-(—OCH2O—) Phenyl |
| 480 | 2-Br Ph | CH2F | 3-OSO2Me Phenyl |
| 481 | 2-Br Ph | CH2F | 3-OSO2(4-Me Ph) Phenyl |
| 482 | 2-Br Ph | CH2F | 3-OCH2C(O)Ph Phenyl |
| 483 | 2-Br Ph | CH2F | 3-OC(O)Ph Phenyl |
| 484 | 2-Br Ph | CH2F | 3-CH2OMe Phenyl |
| 485 | 2-Br Ph | CH2F | 3-CH2OSO2(4-Me Ph) Phenyl |
| 486 | 2-Br Ph | CH2F | 3-CH2OC(O)Ph Phenyl |
| 487 | 2-Br Ph | CH2F | 3-CH2SO2Ph |
| 488 | 2-Br Ph | CH2F | 3,4-(—O(CH2)2O—) Phenyl |

TABLE 3-continued

| CN | R1 | R2 | R3 |
|----|----|----|----|
| 489 | 2-Br Ph | CH2F | 3,4-(—OCH2O—) Phenyl |
| 490 | 2-Thienyl | CH2SO2Ph | 3-OSO2Me Phenyl |
| 491 | 2-Thienyl | CH2SO2Ph | 3-OSO2(4-Me Ph) Phenyl |
| 492 | 2-Thienyl | CH2SO2Ph | 3-OCH2C(O)Ph Phenyl |
| 493 | 2-Thienyl | CH2SO2Ph | 3-OC(O)Ph Phenyl |
| 494 | 2-Thienyl | CH2SO2Ph | 3-CH2OMe Phenyl |
| 495 | 2-Thienyl | CH2SO2Ph | 3-CH2OSO2(4-Me Ph) Phenyl |
| 496 | 2-Thienyl | CH2SO2Ph | 3-CH2OC(O)Ph Phenyl |
| 497 | 2-Thienyl | CH2SO2Ph | 3-CH2SO2Ph |
| 498 | 2-Thienyl | CH2SO2Ph | 3,4-(—O(CH2)2O—) Phenyl |
| 499 | 2-Thienyl | CH2SO2Ph | 3,4-(—OCH2O—) Phenyl |
| 500 | Ph | Et | 3-OSO2Me Phenyl |
| 501 | Ph | Et | 3-OSO2(4-Me Ph) Phenyl |
| 502 | Ph | Et | 3-OCH2C(O)Ph Phenyl |
| 503 | Ph | Et | 3-OC(O)Ph Phenyl |
| 504 | Ph | Et | 3-CH2OMe Phenyl |
| 505 | Ph | Et | 3-CH2OSO2(4-Me Ph) Phenyl |
| 506 | Ph | Et | 3-CH2OC(O)Ph Phenyl |
| 507 | Ph | Et | 3-CH2SO2Ph |
| 508 | Ph | Et | 3,4-(—O(CH2)2O—) Phenyl |
| 509 | Ph | Et | 3,4-(—OCH2O—) Phenyl |
| 510 | 2-Cl Ph | CH2OMe | 3-OSO2Me Phenyl |
| 511 | 2-Cl Ph | CH2OMe | 3-OSO2(4-Me Ph) Phenyl |
| 512 | 2-Cl Ph | CH2OMe | 3-OCH2C(O)Ph Phenyl |
| 513 | 2-Cl Ph | CH2OMe | 3-OC(O)Ph Phenyl |
| 514 | 2-Cl Ph | CH2OMe | 3-CH2OMe Phenyl |
| 515 | 2-Cl Ph | CH2OMe | 3-CH2OSO2(4-Me Ph) Phenyl |
| 516 | 2-Cl Ph | CH2OMe | 3-CH2OC(O)Ph Phenyl |
| 517 | 2-Cl Ph | CH2OMe | 3-CH2SO2Ph |
| 518 | 2-Cl Ph | CH2OMe | 3,4-(—O(CH2)2O—) Phenyl |
| 519 | 2-Cl Ph | CH2OMe | 3,4-(—OCH2O—) Phenyl |
| 520 | 2-F Ph | CH2F | 3-OSO2Me Phenyl |
| 521 | 2-F Ph | CH2F | 3-OSO2(4-Me Ph) Phenyl |
| 522 | 2-F Ph | CH2F | 3-OCH2C(O)Ph Phenyl |
| 523 | 2-F Ph | CH2F | 3-OC(O)Ph Phenyl |
| 524 | 2-F Ph | CH2F | 3-CH2OMe Phenyl |
| 525 | 2-F Ph | CH2F | 3-CH2OSO2(4-Me Ph) Phenyl |
| 526 | 2-F Ph | CH2F | 3-CH2OC(O)Ph Phenyl |
| 527 | 2-F Ph | CH2F | 3-CH2SO2Ph |
| 528 | 2-F Ph | CH2F | 3,4-(—O(CH2)2O—) Phenyl |
| 529 | 2-F Ph | CH2F | 3,4-(—OCH2O—) Phenyl |
| 530 | 2-Br Ph | CH2SO2Ph | 3-OSO2Me Phenyl |
| 531 | 2-Br Ph | CH2SO2Ph | 3-OSO2(4-Me Ph) Phenyl |
| 532 | 2-Br Ph | CH2SO2Ph | 3-OCH2C(O)Ph Phenyl |
| 533 | 2-Br Ph | CH2SO2Ph | 3-OC(O)Ph Phenyl |
| 534 | 2-Br Ph | CH2SO2Ph | 3-CH2OMe Phenyl |
| 535 | 2-Br Ph | CH2SO2Ph | 3-CH2OSO2(4-Me Ph) Phenyl |
| 536 | 2-Br Ph | CH2SO2Ph | 3-CH2OC(O)Ph Phenyl |
| 537 | 2-Br Ph | CH2SO2Ph | 3-CH2SO2Ph |
| 538 | 2-Br Ph | CH2SO2Ph | 3,4-(—O(CH2)2O—) Phenyl |
| 539 | 2-Br Ph | CH2SO2Ph | 3,4-(—OCH2O—) Phenyl |
| 540 | 2-Thienyl | Me | 3-OSO2Me Phenyl |
| 541 | 2-Thienyl | Me | 3-OSO2(4-Me Ph) Phenyl |
| 542 | 2-Thienyl | Me | 3-OCH2C(O)Ph Phenyl |
| 543 | 2-Thienyl | Me | 3-OC(O)Ph Phenyl |
| 544 | 2-Thienyl | Me | 3-CH2OMe Phenyl |
| 545 | 2-Thienyl | Me | 3-CH2OSO2(4-Me Ph) Phenyl |
| 546 | 2-Thienyl | Me | 3-CH2OC(O)Ph Phenyl |
| 547 | 2-Thienyl | Me | 3-CH2SO2Ph |
| 548 | 2-Thienyl | Me | 3,4-(—O(CH2)2O—) Phenyl |
| 549 | 2-Thienyl | Me | 3,4-(—OCH2O—) Phenyl |
| 550 | Ph | CH2OMe | 3-OSO2Me Phenyl |
| 551 | Ph | CH2OMe | 3-OSO2(4-Me Ph) Phenyl |
| 552 | Ph | CH2OMe | 3-OCH2C(O)Ph Phenyl |
| 553 | Ph | CH2OMe | 3-OC(O)Ph Phenyl |
| 554 | Ph | CH2OMe | 3-CH2OMe Phenyl |
| 555 | Ph | CH2OMe | 3-CH2OSO2(4-Me Ph) Phenyl |
| 556 | Ph | CH2OMe | 3-CH2OC(O)Ph Phenyl |
| 557 | Ph | CH2OMe | 3-CH2SO2Ph |
| 558 | Ph | CH2OMe | 3,4-(—O(CH2)2O—) Phenyl |
| 559 | Ph | CH2OMe | 3,4-(—OCH2O—) Phenyl |
| 560 | 2-Cl Ph | CH2F | 3-OSO2Me Phenyl |
| 561 | 2-Cl Ph | CH2F | 3-OSO2(4-Me Ph) Phenyl |
| 562 | 2-Cl Ph | CH2F | 3-OCH2C(O)Ph Phenyl |
| 563 | 2-Cl Ph | CH2F | 3-OC(O)Ph Phenyl |
| 564 | 2-Cl Ph | CH2F | 3-CH2OMe Phenyl |
| 565 | 2-Cl Ph | CH2F | 3-CH2OSO2(4-Me Ph) Phenyl |
| 566 | 2-Cl Ph | CH2F | 3-CH2OC(O)Ph Phenyl |
| 567 | 2-Cl Ph | CH2F | 3-CH2SO2Ph |
| 568 | 2-Cl Ph | CH2F | 3,4-(—O(CH2)2O—) Phenyl |
| 569 | 2-Cl Ph | CH2F | 3,4-(—OCH2O—) Phenyl |
| 570 | 2-F Ph | CH2SO2Ph | 3-OSO2Me Phenyl |
| 571 | 2-F Ph | CH2SO2Ph | 3-OSO2(4-Me Ph) Phenyl |
| 572 | 2-F Ph | CH2SO2Ph | 3-OCH2C(O)Ph Phenyl |
| 573 | 2-F Ph | CH2SO2Ph | 3-OC(O)Ph Phenyl |
| 574 | 2-F Ph | CH2SO2Ph | 3-CH2OMe Phenyl |
| 575 | 2-F Ph | CH2SO2Ph | 3-CH2OSO2(4-Me Ph) Phenyl |
| 576 | 2-F Ph | CH2SO2Ph | 3-CH2OC(O)Ph Phenyl |
| 577 | 2-F Ph | CH2SO2Ph | 3-CH2SO2Ph |
| 578 | 2-F Ph | CH2SO2Ph | 3,4-(—O(CH2)2O—) Phenyl |
| 579 | 2-F Ph | CH2SO2Ph | 3,4-(—OCH2O—) Phenyl |
| 580 | 2-F Ph | Me | 3-OSO2Me Phenyl |
| 581 | 2-F Ph | Me | 3-OSO2(4-Me Ph) Phenyl |
| 582 | 2-F Ph | Me | 3-OCH2C(O)Ph Phenyl |
| 583 | 2-Br Ph | Me | 3-OC(O)Ph Phenyl |
| 584 | 2-Br Ph | Me | 3-CH2OMe Phenyl |
| 585 | 2-Br Ph | Me | 3-CH2OSO2(4-Me Ph) Phenyl |
| 586 | 2-Br Ph | Me | 3-CH2OC(O)Ph Phenyl |
| 587 | 2-Br Ph | Me | 3-CH2SO2Ph |
| 588 | 2-Br Ph | Me | 3,4-(—O(CH2)2O—) Phenyl |
| 589 | 2-Br Ph | Me | 3,4-(—OCH2O—) Phenyl |
| 590 | 2-Thienyl | Et | 3-OSO2Me Phenyl |
| 591 | 2-Thienyl | Et | 3-OSO2(4-Me Ph) Phenyl |
| 592 | 2-Thienyl | Et | 3-OCH2C(O)Ph Phenyl |
| 593 | 2-Thienyl | Et | 3-OC(O)Ph Phenyl |
| 594 | 2-Thienyl | Et | 3-CH2OMe Phenyl |
| 595 | 2-Thienyl | Et | 3-CH2OSO2(4-Me Ph) Phenyl |
| 596 | 2-Thienyl | Et | 3-CH2OC(O)Ph Phenyl |
| 597 | 2-Thienyl | Et | 3-CH2SO2Ph |
| 598 | 2-Thienyl | Et | 3,4-(—O(CH2)2O—) Phenyl |
| 599 | 2-Thienyl | Et | 3,4-(—OCH2O—) Phenyl |
| 600 | Ph | CH2F | 3-OSO2Me Phenyl |
| 601 | Ph | CH2F | 3-OSO2(4-Me Ph) Phenyl |
| 602 | Ph | CH2F | 3-OCH2C(O)Ph Phenyl |
| 603 | Ph | CH2F | 3-OC(O)Ph Phenyl |
| 604 | Ph | CH2F | 3-CH2OMe Phenyl |
| 605 | Ph | CH2F | 3-CH2OSO2(4-Me Ph) Phenyl |
| 606 | Ph | CH2F | 3-CH2OC(O)Ph Phenyl |
| 607 | Ph | CH2F | 3-CH2SO2Ph |
| 608 | Ph | CH2F | 3,4-(—O(CH2)2O—) Phenyl |
| 609 | Ph | CH2F | 3,4-(—OCH2O—) Phenyl |
| 610 | 2-Cl Ph | CH2SO2Ph | 3-OSO2Me Phenyl |
| 611 | 2-Cl Ph | CH2SO2Ph | 3-OSO2(4-Me Ph) Phenyl |
| 612 | 2-Cl Ph | CH2SO2Ph | 3-OCH2C(O)Ph Phenyl |
| 613 | 2-Cl Ph | CH2SO2Ph | 3-OC(O)Ph Phenyl |
| 614 | 2-Cl Ph | CH2SO2Ph | 3-CH2OMe Phenyl |
| 615 | 2-Cl Ph | CH2SO2Ph | 3-CH2OSO2(4-Me Ph) Phenyl |
| 616 | 2-Cl Ph | CH2SO2Ph | 3-CH2OC(O)Ph Phenyl |
| 617 | 2-Cl Ph | CH2SO2Ph | 3-CH2SO2Ph |
| 618 | 2-Cl Ph | CH2SO2Ph | 3,4-(—O(CH2)2O—) Phenyl |
| 619 | 2-Cl Ph | CH2SO2Ph | 3,4-(—OCH2O—) Phenyl |
| 620 | 2-F Ph | Me | 3-OSO2Me Phenyl |
| 621 | 2-F Ph | Me | 3-OSO2(4-Me Ph) Phenyl |
| 622 | 2-F Ph | Me | 3-OCH2C(O)Ph Phenyl |
| 623 | 2-F Ph | Me | 3-OC(O)Ph Phenyl |
| 624 | 2-F Ph | Me | 3-CH2OMe Phenyl |
| 625 | 2-F Ph | Me | 3-CH2OSO2(4-Me Ph) Phenyl |
| 626 | 2-F Ph | Me | 3-CH2OC(O)Ph Phenyl |
| 627 | 2-F Ph | Me | 3-CH2SO2Ph |
| 628 | 2-F Ph | Me | 3,4-(—O(CH2)2O—) Phenyl |
| 629 | 2-F Ph | Me | 3,4-(—OCH2O—) Phenyl |
| 630 | 2-Br Ph | Et | 3-OSO2Me Phenyl |
| 631 | 2-Br Ph | Et | 3-OSO2(4-Me Ph) Phenyl |
| 632 | 2-Br Ph | Et | 3-OCH2C(O)Ph Phenyl |
| 633 | 2-Br Ph | Et | 3-OC(O)Ph Phenyl |
| 634 | 2-Br Ph | Et | 3-CH2OMe Phenyl |
| 635 | 2-Br Ph | Et | 3-CH2OSO2(4-Me Ph) Phenyl |
| 636 | 2-Br Ph | Et | 3-CH2OC(O)Ph Phenyl |
| 637 | 2-Br Ph | Et | 3-CH2SO2Ph |
| 638 | 2-Br Ph | Et | 3,4-(—O(CH2)2O—) Phenyl |
| 639 | 2-Br Ph | Et | 3,4-(—OCH2O—) Phenyl |
| 640 | 2-Thienyl | CH2OMe | 3-OSO2Me Phenyl |
| 641 | 2-Thienyl | CH2OMe | 3-OSO2(4-Me Ph) Phenyl |
| 642 | 2-Thienyl | CH2OMe | 3-OCH2C(O)Ph Phenyl |

TABLE 3-continued

| CN | R1 | R2 | R3 |
|---|---|---|---|
| 643 | 2-Thienyl | CH2OMe | 3-OC(O)Ph Phenyl |
| 644 | 2-Thienyl | CH2OMe | 3-CH2OMe Phenyl |
| 645 | 2-Thienyl | CH2OMe | 3-CH2OSO2(4-Me Ph) Phenyl |
| 646 | 2-Thienyl | CH2OMe | 3-CH2OC(O)Ph Phenyl |
| 647 | 2-Thienyl | CH2OMe | 3-CH2SO2Ph |
| 648 | 2-Thienyl | CH2OMe | 3,4-(—O(CH2)2O—) Phenyl |
| 649 | 2-Thienyl | CH2OMe | 3,4-(—OCH2O—) Phenyl |
| 650 | Ph | CH2SO2Ph | 3-OSO2Me Phenyl |
| 651 | Ph | CH2SO2Ph | 3-OSO2(4-Me Ph) Phenyl |
| 652 | Ph | CH2SO2Ph | 3-OCH2C(O)Ph Phenyl |
| 653 | Ph | CH2SO2Ph | 3-OC(O)Ph Phenyl |
| 654 | Ph | CH2SO2Ph | 3-CH2OMe Phenyl |
| 655 | Ph | CH2SO2Ph | 3-CH2OSO2(4-Me Ph) Phenyl |
| 656 | Ph | CH2SO2Ph | 3-CH2OC(O)Ph Phenyl |
| 657 | Ph | CH2SO2Ph | 3-CH2SO2Ph |
| 658 | Ph | CH2SO2Ph | 3,4-(—O(CH2)2O—) Phenyl |
| 659 | Ph | CH2SO2Ph | 3,4-(—OCH2O—) Phenyl |
| 660 | 2-Cl Ph | Me | 3-OSO2Me Phenyl |
| 661 | 2-Cl Ph | Me | 3-OSO2(4-Me Ph) Phenyl |
| 662 | 2-Cl Ph | Me | 3-OCH2C(O)Ph Phenyl |
| 663 | 2-Cl Ph | Me | 3-OC(O)Ph Phenyl |
| 664 | 2-Cl Ph | Me | 3-CH2OMe Phenyl |
| 665 | 2-Cl Ph | Me | 3-CH2OSO2(4-Me Ph) Phenyl |
| 666 | 2-Cl Ph | Me | 3-CH2OC(O)Ph Phenyl |
| 667 | 2-Cl Ph | Me | 3-CH2SO2Ph |
| 668 | 2-Cl Ph | Me | 3,4-(—O(CH2)2O—) Phenyl |
| 669 | 2-Cl Ph | Me | 3,4-(—OCH2O—) Phenyl |
| 670 | 2-F Ph | Et | 3-OSO2Me Phenyl |
| 671 | 2-F Ph | Et | 3-OSO2(4-Me Ph) Phenyl |
| 672 | 2-F Ph | Et | 3-OCH2C(O)Ph Phenyl |
| 673 | 2-F Ph | Et | 3-OC(O)Ph Phenyl |
| 674 | 2-F Ph | Et | 3-CH2OMe Phenyl |
| 675 | 2-F Ph | Et | 3-CH2OSO2(4-Me Ph) Phenyl |
| 676 | 2-F Ph | Et | 3-CH2OC(O)Ph Phenyl |
| 677 | 2-F Ph | Et | 3-CH2SO2Ph |
| 678 | 2-F Ph | Et | 3,4-(—O(CH2)2O—) Phenyl |
| 679 | 2-F Ph | Et | 3,4-(—OCH2O—) Phenyl |
| 680 | 2-Br Ph | CH2OMe | 3-OSO2Me Phenyl |
| 681 | 2-Br Ph | CH2OMe | 3-OSO2(4-Me Ph) Phenyl |
| 682 | 2-Br Ph | CH2OMe | 3-OCH2C(O)Ph Phenyl |
| 683 | 2-Br Ph | CH2OMe | 3-OC(O)Ph Phenyl |
| 684 | 2-Br Ph | CH2OMe | 3-CH2OMe Phenyl |
| 685 | 2-Br Ph | CH2OMe | 3-CH2OSO2(4-Me Ph) Phenyl |
| 686 | 2-Br Ph | CH2OMe | 3-CH2OC(O)Ph Phenyl |
| 687 | 2-Br Ph | CH2OMe | 3-CH2SO2Ph |
| 688 | 2-Br Ph | CH2OMe | 3,4-(—O(CH2)2O—) Phenyl |
| 689 | 2-Br Ph | CH2OMe | 3,4-(—OCH2O—) Phenyl |
| 690 | 2-Thienyl | CH2F | 3-OSO2Me Phenyl |
| 691 | 2-Thienyl | CH2F | 3-OSO2(4-Me Ph) Phenyl |
| 692 | 2-Thienyl | CH2F | 3-OCH2C(O)Ph Phenyl |
| 693 | 2-Thienyl | CH2F | 3-OC(O)Ph Phenyl |
| 694 | 2-Thienyl | CH2F | 3-CH2OMe Phenyl |
| 695 | 2-Thienyl | CH2F | 3-CH2OSO2(4-Me Ph) Phenyl |
| 696 | 2-Thienyl | CH2F | 3-CH2OC(O)Ph Phenyl |
| 697 | 2-Thienyl | CH2F | 3-CH2SO2Ph |
| 698 | 2-Thienyl | CH2F | 3,4-(—O(CH2)2O—) Phenyl |
| 699 | 2-Thienyl | CH2F | 3,4-(—OCH2O—) Phenyl |

TABLE 4

| CN | R1 | R2 | R3 |
|---|---|---|---|
| 705 | Ph | CH2CO2(cyclopentyl) | t-Bu |
| 706 | Ph | CH2CO2(t-Bu) | cyclopentyl |
| 707 | Ph | CH2CO2(cyclobutyl) | i-Bu |
| 708 | Ph | CH2Ph | 3-OMe Phenyl |
| 709 | Ph | CH2SO2Ph | 3-Cl phenyl |
| 710 | Ph | CH2OSO2(4-MePh) | 3-Me Phenyl |
| 711 | Ph | CH2OSO2Me | t-Bu |
| 712 | Ph | CH2OCH2C(O)Ph | cyclopentyl |
| 713 | Ph | CH2C(O)Me | i-Bu |
| 714 | Ph | CH2C(O)Ph | 3-OMe Phenyl |
| 715 | 2-Cl Ph | CH2CO2(cyclopentyl) | 3-Cl phenyl |
| 716 | 2-Cl Ph | CH2CO2(t-Bu) | 3-Me Phenyl |
| 717 | 2-Cl Ph | CH2CO2(cyclobutyl) | t-Bu |
| 718 | 2-Cl Ph | CH2Ph | cyclopentyl |
| 719 | 2-Cl Ph | CH2SO2Ph | i-Bu |
| 720 | 2-Cl Ph | CH2OSO2(4-MePh) | 3-OMe Phenyl |
| 721 | 2-Cl Ph | CH2OSO2Me | 3-Cl phenyl |
| 722 | 2-Cl Ph | CH2OCH2C(O)Ph | 3-Me Phenyl |
| 723 | 2-Cl Ph | CH2C(O)Me | t-Bu |
| 724 | 2-Cl Ph | CH2C(O)Ph | cyclopentyl |
| 725 | 2-F Ph | CH2CO2(cyclopentyl) | i-Bu |
| 726 | 2-F Ph | CH2CO2(t-Bu) | 3-OMe Phenyl |
| 727 | 2-F Ph | CH2CO2(cyclobutyl) | 3-Cl phenyl |
| 728 | 2-F Ph | CH2Ph | 3-Me Phenyl |
| 729 | 2-F Ph | CH2SO2Ph | t-Bu |
| 730 | 2-F Ph | CH2OSO2(4-MePh) | cyclopentyl |
| 731 | 2-F Ph | CH2OSO2Me | i-Bu |
| 732 | 2-F Ph | CH2OCH2C(O)Ph | 3-OMe Phenyl |
| 733 | 2-F Ph | CH2C(O)Me | 3-Cl phenyl |
| 734 | 2-F Ph | CH2C(O)Ph | 3-Me Phenyl |
| 735 | 2-Br Ph | CH2CO2(cyclopentyl) | t-Bu |
| 736 | 2-Br Ph | CH2CO2(t-Bu) | cyclopentyl |
| 737 | 2-Br Ph | CH2CO2(cyclobutyl) | i-Bu |
| 738 | 2-Br Ph | CH2Ph | 3-OMe Phenyl |
| 739 | 2-Br Ph | CH2SO2Ph | 3-Cl phenyl |
| 740 | 2-Br Ph | CH2OSO2(4-MePh) | 3-Me Phenyl |
| 741 | 2-Br Ph | CH2OSO2Me | t-Bu |
| 742 | 2-Br Ph | CH2OCH2C(O)Ph | cyclopentyl |
| 743 | 2-Br Ph | CH2C(O)Me | i-Bu |
| 744 | 2-Br Ph | CH2C(O)Ph | 3-OMe Phenyl |
| 745 | 2-Me Ph | CH2CO2(cyclopentyl) | 3-Cl phenyl |
| 746 | 2-Me Ph | CH2CO2(t-Bu) | 3-Me Phenyl |
| 747 | 2-Me Ph | CH2CO2(cyclobutyl) | t-Bu |
| 748 | 2-Me Ph | CH2Ph | cyclopentyl |
| 749 | 2-Me Ph | CH2SO2Ph | i-Bu |
| 750 | 2-Me Ph | CH2OSO2(4-MePh) | 3-OMe Phenyl |
| 751 | 2-Me Ph | CH2OSO2Me | 3-Cl phenyl |
| 752 | 2-Me Ph | CH2OCH2C(O)Ph | 3-Me Phenyl |
| 753 | 2-Me Ph | CH2C(O)Me | t-Bu |
| 754 | 2-Me Ph | CH2C(O)Ph | cyclopentyl |
| 755 | 2-Thienyl | CH2CO2(cyclopentyl) | i-Bu |
| 756 | 2-Thienyl | CH2CO2(t-Bu) | 3-OMe Phenyl |
| 757 | 2-Thienyl | CH2CO2(cyclobutyl) | 3-Cl phenyl |
| 758 | 2-Thienyl | CH2Ph | 3-Me Phenyl |
| 759 | 2-Thienyl | CH2SO2Ph | t-Bu |
| 760 | 2-Thienyl | CH2OSO2(4-MePh) | cyclopentyl |
| 761 | 2-Thienyl | CH2OSO2Me | i-Bu |
| 762 | 2-Thienyl | CH2OCH2C(O)Ph | 3-OMe Phenyl |
| 763 | 2-Thienyl | CH2C(O)Me | 3-Cl phenyl |
| 764 | 2-Thienyl | CH2C(O)Ph | 3-Me Phenyl |
| 765 | Ph | CH2CO2(cyclopentyl) | cyclopentyl |
| 766 | Ph | CH2CO2(t-Bu) | i-Bu |
| 767 | Ph | CH2CO2(cyclobutyl) | 3-OMe Phenyl |
| 768 | Ph | CH2Ph | 3-Cl phenyl |
| 769 | Ph | CH2SO2Ph | 3-Me Phenyl |
| 770 | Ph | CH2OSO2(4-MePh) | t-Bu |
| 771 | Ph | CH2OSO2Me | cyclopentyl |
| 772 | Ph | CH2OCH2C(O)Ph | i-Bu |
| 773 | Ph | CH2C(O)Me | 3-OMe Phenyl |
| 774 | Ph | CH2C(O)Ph | 3-Cl phenyl |
| 775 | 2-Cl Ph | CH2CO2(cyclopentyl) | 3-Me Phenyl |
| 776 | 2-Cl Ph | CH2CO2(t-Bu) | t-Bu |
| 777 | 2-Cl Ph | CH2CO2(cyclobutyl) | cyclopentyl |
| 778 | 2-Cl Ph | CH2Ph | i-Bu |
| 779 | 2-Cl Ph | CH2SO2Ph | 3-OMe Phenyl |
| 780 | 2-Cl Ph | CH2OSO2(4-MePh) | 3-Cl phenyl |
| 781 | 2-Cl Ph | CH2OSO2Me | 3-Me Phenyl |
| 782 | 2-Cl Ph | CH2OCH2C(O)Ph | t-Bu |
| 783 | 2-Cl Ph | CH2C(O)Me | cyclopentyl |
| 784 | 2-Cl Ph | CH2C(O)Ph | i-Bu |
| 785 | 2-F Ph | CH2CO2(cyclopentyl) | 3-OMe Phenyl |
| 786 | 2-F Ph | CH2CO2(t-Bu) | 3-Cl phenyl |
| 787 | 2-F Ph | CH2CO2(cyclobutyl) | 3-Me Phenyl |
| 788 | 2-F Ph | CH2Ph | t-Bu |
| 789 | 2-F Ph | CH2SO2Ph | cyclopentyl |
| 790 | 2-F Ph | CH2OSO2(4-MePh) | i-Bu |
| 791 | 2-F Ph | CH2OSO2Me | 3-OMe Phenyl |
| 792 | 2-F Ph | CH2OCH2C(O)Ph | 3-Cl phenyl |
| 793 | 2-F Ph | CH2C(O)Me | 3-Me Phenyl |

TABLE 4-continued

| CN | R1 | R2 | R3 |
|---|---|---|---|
| 794 | 2-F Ph | CH2C(O)Ph | t-Bu |
| 795 | 2-Br Ph | CH2CO2(cyclopentyl) | cyclopentyl |
| 796 | 2-Br Ph | CH2CO2(t-Bu) | i-Bu |
| 797 | 2-Br Ph | CH2CO2(cyclobutyl) | 3-OMe Phenyl |
| 798 | 2-Br Ph | CH2Ph | 3-Cl phenyl |
| 799 | 2-Br Ph | CH2SO2Ph | 3-Me Phenyl |
| 800 | 2-Br Ph | CH2OSO2(4-MePh) | t-Bu |
| 801 | 2-Br Ph | CH2OSO2Me | cyclopentyl |
| 802 | 2-Br Ph | CH2OCH2C(O)Ph | i-Bu |
| 803 | 2-Br Ph | CH2C(O)Me | 3-OMe Phenyl |
| 804 | 2-Br Ph | CH2C(O)Ph | 3-Cl phenyl |
| 805 | 2-Me Ph | CH2CO2(cyclopentyl) | 3-Me Phenyl |
| 806 | 2-Me Ph | CH2CO2(t-Bu) | t-Bu |
| 807 | 2-Me Ph | CH2CO2(cyclobutyl) | cyclopentyl |
| 808 | 2-Me Ph | CH2Ph | i-Bu |
| 809 | 2-Me Ph | CH2SO2Ph | 3-OMe Phenyl |
| 810 | 2-Me Ph | CH2OSO2(4-MePh) | 3-Cl phenyl |
| 811 | 2-Me Ph | CH2OSO2Me | 3-Me Phenyl |
| 812 | 2-Me Ph | CH2OCH2C(O)Ph | t-Bu |
| 813 | 2-Me Ph | CH2C(O)Me | cyclopentyl |
| 814 | 2-Me Ph | CH2C(O)Ph | i-Bu |
| 815 | 2-Thienyl | CH2CO2(cyclopentyl) | 3-OMe Phenyl |
| 816 | 2-Thienyl | CH2CO2(t-Bu) | 3-Cl phenyl |
| 817 | 2-Thienyl | CH2CO2(cyclobutyl) | 3-Me Phenyl |
| 818 | 2-Thienyl | CH2Ph | t-Bu |
| 819 | 2-Thienyl | CH2SO2Ph | cyclopentyl |
| 820 | 2-Thienyl | CH2OSO2(4-MePh) | i-Bu |
| 821 | 2-Thienyl | CH2OSO2Me | 3-OMe Phenyl |
| 822 | 2-Thienyl | CH2OCH2C(O)Ph | 3-Cl phenyl |
| 823 | 2-Thienyl | CH2C(O)Me | 3-Me Phenyl |
| 824 | 2-Thienyl | CH2C(O)Ph | t-Bu |
| 825 | Ph | CH2CO2(cyclopentyl) | i-Bu |
| 826 | Ph | CH2CO2(t-Bu) | 3-OMe Phenyl |
| 827 | Ph | CH2CO2(cyclobutyl) | 3-Cl phenyl |
| 828 | Ph | CH2Ph | 3-Me Phenyl |
| 829 | Ph | CH2SO2Ph | t-Bu |
| 830 | Ph | CH2OSO2(4-MePh) | cyclopentyl |
| 831 | Ph | CH2OSO2Me | i-Bu |
| 832 | Ph | CH2OCH2C(O)Ph | 3-OMe Phenyl |
| 833 | Ph | CH2C(O)Me | 3-Cl phenyl |
| 834 | Ph | CH2C(O)Ph | 3-Me Phenyl |
| 835 | 2-Cl Ph | CH2CO2(cyclopentyl) | t-Bu |
| 836 | 2-Cl Ph | CH2CO2(t-Bu) | cyclopentyl |
| 837 | 2-Cl Ph | CH2CO2(cyclobutyl) | i-Bu |
| 838 | 2-Cl Ph | CH2Ph | 3-OMe Phenyl |
| 839 | 2-Cl Ph | CH2SO2Ph | 3-Cl phenyl |
| 840 | 2-Cl Ph | CH2OSO2(4-MePh) | 3-Me Phenyl |
| 841 | 2-Cl Ph | CH2OSO2Me | t-Bu |
| 842 | 2-Cl Ph | CH2OCH2C(O)Ph | cyclopentyl |
| 843 | 2-Cl Ph | CH2C(O)Me | i-Bu |
| 844 | 2-Cl Ph | CH2C(O)Ph | 3-OMe Phenyl |
| 845 | 2-F Ph | CH2CO2(cyclopentyl) | 3-Cl phenyl |
| 846 | 2-F Ph | CH2CO2(t-Bu) | 3-Me Phenyl |
| 847 | 2-F Ph | CH2CO2(cyclobutyl) | t-Bu |
| 848 | 2-F Ph | CH2Ph | cyclopentyl |
| 849 | 2-F Ph | CH2SO2Ph | i-Bu |
| 850 | 2-F Ph | CH2OSO2(4-MePh) | 3-OMe Phenyl |
| 851 | 2-F Ph | CH2OSO2Me | 3-Cl phenyl |
| 852 | 2-F Ph | CH2OCH2C(O)Ph | 3-Me Phenyl |
| 853 | 2-F Ph | CH2C(O)Me | t-Bu |
| 854 | 2-F Ph | CH2C(O)Ph | cyclopentyl |
| 855 | 2-Br Ph | CH2CO2(cyclopentyl) | i-Bu |
| 856 | 2-Br Ph | CH2CO2(t-Bu) | 3-OMe Phenyl |
| 857 | 2-Br Ph | CH2CO2(cyclobutyl) | 3-Cl phenyl |
| 858 | 2-Br Ph | CH2Ph | 3-Me Phenyl |
| 859 | 2-Br Ph | CH2SO2Ph | t-Bu |
| 860 | 2-Br Ph | CH2OSO2(4-MePh) | cyclopentyl |
| 861 | 2-Br Ph | CH2OSO2Me | i-Bu |
| 862 | 2-Br Ph | CH2OCH2C(O)Ph | 3-OMe Phenyl |
| 863 | 2-Br Ph | CH2C(O)Me | 3-Cl phenyl |
| 864 | 2-Br Ph | CH2C(O)Ph | 3-Me Phenyl |
| 865 | 2-Me Ph | CH2CO2(cyclopentyl) | t-Bu |
| 866 | 2-Me Ph | CH2CO2(t-Bu) | cyclopentyl |
| 867 | 2-Me Ph | CH2CO2(cyclobutyl) | i-Bu |
| 868 | 2-Me Ph | CH2Ph | 3-OMe Phenyl |
| 869 | 2-Me Ph | CH2SO2Ph | 3-Cl phenyl |
| 870 | 2-Me Ph | CH2OSO2(4-MePh) | 3-Me Phenyl |
| 871 | 2-Me Ph | CH2OSO2Me | t-Bu |
| 872 | 2-Me Ph | CH2OCH2C(O)Ph | cyclopentyl |
| 873 | 2-Me Ph | CH2C(O)Me | i-Bu |
| 874 | 2-Me Ph | CH2C(O)Ph | 3-OMe Phenyl |
| 875 | 2-Thienyl | CH2CO2(cyclopentyl) | 3-Cl phenyl |
| 876 | 2-Thienyl | CH2CO2(t-Bu) | 3-Me Phenyl |
| 877 | 2-Thienyl | CH2CO2(cyclobutyl) | t-Bu |
| 878 | 2-Thienyl | CH2Ph | cyclopentyl |
| 879 | 2-Thienyl | CH2SO2Ph | i-Bu |
| 880 | 2-Thienyl | CH2OSO2(4-MePh) | 3-OMe Phenyl |
| 881 | 2-Thienyl | CH2OSO2Me | 3-Cl phenyl |
| 882 | 2-Thienyl | CH2OCH2C(O)Ph | 3-Me Phenyl |
| 883 | 2-Thienyl | CH2C(O)Me | t-Bu |
| 884 | 2-Thienyl | CH2C(O)Ph | cyclopentyl |
| 885 | Ph | CH2CO2(cyclopentyl) | 3-OMe Phenyl |
| 886 | Ph | CH2CO2(t-Bu) | 3-Cl phenyl |
| 887 | Ph | CH2CO2(cyclobutyl) | 3-Me Phenyl |
| 888 | Ph | CH2Ph | t-Bu |
| 889 | Ph | CH2SO2Ph | cyclopentyl |
| 890 | Ph | CH2OSO2(4-MePh) | i-Bu |
| 891 | Ph | CH2OSO2Me | 3-OMe Phenyl |
| 892 | Ph | CH2OCH2C(O)Ph | 3-Cl phenyl |
| 893 | Ph | CH2C(O)Me | 3-Me Phenyl |
| 894 | Ph | CH2C(O)Ph | t-Bu |
| 895 | 2-Cl Ph | CH2CO2(cyclopentyl) | cyclopentyl |
| 896 | 2-Cl Ph | CH2CO2(t-Bu) | i-Bu |
| 897 | 2-Cl Ph | CH2CO2(cyclobutyl) | 3-OMe Phenyl |
| 898 | 2-Cl Ph | CH2Ph | 3-Cl phenyl |
| 899 | 2-Cl Ph | CH2SO2Ph | 3-Me Phenyl |
| 900 | 2-Cl Ph | CH2OSO2(4-MePh) | t-Bu |
| 901 | 2-Cl Ph | CH2OSO2Me | cyclopentyl |
| 902 | 2-Cl Ph | CH2OCH2C(O)Ph | i-Bu |
| 903 | 2-Cl Ph | CH2C(O)Me | 3-OMe Phenyl |
| 904 | 2-Cl Ph | CH2C(O)Ph | 3-Cl phenyl |
| 905 | 2-F Ph | CH2CO2(cyclopentyl) | 3-Me Phenyl |
| 906 | 2-F Ph | CH2CO2(t-Bu) | t-Bu |
| 907 | 2-F Ph | CH2CO2(cyclobutyl) | cyclopentyl |
| 908 | 2-F Ph | CH2Ph | i-Bu |
| 909 | 2-F Ph | CH2SO2Ph | 3-OMe Phenyl |
| 910 | 2-F Ph | CH2OSO2(4-MePh) | 3-Cl phenyl |
| 911 | 2-F Ph | CH2OSO2Me | 3-Me Phenyl |
| 912 | 2-F Ph | CH2OCH2C(O)Ph | t-Bu |
| 913 | 2-F Ph | CH2C(O)Me | cyclopentyl |
| 914 | 2-F Ph | CH2C(O)Ph | i-Bu |
| 915 | 2-Br Ph | CH2CO2(cyclopentyl) | 3-OMe Phenyl |
| 916 | 2-Br Ph | CH2CO2(t-Bu) | 3-Cl phenyl |
| 917 | 2-Br Ph | CH2CO2(cyclobutyl) | 3-Me Phenyl |
| 918 | 2-Br Ph | CH2Ph | t-Bu |
| 919 | 2-Br Ph | CH2SO2Ph | cyclopentyl |
| 920 | 2-Br Ph | CH2OSO2(4-MePh) | i-Bu |
| 921 | 2-Br Ph | CH2OSO2Me | 3-OMe Phenyl |
| 922 | 2-Br Ph | CH2OCH2C(O)Ph | 3-Cl phenyl |
| 923 | 2-Br Ph | CH2C(O)Me | 3-Me Phenyl |
| 924 | 2-Br Ph | CH2C(O)Ph | t-Bu |
| 925 | 2-Me Ph | CH2CO2(cyclopentyl) | cyclopentyl |
| 926 | 2-Me Ph | CH2CO2(t-Bu) | i-Bu |
| 927 | 2-Me Ph | CH2CO2(cyclobutyl) | 3-OMe Phenyl |
| 928 | 2-Me Ph | CH2Ph | 3-Cl phenyl |
| 929 | 2-Me Ph | CH2SO2Ph | 3-Me Phenyl |
| 930 | 2-Me Ph | CH2OSO2(4-MePh) | t-Bu |
| 931 | 2-Me Ph | CH2OSO2Me | cyclopentyl |
| 932 | 2-Me Ph | CH2OCH2C(O)Ph | i-Bu |
| 933 | 2-Me Ph | CH2C(O)Me | 3-OMe Phenyl |
| 934 | 2-Me Ph | CH2C(O)Ph | 3-Cl phenyl |
| 935 | 2-Thienyl | CH2CO2(cyclopentyl) | 3-Me Phenyl |
| 936 | 2-Thienyl | CH2CO2(t-Bu) | t-Bu |
| 937 | 2-Thienyl | CH2CO2(cyclobutyl) | cyclopentyl |
| 938 | 2-Thienyl | CH2Ph | i-Bu |
| 939 | 2-Thienyl | CH2SO2Ph | 3-OMe Phenyl |
| 940 | 2-Thienyl | CH2OSO2(4-MePh) | 3-Cl phenyl |
| 941 | 2-Thienyl | CH2OSO2Me | 3-Me Phenyl |
| 942 | 2-Thienyl | CH2OCH2C(O)Ph | t-Bu |
| 943 | 2-Thienyl | CH2C(O)Me | cyclopentyl |
| 944 | 2-Thienyl | CH2C(O)Ph | i-Bu |
| 945 | Ph | CH2CO2(cyclopentyl) | 3-Cl phenyl |
| 946 | Ph | CH2CO2(t-Bu) | 3-Me Phenyl |
| 947 | Ph | CH2CO2(cyclobutyl) | t-Bu |

TABLE 4-continued

| CN | R1 | R2 | R3 |
|---|---|---|---|
| 948 | Ph | CH2Ph | cyclopentyl |
| 949 | Ph | CH2SO2Ph | i-Bu |
| 950 | Ph | CH2OSO2(4-MePh) | 3-OMe Phenyl |
| 951 | Ph | CH2OSO2Me | 3-Cl phenyl |
| 952 | Ph | CH2OCH2C(O)Ph | 3-Me Phenyl |
| 953 | Ph | CH2C(O)Me | t-Bu |
| 954 | Ph | CH2C(O)Ph | cyclopentyl |
| 955 | 2-Cl Ph | CH2CO2(cyclopentyl) | i-Bu |
| 956 | 2-Cl Ph | CH2CO2(t-Bu) | 3-OMe Phenyl |
| 957 | 2-Cl Ph | CH2CO2(cyclobutyl) | 3-Cl phenyl |
| 958 | 2-Cl Ph | CH2Ph | 3-Me Phenyl |
| 959 | 2-Cl Ph | CH2SO2Ph | t-Bu |
| 960 | 2-Cl Ph | CH2OSO2(4-MePh) | cyclopentyl |
| 961 | 2-Cl Ph | CH2OSO2Me | i-Bu |
| 962 | 2-Cl Ph | CH2OCH2C(O)Ph | 3-OMe Phenyl |
| 963 | 2-Cl Ph | CH2C(O)Me | 3-Cl phenyl |
| 964 | 2-Cl Ph | CH2C(O)Ph | 3-Me Phenyl |
| 965 | 2-F Ph | CH2CO2(cyclopentyl) | t-Bu |
| 966 | 2-F Ph | CH2CO2(t-Bu) | cyclopentyl |
| 967 | 2-F Ph | CH2CO2(cyclobutyl) | i-Bu |
| 968 | 2-F Ph | CH2Ph | 3-OMe Phenyl |
| 969 | 2-F Ph | CH2SO2Ph | 3-Cl phenyl |
| 970 | 2-F Ph | CH2OSO2(4-MePh) | 3-Me Phenyl |
| 971 | 2-F Ph | CH2OSO2Me | t-Bu |
| 972 | 2-F Ph | CH2OCH2C(O)Ph | cyclopentyl |
| 973 | 2-F Ph | CH2C(O)Me | i-Bu |
| 974 | 2-F Ph | CH2C(O)Ph | 3-OMe Phenyl |
| 975 | 2-Br Ph | CH2CO2(cyclopentyl) | 3-Cl phenyl |
| 976 | 2-Br Ph | CH2CO2(t-Bu) | 3-Me Phenyl |
| 977 | 2-Br Ph | CH2CO2(cyclobutyl) | t-Bu |
| 978 | 2-Br Ph | CH2Ph | cyclopentyl |
| 979 | 2-Br Ph | CH2SO2Ph | i-Bu |
| 980 | 2-Br Ph | CH2OSO2(4-MePh) | 3-OMe Phenyl |
| 981 | 2-Br Ph | CH2OSO2Me | 3-Cl phenyl |
| 982 | 2-Br Ph | CH2OCH2C(O)Ph | 3-Me Phenyl |
| 983 | 2-Br Ph | CH2C(O)Me | t-Bu |
| 984 | 2-Br Ph | CH2C(O)Ph | cyclopentyl |
| 985 | 2-Me Ph | CH2CO2(cyclopentyl) | i-Bu |
| 986 | 2-Me Ph | CH2CO2(t-Bu) | 3-OMe Phenyl |
| 987 | 2-Me Ph | CH2CO2(cyclobutyl) | 3-Cl phenyl |
| 988 | 2-Me Ph | CH2Ph | 3-Me Phenyl |
| 989 | 2-Me Ph | CH2SO2Ph | t-Bu |
| 990 | 2-Me Ph | CH2OSO2(4-MePh) | cyclopentyl |
| 991 | 2-Me Ph | CH2OSO2Me | i-Bu |
| 992 | 2-Me Ph | CH2OCH2C(O)Ph | 3-OMe Phenyl |
| 993 | 2-Me Ph | CH2C(O)Me | 3-Cl phenyl |
| 994 | 2-Me Ph | CH2C(O)Ph | 3-Me Phenyl |
| 995 | 2-Thienyl | CH2CO2(cyclopentyl) | t-Bu |
| 996 | 2-Thienyl | CH2CO2(t-Bu) | cyclopentyl |
| 997 | 2-Thienyl | CH2CO2(cyclobutyl) | i-Bu |
| 998 | 2-Thienyl | CH2Ph | 3-OMe Phenyl |
| 999 | 2-Thienyl | CH2SO2Ph | 3-Cl phenyl |
| 1000 | 2-Thienyl | CH2OSO2(4-MePh) | 3-Me Phenyl |
| 1001 | 2-Thienyl | CH2OSO2Me | t-Bu |
| 1002 | 2-Thienyl | CH2OCH2C(O)Ph | cyclopentyl |
| 1003 | 2-Thienyl | CH2C(O)Me | i-Bu |
| 1004 | 2-Thienyl | CH2C(O)Ph | 3-OMe Phenyl |
| 1005 | Ph | CH2CO2(cyclopentyl) | 3-Me Phenyl |
| 1006 | Ph | CH2CO2(t-Bu) | t-Bu |
| 1007 | Ph | CH2CO2(cyclobutyl) | cyclopentyl |
| 1008 | Ph | CH2Ph | i-Bu |
| 1009 | Ph | CH2SO2Ph | 3-OMe Phenyl |
| 1010 | Ph | CH2OSO2(4-MePh) | 3-Cl phenyl |
| 1011 | Ph | CH2OSO2Me | 3-Me Phenyl |
| 1012 | Ph | CH2OCH2C(O)Ph | t-Bu |
| 1013 | Ph | CH2C(O)Me | cyclopentyl |
| 1014 | Ph | CH2C(O)Ph | i-Bu |
| 1015 | 2-Cl Ph | CH2CO2(cyclopentyl) | 3-OMe Phenyl |
| 1016 | 2-Cl Ph | CH2CO2(t-Bu) | 3-Cl phenyl |
| 1017 | 2-Cl Ph | CH2CO2(cyclobutyl) | 3-Me Phenyl |
| 1018 | 2-Cl Ph | CH2Ph | t-Bu |
| 1019 | 2-Cl Ph | CH2SO2Ph | cyclopentyl |
| 1020 | 2-Cl Ph | CH2OSO2(4-MePh) | i-Bu |
| 1021 | 2-Cl Ph | CH2OSO2Me | 3-OMe Phenyl |
| 1022 | 2-Cl Ph | CH2OCH2C(O)Ph | 3-Cl phenyl |
| 1023 | 2-Cl Ph | CH2C(O)Me | 3-Me Phenyl |
| 1024 | 2-Cl Ph | CH2C(O)Ph | t-Bu |
| 1025 | 2-F Ph | CH2CO2(cyclopentyl) | cyclopentyl |
| 1026 | 2-F Ph | CH2CO2(t-Bu) | i-Bu |
| 1027 | 2-F Ph | CH2CO2(cyclobutyl) | 3-OMe Phenyl |
| 1028 | 2-F Ph | CH2Ph | 3-Cl phenyl |
| 1029 | 2-F Ph | CH2SO2Ph | 3-Me Phenyl |
| 1030 | 2-F Ph | CH2OSO2(4-MePh) | t-Bu |
| 1031 | 2-F Ph | CH2OSO2Me | cyclopentyl |
| 1032 | 2-F Ph | CH2OCH2C(O)Ph | i-Bu |
| 1033 | 2-F Ph | CH2C(O)Me | 3-OMe Phenyl |
| 1034 | 2-F Ph | CH2C(O)Ph | 3-Cl phenyl |
| 1035 | 2-Br Ph | CH2CO2(cyclopentyl) | 3-Me Phenyl |
| 1036 | 2-Br Ph | CH2CO2(t-Bu) | t-Bu |
| 1037 | 2-Br Ph | CH2CO2(cyclobutyl) | cyclopentyl |
| 1038 | 2-Br Ph | CH2Ph | i-Bu |
| 1039 | 2-Br Ph | CH2SO2Ph | 3-OMe Phenyl |
| 1040 | 2-Br Ph | CH2OSO2(4-MePh) | 3-Cl phenyl |
| 1041 | 2-Br Ph | CH2OSO2Me | 3-Me Phenyl |
| 1042 | 2-Br Ph | CH2OCH2C(O)Ph | t-Bu |
| 1043 | 2-Br Ph | CH2C(O)Me | cyclopentyl |
| 1044 | 2-Br Ph | CH2C(O)Ph | i-Bu |
| 1045 | 2-Me Ph | CH2CO2(cyclopentyl) | 3-OMe Phenyl |
| 1046 | 2-Me Ph | CH2CO2(t-Bu) | 3-Cl phenyl |
| 1047 | 2-Me Ph | CH2CO2(cyclobutyl) | 3-Me Phenyl |
| 1048 | 2-Me Ph | CH2Ph | t-Bu |
| 1049 | 2-Me Ph | CH2SO2Ph | cyclopentyl |
| 1050 | 2-Me Ph | CH2OSO2(4-MePh) | i-Bu |
| 1051 | 2-Me Ph | CH2OSO2Me | 3-OMe Phenyl |
| 1052 | 2-Me Ph | CH2OCH2C(O)Ph | 3-Cl phenyl |
| 1053 | 2-Me Ph | CH2C(O)Me | 3-Me Phenyl |
| 1054 | 2-Me Ph | CH2C(O)Ph | t-Bu |
| 1055 | 2-Thienyl | CH2CO2(cyclopentyl) | cyclopentyl |
| 1056 | 2-Thienyl | CH2CO2(t-Bu) | i-Bu |
| 1057 | 2-Thienyl | CH2CO2(cyclobutyl) | 3-OMe Phenyl |
| 1058 | 2-Thienyl | CH2Ph | 3-Cl phenyl |
| 1059 | 2-Thienyl | CH2SO2Ph | 3-Me Phenyl |
| 1060 | 2-Thienyl | CH2OSO2(4-MePh) | t-Bu |
| 1061 | 2-Thienyl | CH2OSO2Me | cyclopentyl |
| 1062 | 2-Thienyl | CH2OCH2C(O)Ph | i-Bu |
| 1063 | 2-Thienyl | CH2C(O)Me | 3-OMe Phenyl |
| 1064 | 2-Thienyl | CH2C(O)Ph | 3-Cl phenyl |

TABLE 5

| CN | R1 | R2 | R3 |
|---|---|---|---|
| 1065 | Ph | Et | 1-CO2Et-cyclopent-3-en-1-yl |
| 1066 | Ph | Me | CH2(1-Me-cyclopropyl) |
| 1067 | Ph | Me | CH(Me)(2-Me-cyclopropyl) |
| 1068 | Ph | Me | bicyclo[3.1.0]hexan-1-yl |
| 1069 | Ph | Me | 1-Me-2-methylene-cyclopent-1-yl |
| 1070 | Ph | Me | bicyclo[4.1.0]heptan-2-yl |
| 1071 | Ph | Me | spiro[2.4]heptan-4-yl |
| 1072 | Ph | Me | 2-methylene-cyclopent-1-yl |
| 1073 | Ph | Me | 5-Me-2-methylene-cyclopent-1-yl |
| 1074 | Ph | Me | CH2-(2-Me-cyclopropyl) |
| 1075 | Ph | Et | 2-methylene-cyclopent-1-yl |
| 1076 | Ph | Me | 3-methylene-cyclopent-1-yl |
| 1077 | Ph | Me | endo bicyclo[2.2.1]hept-5-en-2-yl |
| 1078 | Ph | Me | exo bicyclo[2.2.1]hept-5-en-2-yl |
| 1079 | Ph | Me | endo bicyclo[2.2.1]hept-2-yl |
| 1080 | Ph | Me | exo bicyclo[2.2.1]hept-2-yl |
| 1081 | Ph | Me | CH2CH2SPh |
| 1082 | Ph | Me | CH2CH2NH(3-PhO-Ph) |
| 1083 | Ph | Me | CH2CH2SEt |
| 1084 | Ph | Me | CH2CH2SCH2CF3 |
| 1085 | Ph | Me | CH2CH2S-cyclohexyl |
| 1086 | Ph | Me | CH2CH2SCH2Ph |
| 1087 | Ph | Me | CH2CH2SCH2(2-furyl) |
| 1088 | Ph | Me | CH2CH2S(2-pyridyl) |
| 1089 | Ph | Me | CH2CH2S(1-naphthyl) |

Compounds of formula (I) above may be prepared by the application or adaptation of known methods (i.e. methods heretofore used or described in the literature). It is to be understood that in the descriptions of the following processes the sequences may be performed in different orders and that suitable protecting groups may be required to achieve the compounds sought.

According to a feature of the present invention compounds of formula (I) wherein Q represents a —C(=O)— group and $R^1$, $R^2$, $R^3$, $R^4$ and $R^5$ are as defined above, may be prepared by the oxidation of the corresponding compound of formula (II):

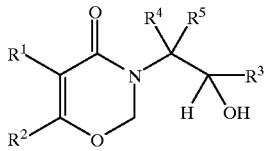
(II)

wherein $R^1$, $R^2$, $R^3$, $R^4$ and $R^5$ are as defined above. The oxidation is generally carried out with a suitable oxidising agent, e.g. chromic acid or pyridinium chlorochromate. The reaction may be performed in a suitable solvent e.g. ether or dichloromethane and at a temperature from 0° C. to the reflux temperature of the solvent.

According to a further feature of the present invention compounds of formula (Ie) may be prepared by the reaction of a compound of formula (III):

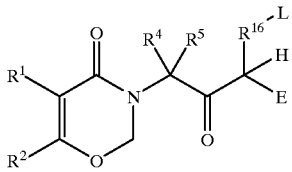
(III)

wherein L represents a leaving group such as halogen (preferably chlorine, bromine or iodine) or tosyloxy which is generally located at the terminal carbon of the group $R^{16}$; with a base such as sodium hydride in an inert solvent such as N,N-dimethylformamide and at a temperature of from −20° C. to 100° C.

According to a further feature of the present invention compounds of formula (Ie) wherein $R^1$, $R^2$, $R^4$ and $R^5$ are as defined above, $R^{16}$ is a C2–C7 alkylene or C3–C7 alkenylene group which is substituted by one or more halogen or $R^7$ groups and E is replaced by a hydrogen atom, may be prepared by the hydrolysis or hydrogenolysis and decarboxylation of the corresponding compound in which E represents $CO_2R^7$ or $CO_2CH_2R^6$ respectively. The hydrolysis may be performed using either basic or preferably acidic conditions (when $R^7$ is preferably tert-butyl) such as 4-toluenesulphonic acid in a solvent such as toluene at a temperature from 0° C. to 100° C. Preferably the reaction is carried out by hydrogenolysis using for example using hydrogen and an inert solvent such as ethanol in the presence of a catalyst such as palladium on carbon generally at about 20° C., and the decarboxylation completed by reaction with a base such as triethylamine at a temperature of from 20° C. to 60° C.

According to a further feature of the present invention compounds of formula (I) wherein Q represents a —C(=O)— group and $R^1$, $R^2$, $R^3$, $R^4$ and $R^5$ are as defined above, may be prepared by the reaction of a compound of formula (IV):

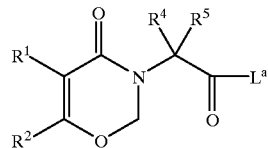
(IV)

wherein $L^a$ represents a leaving group such as chlorine or imidazole with an organometallic reagent of formula (V):

$$R^3—M \tag{V}$$

such as an organolithium or a Grignard reagent wherein M represents a lithium atom or a magnesium halide preferably bromide. The reaction is generally performed in an inert solvent such as ether or tetrahydrofuran at a temperature from −80° C. to 20° C.

According to a further feature of the present invention compounds of formula (I) wherein $R^3$ represents the group —CH($R^{17}$)$R^{13a}$ of formula (Ig):

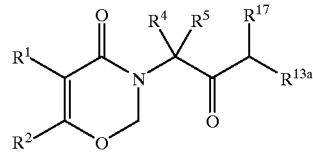
(Ig)

wherein $R^{17}$ represents C1–C5 alkyl or haloalkyl optionally substituted by $R^{13a}$ or $R^{14d}$; or C2–C5 alkenyl or haloalkenyl which are optionally substituted by $R^{13a}$ or a group selected from $R^6$, $R^{15a}$ and $R^{15}$; or C2–C5 alkynyl optionally substituted by $R^{13a}$; and $R^1$, $R^2$, $R^4$, $R^5$, $R^6$, $R^{13a}$, $R^{14d}$, $R^{15a}$ and $R^{15}$ are as defined above, may be prepared by the reaction of a compound of formula (I) wherein $R^3$ represents the group —$CH_2R^{13a}$ of formula (Ih):

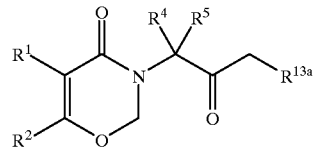
(Ih)

wherein $R^{13a}$ is as defined above, with a compound of formula (VI):

$$R^{17}—L \tag{VI}$$

wherein L represents a leaving group such as halogen (preferably chlorine, bromine or iodine) or tosyloxy. The reaction is generally performed in the presence of a base such as sodium hydride in an inert solvent such as N,N-dimethylformamide and at a temperature of from −20° C. to 100° C.

According to a further feature of the present invention compounds of formula (Ih) wherein $R^1$, $R^2$, $R^4$ and $R^5$ are as defined above, $R^{13a}$ represents $CO_2R^7$ and $R^7$ is as defined above, may be prepared by the reaction of a compound of formula (IV) wherein $L^a$ represents a leaving group such as chlorine or preferably imidazole, with a compound of formula (VII):

$$R^7O_2CCH_2CO_2H \qquad (VII)$$

wherein $R^7$ is as defined above. The reaction is performed using the metal salt (preferably the magnesium enolate salt) of (VII) in an inert solvent such as tetrahydrofuran at a temperature from 0° C. to reflux. (The magnesium salt of (VII) may be formed by reaction with magnesium in an inert solvent such as tetrahydrofuran at a temperature from −80° C. to 20° C.).

According to a further feature of the present invention compounds of formula (I) in which $R^2$ is lower alkyl or lower haloalkyl substituted by CHO, $COR^7$ or $COR^6$ may be prepared by oxidation of the corresponding compounds of formula (I) in which $R^{11a}$ is replaced by $CH_2OH$, CH(OH)$R^7$ or CH(OH)$R^6$ respectively, using for example pyridinium chlorochromate in dichloromethane at 0° C. to the reflux temperature.

According to a further feature of the present invention compounds of formula (I) wherein $R^2$ represents lower alkyl or lower haloalkyl substituted by $SR^6$ or $SR^{15}$ wherein $R^6$ and $R^{15}$ are as defined above, may be prepared by the reaction of the corresponding compound of formula (I) in which $R^{11a}$ is replaced by a leaving group, preferably chloro or bromo, with a thiol of formula $R^6SH$ or $R^{15}SH$ or an alkali metal salt (preferably lithium or sodium salt) thereof. The reaction is generally performed in an inert solvent e.g. N,N-dimethylformamide at a temperature from 0 to 60° C.

According to a further feature of the present invention compounds of formula (I) wherein $R^2$ represents lower alkyl or lower haloalkyl substituted by OC(O)$R^6$, wherein $R^6$ is as defined above may be prepared by reaction of the corresponding compound of formula (I) in which the OC(O)$R^6$ group is replaced by a leaving group, with a salt of formula $R^6$—$CO_2$—$M_1^+$, wherein $M_1$ represents sodium or potassium. The leaving group is preferably chlorine or bromine. The reaction is typically performed in an inert solvent preferably N,N-dimethylformamide at a temperature from ambient to 120° C.

According to a further feature of the present invention compounds of formula (I) in which $R^2$ represents lower alkyl or lower haloalkyl substituted by $R^{11a}$ wherein $R^{11a}$ represents $CO_2R^7$, $CO_2R^{15}$ or $CO_2R^6$ may be prepared by esterification of the corresponding compounds of formula (I) in which $R^{11a}$ is $CO_2H$, to replace the hydrogen atom with a group $R^7$, $R^{15}$ or $R^6$. The reaction is preferably performed with an alcohol of formula $R^7OH$, $R^{15}OH$ or phenol $R^6OH$ and diethylazodicarboxylate in an inert solvent e.g. ether at a temperature from 0° C. to the reflux temperature of the solvent. Alternatively, the conversion may be performed by chlorination of the corresponding compound of formula (I) in which $R^{11a}$ is $CO_2H$ using for example oxalyl chloride, in an inert solvent, e.g. dichloromethane or 1,2-dichlorethane, optionally in the presence of a catalyst such as N,N-dimethylformamide at a temperature from 20° C. to the reflux temperature of the mixture to give the corresponding acid chloride, which is subsequently reacted with an alcohol of formula $R^7OH$ or $R^{15}OH$ or phenol $R^6OH$ in an inert solvent e.g. tetrahydrofuran at a temperature from 0° C. to the reflux temperature of the solvent.

According to a further feature of the present invention, compounds of formula (I) in which $R^2$ represents lower alkyl or lower haloalkyl substituted by $R^{11a}$ in which $R^{11a}$ is $CONR^9R^{10}$, $CONHR^6$ or $CONR^6R^7$ wherein $R^6$, $R^7$, $R^9$ and $R^{10}$ are as defined above may be prepared by reaction of the corresponding compound of formula (I) in which $R^{11a}$ is $CO_2H$ with a chlorinating agent to produce the carboxylic acid chloride by the method described above, which is subsequently reacted with an amine of formula $R^9R^{10}NH$, $R^6NH_2$ or $R^6R^7NH$, wherein $R^6$, $R^7$, $R^9$ and $R^{10}$ are as defined above in an inert solvent e.g. ether or tetrahydrofuran at a temperature from 0° C. to the reflux temperature of the mixture.

According to a further feature of the present invention, compounds of formula (I) in which $R^2$ represents lower alkyl or lower haloalkyl substituted by $R^{11a}$ in which $R^{11a}$ is $CO_2H$, may be prepared by oxidising the corresponding compound of formula (I) in which $R^2$ is CHO, which may be achieved by procedures reported in R.C. Larock in Comprehensive Organic Transformations p.838, e.g. by reaction with pyridinium dichromate in N,N-dimethylformamide at a temperature from 0 to 6° C.

According to a further feature of the present invention, compounds of formula (I) in which $R^2$ represents lower alkyl or lower haloalkyl substituted by $R^{11a}$ in which $R^{11a}$ is $OSO_2R^6$ or $OSO_2R^7$, may be prepared by the reaction of the corresponding compound of formula (I) in which $R^{11a}$ is replaced by hydroxy with a sulphonating agent of formula $R^6SO_2Y$ or $R^7SO_2Y$ wherein Y is a leaving group preferably chloro. The reaction is generally performed in the presence of a base for example pyridine in a solvent such as ether at 0 to 60° C.

According to a further feature of the present invention, compounds of formula (I) in which $R^2$ represents lower alkyl or lower haloalkyl substituted by $R^{11a}$ in which $R^{11a}$ is $OR^6$, may be prepared by the reaction of the corresponding compound of formula (I) in which $R^{11a}$ is replaced by a leaving group preferably chloro or bromo, with a phenol $R^6OH$ in the presence of a base, generally an alkali metal carbonate such as potassium carbonate in acetone, or an alkoxide for example sodium ethoxide in tetrahydrofuran at OOC to the reflux temperature.

According to a further feature of the present invention, compounds of formula (I) in which $R^2$ represents lower alkyl or lower haloalkyl substituted by $R^{11a}$ in which $R^{11a}$ is $OCH_2COR^6$, may be prepared by the reaction of the corresponding compound of formula (I) in which $R^{11a}$ is replaced by hydroxy, with a halide of formula $R^6COCH_2Z$ wherein Z is preferably chloro or bromo, generally in the presence of a base such as pyridine in tetrahydrofuran at 0° C. to the reflux temperature.

According to a further feature of the present invention, compounds of formula (I) in which $R^2$ is $CH_2CO_2H$, may be prepared by the reaction of the corresponding compound of formula (I) in which $R^2$ is replaced by methyl, with a strong base for example lithium bis(trimethylsilyl)amide in a solvent such as tetrahydrofuran at −70° C. to 20° C. followed by addition of carbon dioxide.

According to a further feature of the present invention, compounds of formula (I) in which $R^2$ is $CH_2CO_2R^7$, $CH_2CO_2R^6$ or $CH_2CO_2R^{15}$ may be prepared by the reaction of the corresponding compounds of formula (I) in which $R^2$ is replaced by methyl, with a strong base for example lithium bis(trimethylsilyl)amide in a solvent such as tetrahydrofuran at −70° C. to 20° C. followed by addition of a chloroformate of formula $ClCO_2R^7$, $ClCO_2R^6$ or $ClCO_2R^{15}$. This process may also be used to give the bis-substituted products in which $R^2$ is $CH(CO_2R^7)_2$, $CH(CO_2R^6)_2$ or $CH(CO_2R^{15})_2$.

According to a further feature of the present invention, compounds of formula (I) in which $R^3$ is a bicycloalkene may be prepared by the Diels Alder addition of the corresponding compound in which $R^3$ is vinyl with a cycloalkadiene, generally cyclopentadiene. The reaction may be performed in a solvent such as toluene preferably at the reflux temperature.

According to a further feature of the present invention, compounds of formula (I) in which $R^3$ is a bicycloalkane may be prepared by the reduction of the corresponding compound in which $R^3$ is a bicycloalkene. The reduction is generally performed by catalytic hydrogenation using a catalyst such as palladium on carbon in a solvent such as ethanol at a temperature of 20° C. to the reflux temperature.

According to a further feature of the present invention, compounds of formula (I) in which $R^3$ is lower alkyl substituted by a substituted cycloalkyl ring containing from three to six carbon atoms; or cycloalkyl containing from three to eight carbon atoms substituted by an exocyclic optionally halogenated alkylidene group; or a bicycloalkane, bicyclo-alkene, spiro-alkane or spiro-alkene; may be prepared by the reaction of the corresponding alkene, alkylidene or cycloalkene compound respectively with a dihaloalkane, generally a dibromoalkane or diiodoalkane in the presence of an organometallic reagent such as diethyl zinc or zinc—copper couple, in a solvent such as dichloromethane at a temperature of from 20° C. to the reflux temperature.

According to a further feature of the present invention compounds of formula (I) wherein Q represents —C(OR$^{14}$)(OR$^{14a}$)—)— may be prepared by the reaction of a compound of formula (I) wherein Q represents —C(=O)—, with an alcohol of formula $R^{14}$—OH or a diol of formula HO—$R^{14e}$—OH wherein $R^{14e}$ represents a C2 or C3 alkylene chain optionally substituted by one or more lower alkyl groups. The reaction is generally performed in the presence of an acid catalyst e.g. 4-toluenesulphonic acid and an inert solvent e.g. toluene and at a temperature from 60° C. to the reflux temperature of the solvent. The reaction is facilitated by removal of the water formed preferably by azeotropic distillation or in the presence of a dehydrating agent e.g. molecular sieve.

According to a further feature of the present invention compounds of formula (I) in which m, p, q, r, t or u represent one or two may be prepared by the oxidation of the sulphur atom of the corresponding compounds in which m, p, q, r, t or u represent zero or one. The oxidation of the sulphur atom is generally carried out using for example 3-chloroperbenzoic acid in an inert solvent such as dichloromethane at a temperature from 40° C. to room temperature.

Intermediates of formula (II) may be prepared by the reaction of an aldehyde of formula (VIII):

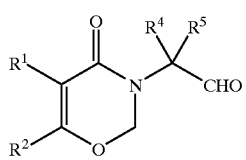

(VIII)

wherein $R^1$, $R^2$, $R^4$ and $R^5$ are as defined above, with an organometallic compound of formula $R^3$—M, wherein $R^3$ is as defined above and M represents a metallic group, preferably a magnesium bromide group or a lithium atom. The reaction is generally performed in an inert solvent e.g. ether or tetrahydrofuran and at a temperature from −78° C. to the reflux temperature of the solvent.

Compounds of formula (II) are novel and as such form a further feature of the invention.

Intermediates of formula (III) may be prepared by the alkylation or alkenylation of the corresponding compound of formula (IX):

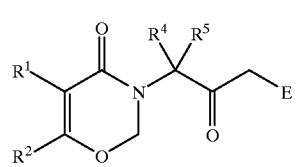

(IX)

wherein $R^1$, $R^2$, $R^4$, $R^5$ and E are as defined above, with a compound of formula (X):

$L^1$—$R^{16}$ L  (X)

wherein $R^{16}$ and L are as defined above, and $L^1$ represents a leaving group such as halogen or tosyloxy (generally the groups L and $L^1$ are the same). The reaction is generally performed using a base for example an alkali metal carbonate such as potassium carbonate, or a metal hydride such as sodium hydride, in an inert solvent such as N,N-dimethylformamide or dimethylsulphoxide at a temperature of from −20° C. to 100° C.

Intermediates of formula (IX) wherein E represents —CO$_2$R$^7$ and $R^7$ is as defined above may be prepared by the reaction of a compound of formula (IV) with a compound of formula (VII) wherein $R^7$ is as defined above. The reaction is performed using the metal salt (preferably the magnesium enolate salt) of (VII) in an inert solvent such as tetrahydrofuran at a temperature from 0° C. to reflux. (The magnesium salt of (VII) may be formed by reaction with magnesium in an inert solvent such as tetrahydrofuran at a temperature from −80° C. to 20° C.).

Intermediates of formula (VIII) may be prepared by the reduction of an ester of formula (XI):

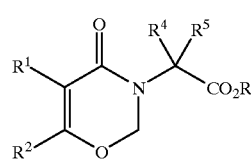

(XI)

wherein R represents a lower alkyl group, preferably ethyl. The reaction is generally performed using a suitable reducing agent, e.g. lithium aluminium hydride, in an inert solvent, e.g. tetrahydrofuran, at a temperature from −80° C. to 20° C.

Intermediates of formula (IV) wherein $L^a$ represents imidazole may be prepared by the reaction of a compound of formula (XI) wherein R is replaced by hydrogen with carbonyldiimidazole in a solvent such as tetrahydrofuran at a temperature of from −20° C. to 30° C.

Esters of formula (XI) wherein $R^1$ and $R^2$ are as defined above may be prepared by the reaction of a compound of formula (XII):

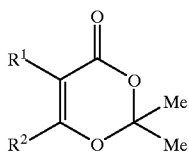

(XII)

with an imine of formula (XIII):

CH$_2$=N—C(R$^4$)(R$^5$)CO$_2$R         (XIII)

wherein R$^4$, R$^5$ and R are as defined above. The reaction is generally performed in the presence or absence of solvent and at a temperature from 90° C. to 200° C. or the boiling point of the solvent. The solvent when used is inert, for example xylene, and the acetone produced is preferably removed by distillation.

Intermediates of formula (I) in which R$^2$ is lower alkyl or lower haloalkyl substituted by R$^{11a}$ and R$^{11a}$ is replaced by —CH(OH)R$^7$ or —CH(OH)R$^6$ may be prepared by the reaction of the corresponding compounds of formula (I) in which R$^{11a}$ represents —CHO with a Grignard reagent of formula R$^7$Mg—X or R$^6$Mg—X wherein R$^7$ and R$^6$ are as defined above and X represents a bromine or iodine atom. The reaction may be performed in an inert solvent e.g. ether or tetrahydrofuran at a temperature from 20 to 60° C.

Intermediates of formula (I) in which R$^2$ is lower alkyl or lower haloalkyl substituted by R$^{11a}$ and R$^{11a}$ is replaced by —CH$_2$OH may be prepared by the hydrolysis of the corresponding compounds of formula (I) in which R$^{11a}$ is —CH(OCOR$^7$)— wherein R$^7$ is as defined above. Preferably R$^7$ is methyl, and the hydrolysis is performed using a base e.g. potassium carbonate in an aqueous alcohol solution at 0 to 50° C.

Compounds of formula (V), (VI), (VII), (X), (XII) and (XIII) are known or may be prepared by the application or adaptation of known methods.

Compounds of formula (I) above may be prepared by interconversion of other compounds of formula (I) and such conversions constitute further features of the present invention.

The following non-limiting Examples illustrate the invention. $^1$H-NMR spectra (shifts in ppm) were run in CDCl$_3$ unless otherwise stated.

EXAMPLE 1

Sodium hydride (40 mg of 60% oil dispersion) was added at 0° C. to a solution of ethyl 4-(2,3-dihydro-6-methyl-4-oxo-5-phenyl-4H-1,3-oxazin-3-yl)-2-(4'-iodobutyl)-4-methyl-3-oxo-pentanoate (0.25 g) in N,N-dimethylformamide, and stirred at 20° C. for 2 hours. The mixture was diluted (ether),washed (brine), dried (MgSO4) and evaporated. The residue was purified by column chromatography (ethyl acetate/hexane 1:3) to give ethyl 1-[2-(2,3-dihydro-6-methyl-4-oxo-5-phenyl-4H-1,3-oxazin-3-yl)-2-methylpropionyl]cyclopentylcarboxylate (Compound 1, 0.14 g), NMR 1.21(3H, t), 1.4–1.6(8H, m), 1.7–1.8(2H, m), 1.91(3H, s), 2.1–2.2(2H, m), 2.4–2.5(2H, m), 3.60(2H, s), 4.14(2H, q), 5.16(2H, s), 7.2–7.4(5H, m).

EXAMPLE 2

A mixture of ethyl 4-(2,3-dihydro-6-methyl-4-oxo-5-phenyl-1,3-oxazin-3-yl)-4-methyl-3-oxo-pentanoate (500 mg), N-bromosuccinimide(258 mg) and benzoyl peroxide (10 mg) was refluxed under a lamp whilst stirring in benzene for 10 minutes. After cooling, the solid was filtered, the filtrate evaporated and the residue purified by column chromatography (hexane/ethyl acetate 4:1) to give ethyl 2-bromo-4-(2,3-dihydro-6-methyl-4-oxo-5-phenyl-1,3-oxazin-3-yl)-4-methyl-3-oxo-pentanoate (Compound 190, 400 mg ) as a yellow gum, NMR 1.21(t,3H), 1.55(d,6H), 1.94(s,3H), 4.15(q,2H), 5.23(s,1H), 5.26(d—d,2H) and 7.21–7.37(m,5H).

By proceeding in a similar manner but using N-chlorosuccinimide the following compound was also obtained:

ethyl 2-chloro-4-(2,3-dihydro-6-methyl-4-oxo-5-phenyl-1,3-oxazin-3-yl)-4-methyl-3-oxo-pentanoate (Compound 191), NMR 1.21(t,3H), 1.57(d,6H), 1.94 (s,3H), 4.25(q,2H), 5.30(s,1H), 5.28(d—d,2H) and 7.22–7.37(m,5H).

EXAMPLE 3

Sodium hydride (60% in oil, 140 mg) was added to a stirred solution of ethyl 4-(2,3-dihydro-6-methyl-4-oxo-5-phenyl-1,3-oxazin-3-yl)-4-methyl-3-oxo-pentanoate (500 mg) in tetrahydrofuran and the mixture stirred at 20° C. for 1 hour. N-Fluoro-2,4,6-trimethylpyridinium triflate (1.0 g) was added and stirring continued at 20° C. for 12 hours. The mixture was poured into ice water, extracted (ethyl acetate), washed (2M hydrochloric acid) and brine, dried (magnesium sulphate), evaporated and purified by column chromatography (hexane/ethyl acetate 4:1) to give ethyl 2,2-difluoro-4-(2,3-dihydro-6-methyl-4-oxo-5-phenyl-1,3-oxazin-3-yl)-4-methyl-3-oxo-pentanoate (Compound 192, 0.20 g) as a white solid, NMR 1.14(t,3H), 1.56(s,6H), 1.94(s,3H), 4.09 (q,2H), 5.30(s,2H), 7.22–7.35(m,5H).

EXAMPLE 4

A suspension of magnesium turnings (100 mg) in methanol was stirred whilst a solution of t-butyl [4-(2,3-dihydro-6-methyl-4-oxo-5-phenyl-1,3-oxazin-3-yl)-4-methyl-3-oxo-pentanoate (1.40 g) in methanol was added. The mixture was heated at 60° C. for 1 hour, cooled and evaporated. Toluene was added and the mixture re-evaporated. The residue was redissolved in toluene and a solution of acetyl chloride (300 mg) added. The mixture was stirred at 20° C. for 1 day, then hydrochloric acid (2M) added and the stirring continued for another 1 hour. The organic phase was washed with hydrochloric acid (2M) then with water and dried (magnesium sulphate) 4-Toluene-sulphonic acid (50 mg) was added and the mixture stirred at 80° C. for 1 hour, cooled and washed in turn with saturated sodium bicarbonate solution and water, dried (magnesium sulphate) and evaporated to give 5-(2,3-dihydro-6-methyl-4-oxo-5-phenyl-1,3-oxazin-3-yl)-5-methyl-2,4-hexanedione (Compound 193, 0.15 g) as a brown gum, NMR 1.56(s,6H), 1.91(s,3H), 2.15(s,3H), 3.66 and 3.70(s,1H), 5.25(t,2H), 7.20–7.44(m,5H).

EXAMPLE 5

A mixture of ethyl 4-(2,3-dihydro-6-methyl-4-oxo-5-phenyl-4H-1,3-oxazin-3-yl)-4-methyl-3-oxo-pentanoate (0.5 g), 1,4-diiodobutane(0.23 ml) and potassium carbonate (1.0 g) was stirred in dimethylsulphoxide at 20° C. for 12 hours. The mixture was diluted (ether), washed (brine), dried (MgSO4), evaporated and the residue purified by column chromatography (ethyl acetate/hexane 1:3) to give ethyl 4-(2,3-dihydro-6-methyl-4-oxo-5-phenyl-4H-1,3-oxazin-3-yl)-2-(4'-iodobutyl)-4-methyl-3-oxo-pentanoate (Compound 194, 0.3 g), NMR 1.24(3H, t), 1.3–1.4(2H, m), 1.43((3H, s), 1.48(3H, s), 1.7–2.0(7H, m), 3.12(2H, t), 3.8–3.9(1H, m), 4.1–4.2(2H, m), 5.28(2H, d), 7.2–7.4(5H, m).

By proceeding in a similar manner the following compounds were also obtained:

ethyl 4-(2,3-dihydro-6-methyl-4-oxo-5-phenyl-4H-1,3-oxazin-3-yl)-2,4-dimethyl-3-oxo-pentanoate (Compound 195), NMR 1.23(3H, t), 1.39(3H, d), 1.47 (3H, s), 1.52(3H, s), 1.93(3H, s), 4.0–4.2(3H, m) 5.27 (2H, d), 7.2–7.4(5H, m); and ethyl 2-ethyl-4-(2,3-dihydro-6-methyl-4-oxo-5-phenyl-4H-1,3-oxazin-3-yl)-4-methyl-3-oxo-pentanoate (Compound 196), NMR 0.89(3H, t), 1.22(3H, t), 1.43 (3H, s), 1.49(3H, s), 1.8–2.1(5H, m), 3.7–3.8(1H, m), 4.0–4.2(2H, m), 5.27(2H, s), 7.2–7.5(5H, m).

EXAMPLE 6

Sodium hydride (67 mg of 60%) was added to a stirred solution of ethyl 4-(2,3-dihydro-6-methyl-4-oxo-5-phenyl-4H-1,3-oxazin-3-yl)-2,4-dimethyl-3-oxo-pentanoate (0.4 g) in N,N-dimethylformamide at 0° C. Iodomethane (0.1 ml) was added and stirring continued for 16 hours. Ether was added and the organic phase washed (brine), dried (magnesium sulphate), evaporated and the residue purified by column chromatography eluting with ethyl acetate/hexane (1:2) to give ethyl 4-(2,3-dihydro-6-methyl-4-oxo-5-phenyl-4H-1,3-oxazin-3-yl)-2,2,4-trimethyl-3-oxo-pentanoate (Compound 197, 0.3 g), NMR 1.21(3H, t), 1.47(6H, s), 1.52(6H, s), 1.92(3H, s), 4.13(2H, q), 5.16(2H, s), 7.2–7.4(5H, m).

By proceeding in a similar manner the following compounds were also obtained:

ethyl 2-ethyl-4-(2,3-dihydro-6-methyl-4-oxo-5-phenyl-4H-1,3-oxazin-3-yl)-2,4-dimethyl-3-oxo-pentanoate (Compound 198), NMR 0.83(3H, t), 1.22(3H, t), 1.42 (3H, s), 1.47(3H, s), 1.56(3H, s), 1.75–1.85(1H, m), 1.91(3H, s), 2.05–2.2(1H, m), 4.0–4.3(3H, m), 5.15 (2H, q), 7.2–7.4(5H, m); and ethyl 2,2-diethyl-4-(2,3-dihydro-6-methyl-4-oxo-5-phenyl-4H-1,3-oxazin-3-yl)-4-methyl-3-oxo-pentanoate (Compound 199), NMR 0.81(3H, t), 1.22 (3H, t), 1.47(6H, s), 1.53(6H, s), 1.8–1.95(5H, m), 2.0–2.2(2H, m), 4.16(2H, q), 5.16(2H, s), 7.2–7.4(5H, m).

EXAMPLE 7

Isopropyl magnesium bromide (0.7M solution in tetrahydrofuran) was added to a solution of monoethyl malonate(1.44 g) in tetrahydrofuran at 0° C. The mixture was stirred at 20° C. for 0.5 hour and at 40° C. for 0.5 hour. 2-(2,3-Dihydro-6-methyl-4-oxo-5-phenyl-4H-1,3-oxazin-3-yl)2-methylpropionic acid (2 g) and carbonyldiimidazole (1.42 g) was stirred in tetrahydrofuran for 8 hours and the resulting imidazolide solution then added to the above mixture at 0° C., stirred at 20° C. for 3 hours and refluxed for 2 hours. The mixture was diluted (ether), washed (5% hydrochloric acid), dried (MgSO4),evaporated and the residue purified by column chromatography (ethyl acetate/hexane 1:2) to give ethyl 4-(2,3-dihydro-6-methyl-4-oxo-5-phenyl-4H-1,3-oxazin-3-yl)-4-methyl-3-oxo-pentanoate (Compound 200, 1.4 g), NMR 1.25(3H, t), 1.47(6H, s), 1.94(3H, s), 3.60(2H, s), 4.15(2H, q), 5.26(2H, s), 7.2–7.4 (5H, m).

By proceeding in a similar manner the following compounds were also obtained:

methyl 4-(2,3-dihydro-6-methyl-4-oxo-5-phenyl-4H-1,3-oxazin-3-yl)-4-methyl-3-oxo-pentanoate (Compound 201), NMR 1.47(s,6H), 1.94(s,3H), 3.62(s), 3.70(s), 5.26(s,1H), 7.24–7.40(5H); and t-butyl 4-(2,3-dihydro-6-methyl-4-oxo-5-phenyl-1,3-oxazin-3-yl)-4-methyl-3-oxo-pentanoate (Compound 202), NMR 1.44(s,6H) 1.47(s,9H) 1.93(s,3H) 3.53(s, 2H) 5.26(s,2H) 7.22–7.40(m,5H).

EXAMPLE 8

A solution of 2-[4-(2,3-dihydro-6-methyl-4-oxo-5-phenyl-4H-1,3-oxazin-3-yl)-3-hydroxy-4-methylpentyl]-2,5,5-trimethyl-1,3-dioxane (0.80 g) in dichloromethane was added to a stirred mixture of pyridinium chlorochromate (0.62 g) and powdered molecular sieve (4A) in dichloromethane at 20° C. After 18 hours the mixture was purified by dry column chromatography on silica gel, eluting with hexane/ethyl acetate (3:1), to give 2-[4-(2,3-dihydro-6-methyl-4-oxo-5-phenyl-4H-1,3-oxazin-3-yl)-4-methylpentan-3-oyl]-2,5,5-trimethyl-1,3-dioxane (Compound 203, 0.40 g) as a colourless gum, NMR 0.9(2s, 6H), 1.3(s,3H), 1.4(s,6H), 1.9(s,3H), 2.0(m,2H), 2.7(m,2H), 3.4(s,4H), 5.3(s,2H), 7.3(m,5H).

By proceeding in a similar manner the following compound was also prepared:

2-[4-(2,3-dihydro-6-methyl-4-oxo-5-phenyl-4H-1,3-oxazin-3-yl)-4-methylpentan-3-oyl]-1,3-dioxolane (Compound 204), NMR 1.4(s,6H),1.9(s,3H), 1.9(m, 2H), 2.6(m,2H), 3.8(m,4H), 4.8(m,1H), 5.2(s,2H), 7.2 (m,5H).

EXAMPLE 9

A mixture of 2-[4-(2,3-dihydro-6-methyl-4-oxo-5-phenyl-4H-1,3-oxazin-3-yl)-4-methylpentan-3-oyl]-2-methyl-1,3-dioxane (0.35 g), trifluoroacetic acid (0.29 g) and water (0.10 g) in dichloromethane was heated under reflux for 5 hours. The solvent was evaporated by azeotroping with toluene and the residue purified by chromatography on silica gel eluting with hexane/ethyl acetate (3:1), to give 6-(2,3-dihydro-6-methyl-4-oxo-5-phenyl-4H-1,3-oxazin-3-yl)-6-methylheptan-2,5-dione (Compound 205, 0.18 g) as a colourless oil, NMR 1.5(s,6H), 1.9(s,3H), 2.2(s,3H), 2.8(m,4H), 5.3(s,2H), 7.3(m,5H).

EXAMPLE 10

A mixture of ethyl 4-(2,3-dihydro-6-methyl-5-phenyl-4-oxo4H-1,3-oxazin-3-yl)-4-methyl-3-oxo-pentanoate (0.50 g), 2-thiophenecarboxaldehyde(0.34 g), piperidine(0.43 g) and molecular sieve 4A in toluene was stirred at 80° C. for 7 hrs. The reaction solution was filtered (celite), evaporated and recrystallised (ethanol) to give ethyl 4-methyl-4-(2,3-dihydro-6-methyl-5-phenyl-4-oxo-4H-1,3-oxazin-3-yl)-2-(2-thienylmethylidene)-3-oxo-pentanoate (Compound 206, 0.20 g), NMR 1.23(t,3H) 1.58(s,6H) 1.94(s,3H) 4.29(q,2H) 5.19(s,2H) 7.05(7.20–7.37(6H) 7.48(1H) 8.05(s,1H). By proceeding in a similar manner the following compounds were also obtained:

ethyl 2-(cyclohexylmethylidene)-4-(2,3-dihydro-6-methyl-5-phenyl-4-oxo-4H-1,3-oxazin-3-yl)-4-methyl-3-oxo-pentanoate (Compound 207), NMR 1.26 (t), 1.1–1.3, 1.53(s,6H), 1.55–1.8, 1.92(s,3H), 2.22 (1H), 4.22(q,2H), 5.17(s,2H), 6.88(d,1H), 7.25–7.40 (5H);

methyl 2-(2-fluorobenzylidene)-4-(2,3-dihydro-6-methyl-5-phenyl-4-oxo-4H-1,3-oxazin-3-yl)-4- methyl-3-oxo-pentanoate (Compound 208),NMR 0.99 (q,3H), 1.61(s,6H), 1.90(s,3H), 4.18(q,2H), 5.20(s,2H), 7.0–7.4(8H), 7.55(1H), 7.98(s);

methyl 2-(2-furylmethylidene)-4-(2,3-dihydro-6-methyl-5-phenyl-4-oxo-4H-1,3-oxazin-3-yl)-4-methyl-3-oxo-pentanoate (Compound 209), NMR 1.23(t,3H), 1.57(s, 6H), 1.94(3H), 4.28(q,2H), 5.20(s,2H), 6.48(1H), 6.72 (1H), 7.207.33(5H), 7.45(1H), 7.66(s,1H);

ethyl 2-(3-chlorobenzylidene)-4-(2,3-dihydro-6-methyl-5-phenyl-4-oxo-4H-1,3-oxazin-3-yl)-4-methyl-3-oxo-pentanoate (Compound 210), NMR 1.03(t,3H) 1.59(s, 6H) 1.91(s,3H) 4.12(q,2H) 5.19(s,2H) 7.20–7.40(9H) 7.86(s,1H); and ethyl 2-(benzylidene)-4-(2,3-dihydro-6-methyl-5-phenyl-oxo-4H-1,3-oxazin-3-yl)-4-methyl-3-oxo-pentanoate (Compound 211), NMR 0.98(t,,3H) 1.60(s,6H) 1.90(s, 3H) 4.10(q,2H) 5.19(s,2H) 7.20–7.40(10H) 7.95(s,H).

EXAMPLE 11

A mixture of 6-bromo-2-(2,3-dihydro-6-methyl-4-oxo-5-phenyl-4H-1,3-oxazin-3-yl)-2-methylheptan-3-one (1.04 g), sodium acetate (0.43 g) and water (0.10 g) in N,N-dimethylformamide was heated at 70° C. for 2 hours. Water was added and the mixture extracted (dichloromethane) and the organic phase dried (magnesium sulphate) and evaporated. The residue was purified by chromatography on silica gel eluting with hexane/ethyl acetate (3:1), to give 2-(2,3-dihydro-6-methyl-4-oxo-5-phenyl-4H-1,3-oxazin-3-yl)-2-methyl-3-oxo-heptan-6-ol (Compound 212, 0.22 g) as a brown gum, NMR 1.2(d,3H), 1.4(2s,6H), 1.6(m,1H), 1.9(m, 2H), 1.9(s,3H), 2.5(m,1H), 2.8(m,1H), 3.8(m,1H), 5.3(m, 2H), 7.3(m,5H).

EXAMPLE 12

A solution of 2-(2,3-dihydro-6-methyl-4-oxo-5-phenyl-4H-1,3-oxazin-3-yl)-2-methyl-1-(3-vinylphenyl)propan-1-ol) (0.28 g) in dichloromethane was added to a stirred mixture of pyridinium chlorochromate (0.38 g) and powdered molecular sieve (4A) in dichloromethane at 20° C. After 3 hours the mixture was purified by dry column chromatography on silica gel, eluting with hexane, increasing the polarity to hexane/ethyl acetate (1:1), to give 2-(2, 3-dihydro-6-methyl-4-oxo-5-phenyl-4H-1,3-oxazin-3-yl)-2-methyl-1-(3-vinylphenyl)propan-1-one (Compound 444, 0.05 g) as a white solid, NMR 1.6 (s,6H), 1.8 (s,3H), 5.2 (d,1H), 5.3 (s,2H), 5.7 (d,1H), 6.6 (m,1H), 6.9 (m,2H), 7.2 (m,5H), 7.4 (d,1H), 7.8 (d,1H), 8.0 (s,1H).

By proceeding in a similar manner the following compound of formula (I) was prepared:

1-(2,2-difluoro-1,3-benzodioxol-5-yl)-2-(2,3-dihydro-6-methyl-4-oxo-5-phenyl-4H-1,3-oxazin-3-yl)-2-methylpropan-1-one (Compound 445), NMR 1.5 (s,6H), 1.8 (s,3H), 5.3 (s,2H), 6.9 (m,3H), 7.2 (m,3H), 7.7 (s,1H), 7.8 (d,1H).

EXAMPLE 13

Tetrapropylammonium perruthenate (0.014 g) and powdered molecular sieve (4A) were added to a stirred solution 2-(2,3-dihydro-6-methyl-4-oxo-5-phenyl-4H-1,3-oxazin-3-yl)-1-(2-fluoro-4-biphenyl)-2-methylpropan- 1-ol (0.33 g) and 4-methylmorpholine N-oxide (0.14 g) in dichloromethane at 20° C. After 1 hour, the mixture was purified by dry column chromatography on silica gel, eluting with dichloromethane, to give after trituration with hexane, 2-(2, 3-dihydro-6-methyl-4-oxo-5-phenyl-4H-1,3-oxazin-3-yl)-1-(2-fluoro-4-biphenyl)-2-methylpropan-1-one (Compound 446, 0.065 g), m.p. 127–129° C.

EXAMPLE 14

Oxalyl chloride (0.35 g) was added to a stirred mixture of dimethylsulphoxide (0.59 ml) in dichloromethane at −60° C. After 10 minutes, 1-(4-biphenyl)-2-(2,3-dihydro-6-methyl-4-oxo-5-phenyl-4H-1,3-oxazin-3-yl)-2-methylpropan-1-ol (0.11 g) was added, followed after 10 minutes by triethylamine (0.18 ml). The mixture was warmed to 20° C., poured onto water and the organic phase washed (water), dried (magnesium sulphate) and evaporated. Purification by dry column chromatography on silica gel, eluting with dichloromethane, increasing the polarity to dichloromethane/ethyl acetate (10:1), gave 1-(4-biphenyl)-2-(2,3-dihydro-6-methyl-4-oxo-5-phenyl-4H-1,3-oxazin-3-yl)-2-methylpropan-1-one (Compound 447, 0.05 g), NMR 1.6 (s,6H), 1.8 (s,3H), 5.4 (s,2H), 6.9 (m,2H), 7.1 (m,3H), 7.3 (m,3H), 7.5 (m,4H), 8.0 (d,2H).

By proceeding in a similar manner the following compounds of formula (I) were prepared:

2-(2,3-dihydro-6-methyl-4-oxo-5-phenyl-4H-1,3-oxazin-3-yl)-2-methyl-1-(9-phenanthryl)propan-1-one (Compound 448), NMR 1.6 (s,3H), 1.7 (s,6H), 5.4 (s,2H), 6.8 (m,2H), 7.1 (m,2H), 7.5 (m,5H), 7.8 (d,1H), 8.0 (d,1H), 8.1 (s,1H), 8.6 (m,2H); and 1-(3-biphenyl)-2-(2,3-dihydro-6-methyl-4-oxo-5-phenyl-4H-1,3-oxazin-3-yl)-2-methylpropan-1-one (Compound 449), NMR 1.6 (s,6H), (1.7 (s,3H), 5.3 (s,2H), 6.8 (d,2H), 7.1 (m,2H), 7.3 (m,5H), 7.5 (d,2H), 7.6 (d,1H), 7.9 (d,1H), 8.2 (s,1H).

EXAMPLE 15

Lithium bis(trimethylsilyl)amide (1.5 ml of 1.0M solution) was added to a solution of 1-(3,5-difluorophenyl)-2-(2,3-dihydro-6-methyl-4-oxo-5-phenyl-4H-1,3-oxazin-3-yl)-2-methyl-propan-1-one (0.5 g) in tetrahydrofuran, under an inert atmosphere at −5° C. After stirring for 0.5 hours, methyl chloroformate (1.22 g) was added and the solution allowed to warm to 20° C. After 18 hours, the solution was poured onto water, extracted (ether) and evaporated. Purification by dry column chromatography on silica gel, eluting with hexane/ethyl acetate (4:1), gave 1-(3,5-difluorophenyl)-2-(2,3-dihydro-6-methoxycarbonylmethyl-4-oxo-5-phenyl-4H-1,3-oxazin-3-yl)-2-methylpropan-1-one (Compound 700, 0.065 g), NMR 1.5 (s,6H), 3.1 (s,2H), 3.6 (s,3H), 5.4 (s,2H), 6.8 (m,1H), 7.0 (m,2H), 7.2 (m,3H), 7.5 (d,2H).

Further elution gave 1-(3,5-difluorophenyl)-2-[2,3-dihydro-6-bis(methoxycarbonyl)methyl-4-oxo-5-phenyl-4H-1,3-oxazin-3-yl]-2-methylpropan-1-one (Compound 701, 0.066 g), NMR 1.6 (s,6H), 3.8 (s,6H), 4.4 (s,1H), 5.5 (s,2H), 7.0 (m,3H), 7.3 (m,3H), 7.6 (d,2H).

By proceeding in a similar manner, using ethyl chloroformate, the following compounds of formula (I) were prepared:

1-(3,5-difluorophenyl)-2-(2,3-dihydro-6-ethoxycarbonylmethyl-4-oxo-5-phenyl-4H-1,3-oxazin-3-yl)-2-methylpropan-1-one (Compound 702), NMR 1.3 (t,3H), 1.6 (s,6H), 3.2 (s,2H), 4.2 (q,2H), 5.5 (s,2H), 6.9 (m,1H), 7.1 (m,2H), 7.3 (m,3H), 7.5 (d,2H); and 1-(3,5-difluorophenyl)-2-[2,3-dihydro-6-bis(ethoxycarbonyl)methyl-4-oxo-5-phenyl-4H-1,3-oxazin-3-yl]-2-methylpropan-1-one (Compound 703), NMR 1.3

(t,6H), 1.6 (s,6H), 4.2 (q,4H), 4.3 (s,1H), 5.5 (s,2H), 6.9 (m,1H), 7.0 (m,2H), 7.3 (m,3H), 7.5 (d,2H).

EXAMPLE 16

Lithium bis(trimethylsilyl)amide (1.5 ml of 1.0M solution) was added to a solution of 1-(3,5-difluorophenyl)-2-(2,3-dihydro-6-methyl-4-oxo-5-phenyl-4H-1,3-oxazin-3-yl)-2-methylpropan-1-one (0.5 g) in tetrahydrofuran, under inert atmosphere at −5° C. After stirring for 0.5 hours, the solution was poured onto solid carbon dioxide (excess), allowed to warm to ambient temperature and poured onto water. The aqueous phase was acidified, extracted (ethyl acetate), dried (magnesium sulphate) and evaporated, to give 1-(3,5-difluorophenyl)-2-(6-carboxymethyl-2,3-dihydro-4-oxo-5-phenyl-4H-1,3-oxazin-3-yl)-2-methylpropan-1-one (Compound 704, 0.065 g), NMR 1.5 (s,6H), 3.2 (s,2H), 5.4 (s,2H), 6.8 (m,1H), 7.0 (m,2H), 7.2 (m,3H), 7.5 (d,2H), 9.0 (bs,1H).

EXAMPLE 17

A solution of ethyl 4-(2,3-dihydro-6-methyl-4-oxo-5-phenyl-4H-1,3-oxazin-3-yl)-4-methyl-3-oxo-pentanoate (2.0 g), lithium hydride(0.11 g) in 1,2-dimethoxyethane and hexamethylphosphoramide was stirred at 40° C. for 1 hour. cis-1,4-Dichloro-2-butene was then added, and the mixture stirred at 65° C. for 48 hours. The mixture was extracted with ether, washed with brine, dried (magnesium sulphate), evaporated and purified by column chromatography eluting with ethyl acetate/hexane (1:5) to give ethyl 1-[2-(2,3-dihydro-6-methyl-4-oxo-5-phenyl-4H-1,3-oxazin-3-yl)-2-methylpropionyl]cyclopent-3-enylcarboxylate (Compound 9, 0.62 g), NMR: 1.20(3H, t), 1.52(6H, s), 1.91(3H, s), 3.0–3.25(4H, m), 4.14 (2H, q), 5.17(2H, s), 5.56(2H, s), 7.2–7.4(5H, m).

By proceeding in a similar manner the following compounds were prepared:

methyl 1-[2-(2,3-dihydro-6-methyl-4-oxo-5-phenyl-4H-1,3-oxazin-3-yl)-2-methylpropionyl] cyclopentylcarboxylate (Compound 28), NMR:1.45–1.6(8H, m), 1.8–1.9(2H, m), 1.91(3H, s), 2.1–2.2(2H, m), 2.35–2.45(2H, m), 3.69(3H, s), 5.15 (2H, s), 7.2–7.4(5H, m);

benzyl 1-[2-(2,3-dihydro-6-methyl-4-oxo-5-phenyl-4H-1,3-oxazin-3-yl)-2-methylpropionyl] cyclopentylcarboxylate (Compound 44), NMR:1.4–1.55(8H, m), 1.65–1.8(2H, m), 1.90(3H, s), 2.1–2.2(2H, m), 2.4–2. 5(2H, m), 5.14(2H, s), 5.16(2H, s), 7.2–7.4(5H, m); and ethyl 1-[2-(2,3-dihydro-6-ethyl-4-oxo-5-phenyl-4H-1,3-oxazin-3-yl)-2-methylpropionyl]cyclopent-3-enylcarboxylate, NMR:1.101 (3H, t), 1.23(3H, t), 1.52 (6H, s), 2.19(2H, q), 2.98–3.33(4H, m), 4.16(2H, q), 5.19(2H, s), 5.57(2H, s), 7.2–7.4(5H, m) (Compound 1065).

EXAMPLE 18

A solution of 1M diethyl zinc in n-hexane(1.4 ml) was added to a solution of 2-(2,3-dihydro-6-methyl-4-oxo-5-phenyl-4H-1,3-oxazin-3-yl)-2,5-dimethyl-hex-5-en-3-ol (0.40 g) in dichloromethane at 20° C. Diiodomethane (0.13 ml) was then added and the mixture stirred and heated at reflux for 2 hours. Hydrochloric acid (1N) was added and the organic layer washed with brine, dried (magnesium sulphate), and evaporated to give crude 2-(2,3-dihydro-6-methyl-4-oxo-5-phenyl-4H-1,3-oxazin-3-yl)-2-methyl-4-(1-methylcyclopropyl)-butan-3-ol. Powdered molecular sieve 4A (3 g) and pyridinium chlorochromate (0.6 g) were added to a stirred dichloromethane solution of the above compound at 20° C. After 3 hours, ether was added and the mixture filtered, evaporated and purified by silica gel column chromatography, eluting with n-hexane/ethyl acetate (3:1) to give 2-(2,3-dihydro-6-methyl-4-oxo-5-phenyl-4H-1,3-oxazin-3-yl)-2-methyl-4-(1-methylcyclopropyl)butan-3-one (Compound 1066, 0.25 g), NMR: 1.33(4H), 1.08(s, 3H), 1.42(s,6H), 1.92(s,3H), 2.47(s,2H), 5.26(s,2H), 7.20–7.40(5H).

By proceeding in a similar manner the following compounds were prepared:

2-(2,3-dihydro-6-methyl-4-oxo-5-phenyl-4H-1,3-oxazin-3-yl)-2-methyl-4-(2-methylcyclopropyl)pentan-3-one (Compound 1067), NMR:0.20–0.70(4H), 1.03(d,3H), 1.16(d,3H), 1.47(s,3H), 1.54(s,3H), 1.92(s,3H), 5.26 (2H), 7.20–7.40(5H);

1-(bicyclo[3.1.0]hexan-1-yl)-2-(2,3-dihydro-6-methyl-4-oxo-5-phenyl-4H-1,3-oxazin-3-yl)-2-methyl-propan-1-one (Compound 1068), NMR: 0.80(1H), 1.20–1.35 (2H), 1.45(6H), 1.60–1.75(4H), 1.93(s,4H), 1.85–1.95 (1H), 2.28(1H), 5.29(2H), 7.23–7.48(5H);

1-(bicyclo[4.1.0]heptan-2-yl)-2-(2,3-dihydro-6-methyl-4-oxo-5-phenyl-4H-1,3-oxazin-3-yl)-2-methylpropan-1-one (Compound 1070), NMR: 0.30(1H), 0.48(1H), 0.88–1.50(8H), 1.48(s,3H), 1.63(s,3H), 1.92(s,3H), 1.88(1H), 3.41(1H), 5.29(2H), 7.2–7.4(5H); and 2-(2,3-dihydro-6-methyl-4-oxo-5-phenyl-4H-1,3-oxazin-3-yl)-2-methyl-1-(spiro[2.4]heptan-4-yl)propan-1-one (Compound 1071), NMR: 0.25–0.45(2H), 0.56(1H), 0.72(H), 1.42(6H), 1.91(s,3H), 1.6–1.9(3H), 1.95–2.20 (3H), 3.05(1H), 5.22(2H), 7.2–7.4(5H).

EXAMPLE 19

Powdered molecular sieve (4 A, 17 g) and pyridinium chlorochromate (4.3 g) were added to a stirred solution of 2-(2,3-dihydro-6-methyl-4-oxo-5-phenyl-4H-1,3-oxazin-3-yl)-2-methyl-1-(2-methylenecyclopentyl)propan-1-ol (3.1 g) in dichloromethane at 20° C. After 3 hours, ether was added and the mixture filtered, evaporated and the residue purified by silica gel column chromatography eluting with n-hexane/ethyl acetate (3:1) to give 2-(2,3-dihydro-6-methyl-4-oxo-5-phenyl-4H-1,3-oxazin-3-yl)-2-methyl-1-(2-methylenecyclopentyl)propan-1-one (Compound 1072, 1.55 g), NMR: 1.49(s,3H), 1.55(s,3H), 1.93(s,3H), 1.85–2.00(3H) 2.25–2.52(2H), 3.89(1H), 4.87(s,1H), 5.28 (2H), 7.2–7.4(5H).

By proceeding in a similar manner the following compounds were prepared:

2-(2,3-dihydro-6-methyl-4-oxo-5-phenyl-4H-1,3-oxazin-3-yl)-2-methyl-1-(1-methyl-2-methylenecyclopentyl) propan-1-one (Compound 1069); NMR:1.36(s,3H), 1.45(s,3H), 1.47(s,3H), 1.50–1.80(3H), 1.92(s,3H), 2.35–2.70(3H), 4.95(s,1H), 4.99(s,1H), 5.20(d,1H), 5.28(d,1H), 7.23–7.40(5H); and 2-(2,3-dihydro-6-methyl-4-oxo-5-phenyl-4H-1,3-oxazin-3-yl)-2-methyl-1-(5-methyl-2-methylenecyclopentyl) propan-1-one (Compound 1073) 1H NMR: 0.93(d,3H), 1025(1H), 1.53(s,3H), 1.58(s,3H), 1.94(s,3H), 2.12 (1H), 2.25–2.56(3H), 3.47(1H), 4.90(s,1H), 4.98(s, 1H), 5.25(d,1H), 5.32(d,1H), 7.20–7.40(5H).

EXAMPLE 20

A solution of diethyl zinc in n-hexane(1M, 12 ml) was added to a solution of 2-(2,3-dihydro-6-methyl-4-oxo-5- phenyl-4H-1,3-oxazin-3-yl)-2-methyl-hex-5-en-3-ol (1.6 g) in dichloromethane at 20° C. 1,1-Diiodoethane (3.5 g) was added and the solution warmed to 45° C. for 3 hours. Hydrochloric acid (1N) was added and the organic layer washed (brine), dried (magnesium sulphate) and evaporated. Purification by silica gel column chromatography eluting with n-hexane/ethyl acetate (3:1) gave 2-(2,3-dihydro-6-methyl-4-oxo-5-phenyl-4H-1,3-oxazin-3-yl)-2-methyl-4-(2-methylcyclopropyl)butan-3-ol (0.55 g), NMR:1.05–1.75 (4H), 1.01(d,3H), 1.36(s,3H), 1.52(s,3H), 1.4–1.5(2H), 1.89 (s,3H), 3.70(1H), 4.59(1H), 5.10(d,1H), 5.24(d,1H), 7.23–7.40(5H). Powdered molecular sieve (4 A, 3.2 g) and pyridinium chlorochromate (0.8 g) were added to a stirred solution of the above compound in dichloromethane at 20° C. After 3 hours, ether was added and the mixture filtered. The filtrate was evaporated and the residue purified by silica gel column chromatography eluting with n-hexane/ethyl acetate (3:1) to give 2-(2,3-dihydro-6-methyl-4-oxo-5-phenyl-4H-1,3-oxazin-3-yl)-2-methyl-4-(2-methylcyclopropyl)butan-3-one (Compound 1074, 0.47 g), NMR: 0.20–0.30(2H), 0.42–0.52(1H), 0.68–0.78(1H), 1.03 (d,3H), 1.42(s,6H), 1.93(s,3H), 2.43(d,2H), 5.26(s,2H), 7.20–7.40(5H).

EXAMPLE 21

Sodium hydride (60%, 0.06 g) was added to a stirred solution of 2-(2,3-dihydro-4-oxo-6-methyl-5-phenyl-4H-1,3-oxazin-3-yl)-2-methyl-1-(2-methylenecyclopentyl)propan-1-one (0.45 g) at 20° C. After 10 minutes, iodomethane (0.1 ml) was added and stirring continued for 3 hours. Ethyl acetate and water were added and the organic phase dried (magnesium sulphate), evaporated and purified by silica gel column chromatography eluting with n-hexane/ethyl acetate (3:1) to give 2-(2,3-dihydro-6-ethyl-4-oxo-5-phenyl-4H-1,3-oxazin-3-yl)-2-methyl-1-(2-methylenecyclopentyl)propan-1-one (Compound 1075, 0.15 g), NMR: 1.09(t,3H), 1.49(s,3H), 1.55(s,3H), 1.80–2.00 (3H), 2.21(q,2H), 2.25–2.50(3H), 3.89(1H), 4.86(s,1H), 4.98(s,1H), 5.26(d,1H), 5.32(d,1H), 7.20–7.38(5H).

EXAMPLE 22

A solution of ethyl lithium (1.4M) in diethyl ether was added to a stirred solution of 2-(2,3-dihydro-6-methyl-4-oxo-5-phenyl-4H-1,3-oxazin-3-yl)-1-(3-hydroxymethyl-cyclopent-2-enyl)-2-methylpropan-1-ol (0.39 g) in tetrahydrofuran below −60° C. under an argon atmosphere. A solution of p-toluenesulphonyl chloride (0.23 g) in tetrahydrofuran was added below −65° C., followed after 0.5 hour by tetrakis(triphenylphosphine)palladium(0) (0.01 g) in tetrahydrofuran added below −60° C. Finally lithium triethylborohydride (1M) in tetrahydrofuran (1.4 ml) was added below −60° C. The mixture was allowed to slowly warm to 20° C. whilst stirring for 3 hours. Ethyl acetate and water were added and the organic phase washed (brine), dried (magnesium sulphate), evaporated and purified by column chromatography eluting with n-hexane/acetone (2:1) to give a mixture of 2-(2,3-dihydro-6-methyl-4-oxo-5-phenyl-4H-1,3-oxazin-3-yl)-2-methyl-1-(3-methylenecyclopentyl)propan-1-ol and 2-(2,3-dihydro-6-methyl-4-oxo-5-phenyl-4H-1,3-oxazin-3-yl)-2-methyl-1-(3-methylcyclopent-2-en-1-yl)propan-1-ol (0.1 g). To a stirred solution of the above mixture in dichloromethane were added powdered molecular sieve 4A (0.6 g) and pyridinium chlorochromate (0.15 g) at 20° C. After 3 hours, ether was added, the mixture filtered, evaporated and purified by silica gel column chromatography eluting with n-hexane/diethyl ether (2:1) to give 2-(2, 3-dihydro-6-methyl-4-oxo-5-phenyl-4H-1,3-oxazin-3-yl)-2-methyl-1-(3-methylenecyclopentyl)propan-1-one (Compound 1076, 25 mg), NMR: 1.44(s,6H), 1.94(s,3H), 1.85–2.60(6H), 3.32(1H), 4.84(s,1H), 5.27(s,2H), 7.22–7.40 (5H).

EXAMPLE 23

A solution of 4-(2,3-dihydro-6-methyl-4-oxo-5-phenyl-4H-1,3-oxazin-3-yl)-4-methyl-1-penten-3-one (2 g) and cyclopentadiene (1.0 g) in toluene was stirred at reflux temperature for 12 hours, evaporated and the residue purified by silica gel column chromatography eluting with n-hexane/ethyl acetate (5:1) to give 2-(2,3-dihydro-6-methyl-4-oxo-5-phenyl-4H-1,3-oxazin-3-yl)-2-methyl-1-(endo-bicyclo[2.2.1]hept-5-en-2-yl)propan-1-one (Compound 1077, 1.4 g), NMR: 1.25–1.9(m,4H), 1.49(d, 6H), 1.91(s,3H), 2.85(m,1H), 3.1(m,1H) 3.45(m,1H), 5.26 (dd,2H), 5.88(m,1H),6.19(m,1H) and 7.20–7.40(5H); and 2-(2,3-dihydro-6-methyl-4-oxo-5-phenyl-4H-1,3-oxazin-3-yl)-2-methyl-1-(exo-bicyclo[2.2.1]hept-5-en-2-yl)propan-1-one (Compound 1078, 0.54 g), NMR: 1.2–1.9(m,4H), 1.47 (d,6H), 1.9(s,3H), 2.65(m,1H), 2.88(m,2H), 5.25(dd,2H), 6.12(m,2H), 7.2–7.4(m,5H).

EXAMPLE 24

Palladium on carbon (5%, 10 mg) was added a solution of 2-(2,3-dihydro-6-methyl-4-oxo-5-phenyl-4H-1,3-oxazin-3-yl)-2-methyl-1-(endo-bicyclo[2,2,1]hept-5-en-2-yl)propan-1-one (0.2 g ) in ethanol under an atmosphere of argon. The atmosphere was changed to hydrogen and the mixture stirred for 1 hour at 20° C. The mixture was filtered and evaporated to give 2-(2,3-dihydro-6-methyl-4-oxo-5-phenyl-4H-1,3-oxazin-3-yl)-2-methyl-1-(endo-bicyclo[2.2.1]hept-2-yl) propan-1-one (Compound 1079, 150 mg), NMR: 1.1–1.85 (m,8H), 1.45(d,6H), 1.92(s,3H),2.3(m,2H), 2.79(m, 1H), 5.25(dd,2H),7.2–7.45(m,5H).

By proceeding in a similar manner the following compound was prepared:

2-(2,3-dihydro-6-methyl-4-oxo-5-phenyl-4H-1,3-oxazin-3-yl)-2-methyl-1-(exo-bicyclo[2.2.1]hept-2-yl)propan-1-one (Compound 1080), NMR 1.2–1.6(m,8H), 1.42 (d,6H), 1.95(s,3H), 2.2(m,1H), 2.4(m,1H), 3.3(m,1H), 5.25(dd,2H), 7.2–7.35(m,5H).

EXAMPLE 25

Ethanethiol (0.0389 ml) was added to a mixture of 4-(2, 3-dihydro-6-methyl-4-oxo-5-phenyl-4H-1,3-oxazin-3-yl)-4-methylpent-1-en-3-one (100 mg) and potassium carbonate (4.85 mg) in N,N-dimethylformamide, and then stirred overnight at 20° C., and for 24 hours at 40° C. The mixture was purified by silica gel column chromatography eluting with isohexane/ethyl acetate (4:1) to give 5-ethylthio-2-(2, 3-dihydro-6-methyl-4-oxo-5-phenyl-4H-1,3-oxazin-3-yl)-2-methylpentan-3-one (Compound 1083, 45 mg), NMR 1.2(t,3H), 1.4(s,6H), 1.9(s,3H), 2.5(q,2H), 2.8(s,4H), 5.3(s, 2H),7.2–7.4(m,5H).

By proceeding in a similar manner the following compounds were prepared:

5-phenylthio-2-(2,3-dihydro-6-methyl-4-oxo-5-phenyl-4H-1,3-oxazin-3-yl)-2-methylpentan-3-one (Compound 1081), NMR 1.4(s,6H), 1.9(s,3H), 2.8(t, 2H), 3.2(t,2H), 5.2(s,2H), 7.1–7.4(m,10H);

5-(2,2,2-trifluoroethylthio)-2-(2,3-dihydro-6-methyl-4-oxo-5-phenyl-4H-1,3-oxazin-3-yl)-2-methylpentan-3-one (Compound 1084), NMR 1.4(s,6H), 1.9(s,3H), 2.8(t,2H), 2.9(t,2H), 3.1(q,2H), 5.3(s,2H), 7.2–7.4(m, 5H);

5-cyclohexylthio-2-(2,3-dihydro-6-methyl-4-oxo-5-phenyl-4H-1,3-oxazin-3-yl)-2-methylpentan-3-one (Compound 1085), NMR 1.2–1.3(m,5H), 1.4(s,6H), 1.6–1.8(m,4H) 1.9(s,3H), 2.6(M,1H), 2.8(m,4H), 5.2(s, 2H), 7.2–7.4(m,5H);

5-benzylthio-2-(2,3-dihydro-6-methyl-4-oxo-5-phenyl-4H-1,3-oxazin-3-yl)-2-methylpentan-3-one (Compound 1086), NMR 1.4(s,6H), 1.9(s,3H), 2.7(s, 4H), 3.7(s,2H), 5.2(s,2H), 7.2–7.4(m,9H);

5-(2-furylmethyl)thio-2-(2,3-dihydro-6-methyl-4-oxo-5-phenyl-4H-1,3-oxazin-3-yl)-2-methylpentan-3-one (Compound 1087), NMR 1.4(s,6H), 1.9(s,3H), 2.7(m, 4H), 3.7(s,2H), 5.2(s,2H), 6.1–6.3(m,2H) 7.2–7.4(m, 5H);

5-(2-pyridyl)thio-2-(2,3-dihydro-6-methyl-4-oxo-5-phenyl-4H-1,3-oxazin-3-yl)-2-methylpentan-3-one (Compound 1088), NMR 1.4(s,6H), 1.9(s,3H), 3.0(t, 2H), 3.4(t,2H), 5.2(s,2H), 7.0(m,1H), 7.2–30 7.4(m, 5H), 7.4(m,1H), 7.6(m,1H), 8.5(d,1H) and 5-(1-naphthyl)thio-2-(2,3-dihydro-6-methyl-4-oxo-5-phenyl-4H-1,3-oxazin-3-yl)-2-methylpentan-3-one (Compound 1089), NMR 1.4(s,6H), 1.9(s,3H), 2.8(t, 2H), 3.3(t,2H), 5.2(s,2H), 7.2(m,2H), 7.3–7.4(m,4H), 7.5–7.6(m,3H), 7.7(d,1H), 7.8(m,1H), 8.3(d,1H).

EXAMPLE 26

A mixture of 4-(2,3-dihydro-6-methyl-4-oxo-5-phenyl-4H-1,3-oxazin-3-yl)-4-methylpent-1-en-3-one (50 mg), 3-phenoxyaniline (30 mg) and pyridine (0.2 ml) was heated at 40° C. for 1 hour then stirred overnight at 20° C. and at 40° C. for 4 hours. After evaporation the residue was purified by silica gel column chromatography eluting with isohexane/ethyl acetate to give 5-(3-phenoxyphenyl)amino-2-(2,3-dihydro-6-methyl-4-oxo-5-phenyl-4H-1,3-oxazin-3-yl)-2-methylpentan-3-one (Compound 1082, 69 mg), NMR 1.4(s,6H), 1.9(s,3H), 2.8(m,2H), 3.4(m,2H), 5.3(s,2H), 6.3–6.4(m,3H), 6.9–7.4(m,11H).

REFERENCE EXAMPLE 1

A mixture of ethyl 4-(2,3-dihydro-6-methyl-4-oxo-5-phenyl-4H-1,3-oxazin-3-yl)-4-methyl-3-oxo-pentanoate (0.5 g), 1,4-diiodobutane(0.23 ml) and potassium carbonate (1.0 g) was stirred in dimethylsulphoxide at 20° C. for 12 hours. The mixture was diluted (ether), washed (brine), dried (MgSO4), evaporated and the residue purified by column chromatography (ethyl acetate/hexane 1:3) to give ethyl 4-(2,3-dihydro-6-methyl-4-oxo-5-phenyl-4H-1,3-oxazin-3-yl)-2-(4'-iodobutyl)-4-methyl-3-oxo-pentanoate (0.3 g), NMR 1.24(3H, t), 1.3–1.4(2H, m), 1.43((3H, s), 1.48(3H, s), 1.7–2.0(7H, m), 3.12(2H, t), 3.8–3.9(1H, m), 4.1–4.2(2H, m), 5.28(2H, d), 7.2–7.4(5H, m).

REFERENCE EXAMPLE 2

Isopropyl magnesium bromide (0.7M solution in tetrahydrofuran) was added to a solution of mono-ethyl malonate(1.44 g) in tetrahydrofuran at 0° C. The mixture was stirred at 20° C. for 0.5 hour and at 40° C. for 0.5 hour. 2-(2,3-Dihydro-6-methyl-4-oxo-5-phenyl-4H-1,3-oxazin-3-yl)-2-methylpropionic acid (2 g) and carbonyldiimidazole (1.42 g) was stirred in tetrahydrofuran for 8 hours and the resulting imidazolide solution then added to the above mixture at 0° C., stirred at 20° C. for 3 hours and refluxed for 2 hours. The mixture was diluted (ether), washed (5% hydrochloric acid), dried (MgSO4),evaporated and the residue purified by column chromatography (ethyl acetate/hexane 1:2) to give ethyl 4-(2,3-dihydro-6-methyl-4-oxo-5-phenyl-4H-1,3-oxazin-3-yl)-4-methyl-3-oxo-pentanoate (1.4 g), NMR 1.25(3H, t), 1.47(6H, s), 1.94(3H, s), 3.60(2H, s), 4.15(2H, q), 5.26(2H, s), 7.2–7.4(5H, m).

REFERENCE EXAMPLE 3

A solution of ethyl 2-(2,3-dihydro-6-methyl-4-oxo-5-phenyl-4H-1,3-oxazin-3-yl)-2-methylpropanoate (43 g) in tetrahydrofuran was added to lithium aluminium hydride (220 ml of a 1M solution in ether) with stirring at –40° C. After 1 hour the solution was cooled to –70° C., diluted with ether, and treated with brine via dropwise addition, initially at –70° C. and then at –30° C. After warming to room temperature the organic layer was dried (magnesium sulphate), evaporated and the residue purified by dry column chromatography on silica gel eluting with dichloromethane to give 2-(2,3-dihydro-6-methyl-4-oxo-5-phenyl-4H-1,3-oxazin-3-yl)-2-methylpropionaldehyde as a cream solid (22.5 g), NMR 1.35(s,6H), 1.95(s,3H), 5.25(s,2H), 7.22–7.38(m,5H), 9.42(s,1H).

REFERENCE EXAMPLE 4

By proceeding in a similar manner to that of the above Example 8 was prepared 2-(2,3-dihydro-6-methyl-4-oxo-5-phenyl-4H-1,3-oxazin-3-yl)-2-methylhept-6-en-3-one, m.p.90–92° C.

REFERENCE EXAMPLE 5

4-Bromobut-1-ene (approximately 0.2 g) was added to a suspension of magnesium (0.17 g) in tetrahydrofuran, under an inert atmosphere at 20° C. Once the reaction had initiated, further 4-bromobut-1-ene (approximately 0.67 g) in tetrahydrofuran was added over 10 minutes. After refluxing for 1 hour, the mixture was cooled to –5° C. and a solution of 2-(2,3-dihydro-6-methyl-4-oxo-5-phenyl-4H-1,3-oxazin-3-yl)-2-methylpropionaldehyde (1.00 g) in tetrahydrofuran was added over 20 minutes. After stirring for 18 hours, ammonium chloride and ethyl acetate were added and the organic phase washed (brine), dried (magnesium sulphate) and evaporated to give 2-(2,3-dihydro-6-methyl-4-oxo-5-phenyl-4H-1,3-oxazin-3-yl)-2-methylhept-6-en-3-ol (0.68 g) as a white solid, m.p. 74–75° C.

By proceeding in a similar manner the following compounds were also prepared:

2-[4-(2,3-dihydro-6-methyl-4-oxo-5-phenyl-4H-1,3-oxazin-3-yl)-3-hydroxy-4-methylpentyl]-2,5,5-trimethyl-1,3-dioxane; and 2-[4-(2,3-dihydro-6-methyl-4-oxo-5-phenyl-4H-1,3-oxazin-3-yl)-3-hydroxy-4-methylpentyl]-1,3-dioxolane.

REFERENCE EXAMPLE 6

Hydrogen bromide solution in acetic acid (50 g of 30% w/w) was added to 2-(2,3-dihydro-6-methyl-4-oxo-5-phenyl-4H-1,3-oxazin-3-yl)-2-methyl-hept-6-en-3-one (4.14 g) and stirred for 5 hours. Evaporation and dry column chromatography on silica gel eluting with hexane/ethyl acetate (4:1) gave 6-bromo-2-(2,3-dihydro-6-methyl-4-oxo-5-phenyl-4H-1,3-oxazin-3-yl)-2-methyl-heptan-3-one (1.04 g) as a brown gum, NMR 1.4(s,6H), 1.7(d,3H), 1.9(m,1H), 1.9(s,3H), 2.2(m,1H), 2.7(m,2H), 4.1(m,1H), 5.3(s,2H), 7.3 (m,5H).

REFERENCE EXAMPLE 7

4-Bromobiphenyl (0.36 g) was added to a suspension of magnesium (0.056 g) in tetrahydrofuran, under an inert atmosphere at 20° C. After refluxing for 18 hours, the suspension was cooled to −5° C. and a solution of 2-(2,3-dihydro-6-methyl-4-oxo-5-phenyl-4H-1,3-oxazin-3-yl)-2-methylpropionaldehyde (0.20 g) in tetrahydrofuran was added. After stirring for 1 hour, ammonium chloride was added and the organic phase dried (magnesium sulphate) and evaporated. Dry column chromatography on silica gel, eluting with dichloromethane, increasing the polarity to dichloromethane:ethyl acetate (9:1) gave 1-(4-biphenyl)-2-(2,3-dihydro-6-methyl-4-oxo-5-phenyl-4H-1,3-oxazin-3-yl)-2-methylpropan-1-ol (0.11 g), NMR 1.5 (s,3H), 1.7 (s,3H), 1.9 (s,3H), 4.5 (d,1H), 4.8 (m,2H), 5.8 (m,1H), 7.4 (m,9H), 7.6 (m,5H).

By proceeding in a similar manner the following compounds were also prepared:

2-(2,3-dihydro-6-methyl-4-oxo-5-phenyl-4H-1,3-oxazin-3-yl)-2-methyl-1-(3-vinylphenyl)propan-1-ol, NMR 1.4 (s,3H), 1.7 (s,3H), 1.9 (s,3H), 3.7 (m,1H), 4.5 (d,1H), 4.8 (m,2H), 5.2 (d,1H), 5.7 (d,1H), 6.7 (m,2H), 7.3 (m,8H);

1-(2,2-difluoro-1,3-benzodioxol-5-yl)-2-(2,3-dihydro-6-methyl-4-oxo-5-phenyl-4H-1,3-oxazin-3-yl)-2-methylpropan-1-ol, NMR 1.4 (s,3H), 1.6 (s,3H), 1.9 (s,3H), 4.7 (d,1H), 4.8 (d,1H), 4.9 (d,1H), 5.9 (d,1H), 7.3 (m,8H);

2-(2,3-dihydro-6-methyl-4-oxo-5-phenyl-4H-1,3-oxazin-3-yl)-1-(2-fluoro-4-biphenyl)-2-methylpropan-1-ol;

2-(2,3-dihydro-6-methyl-4-oxo-5-phenyl-4H-1,3-oxazin-3-yl)-2-methyl-1-(9-phenanthryl)propan-1-ol, NMR 1.5 (s,3H), 1.7 (s,3H), 1.8 (s,3H), 4.8 (m,3H), 6.1 (s,1H), 7.4 (m,5H), 7.6 (m,4H), 7.9 (d,1H), 8.0 (s,1H), 8.4 (d,1H), 8.7 (d,2H); and 1-(3-biphenyl)-2-(2,3-dihydro-6-methyl-4-oxo-5-phenyl-4H-1,3-oxazin-3-yl)-2-methylpropan-1-ol, NMR 1.5 (s,3H), 1.7 (s,3H), 1.8 (s,3H), 4.4 (d,1H), 4.8 (m,2H), 6.0 (d,1H), 7.2 (m,14H).

REFERENCE EXAMPLE 8

A solution of ethyl 2-(N-methyleneamino)-2-methylpropionate (10.3 g) in xylene was added during 1 hour to a solution of ethyl 2-(2-methoxyphenyl)acetoacetate (8.51 g) in xylene whilst heating under reflux. The rate of addition was controlled so as to equal the rate of azeotropic distillation (via a Dean and Stark separator). Additional xylene was then added and distillation continued for 3 hours. The mixture was evaporated in vacuo to give ethyl 2-[2,3-dihydro-5-(2-methoxyphenyl)-6-methyl-4-oxo-4H-1,3-oxazin-yl]-2-methylpropanoate (14.1 g), NMR 1.25(t,3H), 1.55(s,6H), 1.8(s,3H), 3.75(s,3H), 4.1 5(m,2H), 5.3(s,2H), 6.9–7.3(m,4H).

REFERENCE EXAMPLE 9

A solution of 1-(3,5-difluorophenyl)-2-(2,3-dihydro-6-methyl-4-oxo-5-phenyl-4H-1,3-oxazin-3-yl)-2-methylpropan-1-ol (0.96 g) in dichloromethane was added to a stirred mixture of pyridinium chlorochromate (0.83 g) and powdered molecular sieve (4A) in dichloromethane at 20° C. After 18 hours, ether and charcoal were added, the mixture filtered through hyflo and evaporated to give 1-(3,5-difluorophenyl)-2-(2,3-dihydro-6-methyl-4-oxo-5-phenyl-4H-1,3-oxazin-3-yl)-2-methylpropan-1-one (0.59 g) as a beige solid, m.p. 156.8–157.8° C.

REFERENCE EXAMPLE 10

3,5-Difluorobromobenzene (2.9 g) was added to a suspension of magnesium (0.41 g) in tetrahydrofuran, under an inert atmosphere at 20° C., slowly, to initiate reaction, then at a rate to maintain gentle reflux. After refluxing for 1 hour, the mixture was added to a solution of 2-(2,3-dihydro-6-methyl-4-oxo-5-phenyl-4H-1,3-oxazin-3-yl)-2-methylpropionaldehyde (2.59 g) in tetrahydrofuran at −78° C. The solution was warmed to ambient temperature and stirred for 18 hours. Ammonium chloride and ethyl acetate were added and the organic phase dried (magnesium sulphate) and evaporated to give 1-(3,5-difluorophenyl)-2-methyl-2-(2,3-dihydro-6-methyl-4-oxo-5-phenyl-4H-1,3-oxazin-3-yl)-propan-1-ol (1.32 g), m.p. 87.6–89.0° C.

REFERENCE EXAMPLE 11

A solution of (cyclopent-1-enyl)methylbromide (3.8 g) in tetrahydrofuran was added to a stirred mixture of 2-(2,3-dihydro-6-methyl-4-oxo-5-phenyl-4H-1,3-oxazin-3-yl)-2-methylpropionaldehyde (3.5 g) and zinc powder(1.6 g) in tetrahydrofuran at 20° C. under an inert atmosphere. The temperature increased to 53° C. slowly and after 2 hours, ethyl acetate and hydrochloric acid (1N) were added and the organic phase washed with brine, dried (magnesium sulphate), evaporated and purified by silica gel column chromatography, eluting with n-hexane/ethyl acetate (2:1) to give 2-(2,3-dihydro-6-methyl-4-oxo-5-phenyl-4H-1,3-oxazin-3-yl)-2-methyl-1-(2-methylenecyclopentyl)propan-1-ol (3.66 g), NMR: 1.46(s,3H), 1.61(s,3H), 1.88(s,3H), 1.5–1.9(4H), 2.24(2H), 2.50(1H), 3.24(d,1H), 3.80(s,1H), 4.93(s,1H), 5.06(s,1H), 5.19(d,1H), 5.26(d,1H), 7.22–7.38 (5H).

By proceeding in a similar manner the following compounds were prepared:

2-(2,3-dihydro-6-methyl-4-oxo-5-phenyl-4H-1,3-oxazin-3-yl)-2-methyl-1-(1-methyl-2-methylenecyclopentyl)propan-1-ol; NMR: 1.12(s,3H), 1.52(s,3H), 1.75(s,3H), 1.87(s,3H), 1.45–1.85(3H), 2.10–5.52(d,1H), 7.20–7.40(5H);

2-(2,3-dihydro-6-methyl-4-oxo-5-phenyl-4H-1,3-oxazin-3-yl)-2,5-dimethyl-5-hexen-3-ol; NMR: 1.43(s,3H), 1.56(s,3H), 1.77(s,3H), 1.90(s,3H), 2.45(1H), 2.66 (1H), 3.90(1H), 4.03(1H), 4.82(1H), 5.16(d,1H), 5.28 (d,1H), 7.20–7.40(5H);

2-(2,3-dihydro-6-methyl-4-oxo-5-phenyl-4H-1,3-oxazin-3-yl)-2-methyl-1-(5-methyl-2-methylenecyclopentyl)propan-1-ol; NMR: 0.93(d,3H), 1.28(1H), 1.43(s,3H), 1.62(s,3H), 1.88(s,3H), 1.90–2.35(5H), 3.12(d,1H), 3.83(t,1H), 4.90(s,1H), 5.13(s,1H), 5.20(d,1H), 5.28(d, 1H), 7.20–7.40(5H) and 2-(2,3-dihydro-6-methyl-4-oxo-5-phenyl-4H-1,3-oxazin-3-yl)-2,4-dimethyl-hept-5-en-3-ol; NMR: 1.08(d,3H), 1.41(s,3H), 1.58(s,3H), 1.65(d,3H), 1.88(s,3H), 2.28 (1H), 3.40(d,1H), 4.98(d,1H), 5.15–5.70(4H), 7.20–7.40(5H).

REFERENCE EXAMPLE 12

A solution of 1-bromocyclohex-2-ene (7.2 g) in tetrahydrofuran was added dropwise during 0.5 hour to a stirred mixture of 2-(2,3-dihydro-6-methyl-4-oxo-5-phenyl-4H-1,3-oxazin-3-yl)-2-methylpropionaldehyde (4.0 g) and zinc powder (3.2 g) in tetrahydrofuran below −20° C. under an inert atmosphere. The mixture was stirred for 1 hour below −20° C. and warmed to 20° C. Ethyl acetate and water were added and the organic phase washed (brine), dried (magnesium sulphate), evaporated and purified by silica gel column chromatography, eluting with n-hexane/ethyl acetate (5:2) to give 1-(cyclohex-2-enyl)-2-(2,3-dihydro-6- methyl-4-oxo-5-phenyl-4H-1,3-oxazin-3-yl)-2-methylpropan-1-ol (5.1 g), NMR: 1.41(s,3H), 1.53(s,3H), 1.85(s,3H), 1.40–2.05(6H), 2.24(1H), 3.49(1H), 4.32(d,1H), 5.1 1(d 5.24(d,1H), 5.60(1H), 5.76(1H), 7.20–7.40(5H).

REFERENCE EXAMPLE 13

A part of a solution of 1-bromocyclopent-1-ene (3.9 g) in tetrahydrofuran was added to a stirred mixture of magnesium turnings (0.68 g) and 1 drop of 1,2-dibromoethane in tetrahydrofuran at 20° C. under an inert atmosphere. The mixture was heated to reflux and the remaining bromide solution added dropwise over 15 minutes. The mixture was stirred for 0.5 hour, cooled to 0° C., and a solution of 2-(2,3-dihydro-6-methyl-4-oxo-5-phenyl-4H-1,3-oxazin-3-yl)-2-methylpropionaldehyde (4.0 g) in tetrahydrofuran added below 10° C. The mixture was stirred for 1 hour and ethyl acetate and hydrochloric acid (1N) added. The organic phase was washed (brine), dried (magnesium sulphate), evaporated and purified by silica gel column chromatography, eluting with n-hexane/ethyl acetate (2:1) to give 2-(2,3-dihydro-6-methyl-4-oxo-5-phenyl-4H-1,3-oxazin-3-yl)-2-methyl-1-(cyclopent-1-enyl)propan-1-ol (4.95 g), NMR: 1.45(s,3H), 1.60(s,3H), 1.90(s,3H), 1.80–1.92(2H), 2.15–2.53(4H), 4.37(d,1H), 5.04(d,1H), 5.20–5.30(2H), 5.63(s,1H), 7.22–7.41(5H).

REFERENCE EXAMPLE 14

Osmium tetroxide (3 drops of 5%) in toluene was added to a solution of 1-(cyclohex-2-enyl)-2-(2,3-dihydro-6-methyl-4-oxo-5-phenyl- 4H-1,3-oxazin-3-yl)-2-methylpropan-1-ol (6.9 g) and sodium periodate (6.0 g) in a mixture of tetrahydrofuran and water at 20° C. After stirring for 5 hours, ether was added and the organic phase washed (brine), dried (magnesium sulphate) and evaporated. The residue was dissolved in ether, then sodium hydoxide (20% aqueous solution) added and the mixture stirred for 0.5 hour at 20° C. The organic phase was washed (brine), dried (magnesium sulphate), evaporated and the residue purified by silica gel column chromatography, eluting with n-hexane/ethyl acetate (1:1) to give 2-(2,3-dihydro-6-methyl-4-oxo-5-phenyl-4H-1,3-oxazin-3-yl)-1-(3-formyl-cyclopent-2-enyl)-2-methylpropan-1-ol (0.55 g), NMR: 1.51(s,3H), 1.57 (s,3H), 1.85(1H), 1.93(s,3H), 2.15(1H), 2.40(1H), 2.65(1H), 2.98(1H), 3.53(dd,1H), 5.21(d,1H), 5.35(d,3H), 5.49(d,1H), 6.92(s,1H), 7.25–7.43(5H), 9.74(s,1H).

To a stirred solution of the above compound (0.55 g) in methanol was added sodium borohydride (60 mg) at 20° C. and stirred for 0.5 hour. Ethyl acetate was added and the organic phase washed (brine), dried (magnesium sulphate), evaporated and purified by silica gel column chromatography, eluting with n-hexane/ethyl acetate (1:1) to give 2-(2,3-dihydro-6-methyl-4-oxo-5-phenyl-4H-1,3-oxazin-3-yl)-1-(3-hydroxymethyl-cyclopent-2-enyl)-2-methylpropan-1-ol (0.41 g), NMR: 1.47(s,3H), 1.58(s,3H), 1.80(1H), 1.90s,3H), 2.10(1H), 2.17(s,3H), 2.23(1H), 2.35 (1H), 2.85(s,1H), 3.56(dd,1H), 4.14(s,2H), 4.63(d,1H), 5.17 (d,1H), 5.31(d,1H), 5.53(1H), 7.20–7.40(5H).

According to a further feature of the present invention, there are provided compositions suitable for herbicidal use comprising one or more of the 1,3-oxazin-4-one derivatives of formula I or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, microfine silicon dioxide, talc, chalk, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, glycol ethers, tetrahydrofurfuryl alcohol, acetophenone, cyclohexanone, isophorone, N-alkyl pyrrolidones, toluene, xylene, mineral, animal and vegetable oils, esterified vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of such concentrates to water producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, stabilisers, sequestering agents, anti-caking agents, colouring agents and corrosion inhibitors. These adjuvants may also serve as carriers or diluents.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described.

Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2- dimethyl-3,5-diphenyl-pyrazolium salts], flampropmethyl [methyl N-2-(N-benzoyl-3-chloro-4-fluoroanilino)-propionate], fluometuron [N'-(3-trifluoro-methylphenyl)-N,N-dimethylurea], isoproturon [N'-(4-isopropylphenyl)-N,N-dimethylurea], diclofop {(RS)-2-[4-(2,4-dichlorophenoxy)phenoxy]propionic acid}, fenoxaprop and fenoxaprop-P {2-[4-(6-chloro-1,3-benzoxazol-2-yloxy) phenoxy]propionic acid}, diflufenican{N-(2,4-difluorophenyl)-2-[3-(trifluoromethyl)phenoxy]-3-pyridinecarboxamide}, tralkoxydim {2-[1-(ethoxyimino) propyl]-3-hydroxy-5-mesitylcyclohex-2-enone}, clodinafop {2-[4-(5-chloro-3-fluoro-2-pyridyloxy)phenoxy]propionic acid}, sulcotrione [2-(2-chloro-4-methylsulphonylbenzoyl) cyclohexane-1,3-dione], flurtamone {5-methylamino-2-phenyl-4-[3-(trifluoromethyl)phenyl]-3(2H)-furanone}, aclonifen (2-chloro-6-nitro-3-phenoxyaniline), and sulfonylureas (e.g. nicosulfuron);

insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The following Examples illustrate herbicidal compositions according to the present invention. The following trade marks appear in the description: Ethylan, Soprophor, Sopropon, Rhodorsil, Atagel, Synperonic, Solvesso, Arkopon, Tixosil, Arylan.

EXAMPLE C1

A suspension concentrate is formed from:

| | |
|---|---|
| Oxazinone derivative (Compound 1) | 20% |
| Ethylan BCP (surfactant) | 0.5% |
| Soprophor FL | 0.5% |
| Sopropon T36 (Dispersant) | 0.2% |
| Rhodorsil 426R (Antifoaming agent) | 0.01% |
| Propylene glycol (antifreeze) | 5.0% |
| Atagel 50 (anti-settling agent) | 2.0 |
| Water | to 100% |

Similar suspension concentrates may be prepared by replacing Compound 1 with other oxazinone derivatives of formula I.

EXAMPLE C2

An emulsion concentrate is formed from the following:

| | |
|---|---|
| Oxazinone derivative (Compound 1) | 10% |
| Synperonic NPE1 800 (surfactant) | 4.9% |
| Arylan CA (surfactant) | 5.0% |
| Cyclohexanone (solvent) | 9.8% |
| NMP (solvent) | 9.8% |
| Solvesso 150 (blending agent) | 5.0% |
| Water | to 100% |

Note: NMP means N-methylpyrrolidone

Similar emulsion concentrates may be prepared by replacing Compound 1 with other oxazinone derivatives of formula I.

EXAMPLE C3

A wettable powder is formed from the following:

| | |
|---|---|
| Oxazinone derivative (Compound 1) | 20.0% |
| Arylan SX flake (surfactant) | 3.0% |
| Arkopon T (surfactant) | 5.0% |
| Sodium polycarboxylate (dispersant) | 1.0% |
| Tixosil 38 (flow aid) | 3.0% |
| China Clay | 68.0% |

Similar wettable powders may be prepared by replacing Compound 1 with other oxazinone derivatives of formula I.

According to a feature of the present invention, there is provided a method for controlling the growth of weeds (i.e. undesired vegetation) at a locus which comprises applying to the locus a herbicidally effective amount of at least one 1,3-oxazin-4-one derivative of formula I or an agriculturally acceptable salt thereof. For this purpose, the 1,3-oxazin-4-one derivatives are normally used in the form of herbicidal compositions (i.e. in association with compatible diluents or carriers and/or surface active agents suitable for use in herbicidal compositions), for example as hereinbefore described.

The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis,* and sedges, for example, *Cyperus esculentus.*

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 1 g and 1000 g of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 10 g and 500 g, and preferably between 25 g and 250 g, of active material per hectare are particularly suitable.

The compounds of the invention are especially useful for controlling grass weed species.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non- directional fashion (e.g. by directional or non-directional spraying) to the weeds or to the soil in which they are expected to appear, before or after planting of the trees or plantations at application rates between 50 g and 2000 g, and preferably between 50 g and 1000 g, most preferably between 100 g and 500 g of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 50 g and 2000 g, and preferably between 50 g and 1000 g, most preferably between 100 g and 500 g of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a preemergence control on later-germinating weeds in the soil.

Where especially prolonged weed control is required, the application of the compounds of formula I may be repeated if required.

Method of Use of Herbicidal Compounds

Test Method (A)

Appropriate quantities of the compounds used to treat the plants were dissolved in acetone to give solutions equivalent to application rates of up to 1000 g test compound per hectare (g/ha). These solutions were applied from a standard laboratory herbicide sprayer delivering the equivalent of 290 liters of spray fluid per hectare.

The compounds of the invention were applied to the soil surface, containing the seeds (preemergence evaluation) and the pots properly irrigated.

Visual assessment of crop damage was made 20–24 days after spraying. The results were expressed as the percentage reduction in growth or damage to the crop or weeds, in comparison with the plants in the control pots.

Post-emergence

The plants were grown until they have some leaves.

The compounds used to treat the plants were applied to the plants.

After treatment the pots were properly irrigated. Visual assessment of crop damage and weed control was made 20–24 days after spraying. The results were expressed as the percentage reduction in growth or damage to the crop or weeds, in comparison with the plants in the control pots.

Test Method B

Paddy Post-Emergence Application in Greenhouse

Paddy rice plants (variety; Koshihikari), that had been grown in advance in a greenhouse to a stage of two leaves, were transplanted to each pot. Then in each pot there were sown seeds of *Echinochloa oryzicola, Monochoria vaginalis, Lindernia procumbens* and *Scirpus juncoides* respectively, and water was added.

After having grown the plants in a greenhouse until *Echinochloa oryzicola* reached a stage of 1.5 leaves, solutions were prepared in acetone using compounds described in the Examples so that they contained active ingredients in an amount equivalent to 75, 300 and 1200 g/ha. The solutions were applied to the water by dropping with a pipette.

After 21 days from the application with the chemicals, herbicidal effects on each weed and phytotoxicity on paddy rice plants were visually assessed, and the results expressed as the percentage reduction in growth or damage to the crop or weeds in comparison with the plants in the control pots.

Test Method (C)

Appropriate quantities of the compounds used to treat the plants were dissolved in acetone to give solutions equivalent to application rates of up to 250 g test compound per hectare (g/ha). These solutions were applied from an automatic laboratory herbicide sprayer delivering the equivalent of 720 litres of spray fluid per hectare.

The compounds of the invention were applied to the soil surface, containing the seeds.

After treatment the pots were properly irrigated. Visual assessment of crop damage was made 17 days after spraying. The results were expressed as the percentage reduction in growth or damage to the crop or weeds, in comparison with the plants in the control pots.

When applied at 1000 g/hectare or less pre-emergence in Test Method A, compounds 205, 447, 449, 700 and 704 of the invention gave at least 80% reduction in growth of one or more of the weed species listed above; at levels of applications toxic to the weeds this compound was selective in at least one crop species.

When applied at 1000 g/hectare or less pre-emergence in Test Method A, compound 701 of the invention gave at least 70% reduction in growth of one or more of the weed species listed above; at levels of applications toxic to the weeds this compound was selective in at least one crop species.

When applied at 1200 g/hectare or less, in Test Method B, compounds 1, 9, 28, 44, 193–210, 212, 444, 445, 1065–1072 and 1076–1082 of the invention gave at least 80% reduction in growth of one or more of the weed species listed above.

When applied at 250 g/hectare or less pre- or post-emergence in Test Method C, compounds 1081, 1083–1085 and 1087–1089 of the invention gave at least 70% reduction in growth of one or more of the weed species listed above.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound having the formula (I):

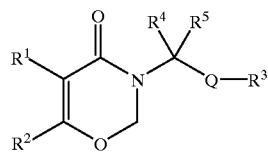

(I)

wherein:

$R^1$ is:

(a) —$CH_2R^6$;

(b) phenyl which is unsubstituted or which has from one to five substituents which are the same or different selected from the group consisting of halogen, hydroxy, lower alkyl, lower haloalkyl, lower alkoxy, lower haloalkoxy, —$S(O)_mR^7$, —$CO_2R^7$, —$COR^7$, cyano, nitro, —$O(CH_2)_nCO_2R^7$, —$OR^6$, —$CH_2OR^7$, —$CH_2S(O)_pR^7$, —$CH_2N(R^7)SO_2R^{7a}$, —$CH_2CN$, —$CH_2P(=O)(OR^7)(OR^{7a})$, —$CH_2P(=O)(OR^7)R^{7a}$, lower alkenyl, lower haloalkenyl, $R^6$, $NR^9R^{10}$ and $NHCOR^7$; or (c) a straight- or branched-chain optionally halogenated alkyl, alkenyl or alkynyl radical having up to ten carbon atoms;

$R^4$ and $R^5$ independently are lower alkyl;

Q is —$C(=O)$— or —$C(OR^{14})(OR^{14a})$— wherein $R^{14}$ and $R^{14a}$ are lower alkyl, or —$C(OR^{14})(OR^{14a})$— is a 1,3-dioxolane or 1,3-dioxane ring having the formula —$C(OR^{14b})(OR^{14c})$— wherein $R^{14b}$ and $R^{14c}$ together are a $C_2$ or $C_3$ alkylene chain which is unsubstituted or substituted by lower alkyl;

$R^6$ is phenyl which is unsubstituted or which has one or more substituents which are the same or different selected from the group consisting of halogen, lower alkyl, lower haloalkyl, lower alkoxy, lower haloalkoxy, —$S(O)_mR^7$, cyano and nitro;

$R^7$ and $R^{7a}$ independently are lower alkyl or lower haloalkyl;

$R^9$ and $R^{10}$ are hydrogen, lower alkyl or lower haloalkyl; and (i):

$R^2$ is:

(a) a hydrogen atom;

(b) a straight- or branched-chain optionally halogenated alkyl, alkenyl or alkynyl radical having up to ten carbon atoms;

(c) a straight- or branched-chain optionally halogenated alkyl radical having from one to six carbon atoms which is substituted by a group $R^{11}$; or (d) a member selected from the group consisting of cyano, —CHO, —$COR^7$, —$CO_2H$, —$CO_2R^7$, —$COSR^7$, —$CONR^9R^{10}$, —CH=NOH, —CH=$NOR^7$, —CH=$NOCOR^7$, —CH=$NNR^9R^{10}$, —$CONHR^6$, —$CONR^6R^7$, —$CO_2R^6$, oxiranyl and $R^{12}$; and $R^3$ is:

(a) cycloalkyl having from three to eight carbon atoms or cycloalkenyl having four to eight carbon atoms, the cycloalkyl or cycloalkenyl ring having a substituent E which is selected from the group consisting of $CO_2H$, $CO_2R^7$, lower alkenyl, lower haloalkenyl, $R^6$, $NR^9R^{10}$, lower alkoxy, lower haloalkoxy, $S(O)_mR^7$, $COR^7$, $COR^6$, $CH_2COR^6$, $COCH_2R^6$, $CO_2CH_2R^6$, $S(O)_qR^6$, CN, $S(O)_qCH_2R^6$, $S(O)_rR^{15}$, $CH_2OR^7$, CHO, $COR^{12}$, $NO_2$, $CONHR^6$, $CONR^6R^7$, $CH_2OH$, —$CH(OR^{14})(OR^{14a})$ wherein —$CH(OR^{14})(OR^{14a})$ optionally represents a five or six membered cyclic acetal which is unsubstituted or which is substituted by one or more $R^7$, or one of the cycloalkyl carbon atoms forms part of a carbonyl group, or the cycloalkyl or cycloalkenyl ring in addition to E has one or more halogen or $R^7$ substituents;

(b) cycloalkyl having from five to seven carbon atoms or cycloalkenyl having five or six carbon atoms, the cycloalkyl or cycloalkenyl ring being unsubstituted or substituted by one or more $R^{13}$, the cycloalkyl or cycloalkenyl ring being fused to a phenyl ring which is unsubstituted or which has from one to four substituents which are the same or different selected from the group consisting of halogen, lower alkyl, lower haloalkyl, lower alkoxy, lower haloalkoxy, —S(O)$_m$R$^7$, cyano and nitro, the cycloalkyl or cycloalkenyl ring of the fused system being linked to the group Q;

(c) a bicyclo-alkane, a bicyclo-alkene, a spiro-alkane or a spiro-alkene, the ring systems of each of which contain from six to nine carbon atoms and are unsubstituted or are substituted by one or more lower alkyl radicals; or (d) cycloalkyl having from three to eight carbon atoms substituted by an exocyclic optionally halogenated alkylidene radical having from one to six carbon atoms, the cycloalkyl ring being optionally further substituted by one or more lower alkyl radicals, provided that when the alkylidene radical is methylidene, then both vacant positions of the exocyclic carbon atom are optionally linked by an alkylene chain which together with the methylidene carbon atom forms a three to six membered cycloalkyl ring;

or (ii):

$R^2$ is lower alkyl or lower haloalkyl, each of which is substituted by one or two $R^{11a}$; or $R^2$ is $R^{12}$, —CONHR$^6$, —CONR$^6$R$^7$ or CO$_2$R$^6$;

and $R^3$ is cycloalkyl having from three to six carbon atoms or cycloalkenyl having five or six carbon atoms, which is unsubstituted or is substituted by an $R^7$ or one or more halogen atoms which are the same or different;

$R^{11}$ is —OH, —OR$^7$, —OCOR$^7$, —S(O)$_m$R$^7$, —NR$^9$R$^{10}$, azide, —CONR$^9$R$^{10}$, —CONHR$^6$, —CONR$^6$R$^7$, —OR$^6$, —OSO$_2$R$^7$, —OSO$_2$R$^6$, —OCOR$^6$, —OCH$_2$COR$^6$, —S(O)$_q$R$^6$, R$^6$, R$^{12}$, —P(=O)(OR$^7$)(OR$^{7a}$), —P(=O)(OR$^7$)R$^{7a}$, —CO$_2$H, —CO$_2$R$^7$, —CO$_2$R$^6$, CN, NO$_2$, CHO, COR$^7$, COSR$^7$, —S(O)$_r$R$^{15}$ or —CO$_2$R$^{15}$;

$R^{11a}$ is —CONR$^9$R$^{10}$, —CONHR$^6$, —CONR$^6$R$^7$, —OR$^6$, —OSO$_2$R$^7$, —OSO$_2$R$^6$, —OCOR$^6$, —OCH$_2$COR$^6$, —S(O)$_q$R$^6$, R$^6$, R$^{12}$, —P(=O)(OR$^7$)(OR$^{7a}$), —P(=O)(OR$^7$)R$^{7a}$, —CO$_2$H, —CO$_2$R$^7$, —CO$_2$R$^6$, CHO, COR$^7$, COR$^6$, COSR$^7$, —S(O)$_r$R$^{15}$ or —CO$_2$R$^{15}$;

$R^{12}$ is cycloalkyl having from three to seven carbon atoms or cycloalkenyl having five or six carbon atoms, which is unsubstituted or is substituted by one or more $R^{13}$;

$R^{13}$ is halogen, lower alkyl or lower haloalkyl;

$R^{15}$ is cycloalkyl having from three to seven carbon atoms which is unsubstituted or substituted by one or more $R^{13}$;

m, p, q, r and t each represent zero, one or two; and n represents one or two;

or an agriculturally acceptable salt thereof.

2. A compound according to claim 1, wherein $R^1$ is phenyl, unsubstituted or substituted by one or more members selected from the group consisting of halogen, lower alkyl and lower haloalkyl.

3. A compound according to claim 2, wherein $R^1$ is unsubstituted phenyl.

4. A compound according to claim 1, wherein $R^2$ is a straight- or branched-chain optionally halogenated alkyl radical having from one to six carbon atoms.

5. A compound according to claim 4, wherein $R^2$ is methyl.

6. A compound according to claim 1, wherein each of $R^4$ and $R^5$ is methyl.

7. A compound according to claim 1, wherein Q is —C(=O)—.

8. A compound according to claim 1, wherein $R^3$ is substituted cyclopentyl.

9. A compound according to claim 1, wherein $R^3$ is bicyclo[2.2.1]heptane, bicyclo[2.2.1]heptene, bicyclo[3.1.0]hexane, bicyclo[4.1.0]heptane, spiro[2.4]heptane, spiro[2.4]heptene; or cycloalkyl having from three to six carbon atoms substituted by an exocyclic alkylidene radical which has from one to six carbon atoms.

10. A compound according to claim 1 having the general formula (Ie):

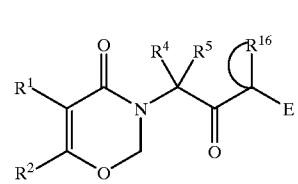

(Ie)

wherein:

$R^1$, $R^2$, $R^4$ and $R^5$ and E are as defined in claim 1; and $R^{16}$ is C$_2$–C$_7$ alkylene or C$_3$–C$_7$ alkenylene, each of which is unsubstituted or substituted by one or more halogen or $R^7$.

11. A compound according to claim 10, wherein:

$R^1$ is phenyl, which is unsubstituted or substituted by halogen or methyl;

$R^2$ is methyl or fluoromethyl; and each of $R^4$ and $R^5$ is methyl.

12. A compound according to claim 10, wherein:

$R^1$ is phenyl, which is unsubstituted or substituted by halogen or methyl;

$R^2$ is methyl or fluoromethyl;

E is —CO$_2$R$^7$, —CH$_2$COR$^6$, —CN, —S(O)$_q$R$^6$, —S(O)$_m$R$^7$, —COR$^7$, —NO$_2$ or —CO$_2$CH$_2$R$^6$;

each of $R^4$ and $R^5$ is methyl; and $R^{16}$ is C$_2$–C$_7$ alkylene, C$_3$–C$_7$ alkenylene, or indanyl, each of which is unsubstituted or substituted by one or more halogen or $R^7$.

13. A compound according to claim 1, wherein $R^3$ is cycloalkyl having from three to six carbon atoms or cycloalkenyl having five or six carbon atoms, the ring systems of which are unsubstituted or substituted by an $R^7$ or one or more halogen atoms which are the same or different.

14. A compound according to claim 1, wherein:

$R^1$ is phenyl;

each of $R^2$, $R^4$ and $R^5$ is methyl;

Q is —C(=O)—; and $R^3$ is bicyclo[2.2.1]heptane, bicyclo[2.2.1]heptene, bicyclo[3.1.0]hexane, bicyclo[4.1.0]heptane, spiro[2.4]heptane, spiro[2.4]heptene, or cycloalkyl having from three to six carbon atoms substituted by an exocyclic methylene group and optionally being substituted by one or more lower alkyl.

15. The compound according to claim 1, which is:

ethyl 1-[2-(2,3-dihydro-6-methyl-4-oxo-5-phenyl-4H-1,3-oxazin-3-yl)-2-methylpropionyl]cyclopentylcarboxylate;

ethyl 1-[2-(2,3-dihydro-6-methyl-4-oxo-5-phenyl-4H-1,3-oxazin-3-yl)-2-methylpropionyl]cyclopent-3-enylcarboxylate;

methyl 1-[2-(2,3-dihydro-6-methyl-4-oxo-5-phenyl-4H-1,3-oxazin-3-yl)-2-methylpropionyl]cyclopentylcarboxylate;

benzyl 1-[2-(2,3-dihydro-6-methyl-4-oxo-5-phenyl-4H-1,3-oxazin-3-yl)-2-methylpropionyl]cyclopentylcarboxylate;

ethyl 1-[2-(2,3-dihydro-6-ethyl-4-oxo-5-phenyl-4H-1,3-oxazin-3-yl)-2-methylpropionyl]cyclopent-3-enylcarboxylate;

1-(bicyclo[3.1.0]hexan-1-yl)-2-(2,3-dihydro-6-methyl-4-oxo-5-phenyl-4H-1,3-oxazin-3-yl)-2-methyl-propan-1-one;

1-(bicyclo[4.1.0]heptan-2-yl)-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2-methyl-1-(spiro[2.4]heptan-4-yl)propan-1-one;

2-(2,3-dihydro-6-methyl-4-oxo-5-phenyl-4H-1,3-oxazin-3-yl)-2-methyl-1-(endo-bicyclo[2.2.1]hept-5-en-2-yl)propan-1-one;

2-(2,3-dihydro-6-methyl-4-oxo-5-phenyl-4H-1,3-oxazin-3-yl)-2-methyl-1-(exo-bicyclo[2.2.1]hept-5-en-2-yl)propan-1-one;

2-(2,3-dihydro-6-methyl-4-oxo-5-phenyl-4H-1,3-oxazin-3-yl)-2-methyl-1-(endo-bicyclo[2.2.1]hept-2-yl)propan-1-one; or 2-(2,3-dihydro-6-methyl-4-oxo-5-phenyl-4H-1,3-oxazin-3-yl)-2-methyl-1-(exo-bicyclo[2.2.1]hept-2-yl)propan-1-one.

16. A herbicidal composition comprising a herbicidally effective amount of a compound of formula (I) as claimed in claim 1, or an agriculturally acceptable salt thereof, and at least one member selected from the group consisting of an agriculturally acceptable diluent or carrier and a surface-active agent.

17. A method for the control of weeds at a locus which comprises applying to said locus a herbicidally effective amount of a compound of formula (I) as claimed in claim 1, or an agriculturally acceptable salt thereof.

18. A method for the control of weeds at a locus which comprises applying to said locus a herbicidally effective amount of a composition as claimed in claim 16.

19. A method according to claim 17, wherein the locus is an area used, or to be used, for the growing of crops and the compound of formula (I) is applied at an application rate of from about 0.001 to about 1.0 kg/ha.

20. A process for the preparation of a compound of formula (I) as defined in claim 1, which comprises:

(a) when Q in formula (I) is —C(═O)—, oxidizing the corresponding compound of formula (I) wherein Q is —CH(OH)—;

(b) when the compound of formula (I) has the formula (Ie):

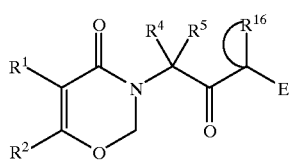

(Ie)

wherein $R^1$, $R^2$, $R^4$ and $R^5$ and E are as defined in claim 1 and $R^{16}$ is $C_2$–$C_7$ alkylene or $C_3$–$C_7$ alkenylene, each of which is unsubstituted or substituted by one or more halogen or $R^7$, reacting a compound of formula (III):

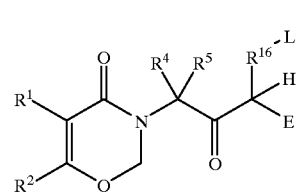

(III)

wherein L is a leaving group, $R^{16}$ is as defined above and the other symbols are as defined in claim 1, with a base;

(c) when the compound of formula (I) has formula (Ie) above, wherein $R^1$, $R^2$, $R^4$ and $R^5$ are as defined in claim 1, $R^{16}$ is $C_2$–$C_7$ alkylene or $C_3$–$C_7$ alkenylene, each of which is substituted by one or more halogen or $R^7$ and E is replaced by a hydrogen atom, subjecting to hydrolysis or hydrogenolysis and decarboxylation the corresponding compound wherein E is $CO_2R^7$ or $CO_2CH_2R^6$;

(d) when Q in formula (I) is —C(═O)—, reacting a compound of formula (IV):

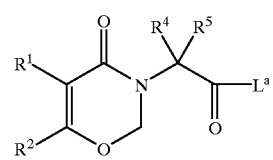

(IV)

wherein $L^a$ is a leaving group, with an organometallic reagent of formula (V):

$$R^3—M \qquad (V)$$

wherein $R^3$ is as defined in claim 1 and M is a metal or metal halide;

(e) when $R^2$ in formula (I) is lower alkyl or lower haloalkyl substituted by CHO, $COR^7$ or $COR^6$, oxidizing the corresponding compound of formula (I) wherein $R^{11a}$ is replaced by $CH_2OH$, $CH(OH)R^7$ or $CH(OH)R^6$;

(f) when $R^2$ in formula (I) is lower alkyl or lower haloalkyl substituted by $SR^6$ or $SR^{15}$ wherein $R^6$ and $R^{15}$ are as defined in claim 1, reacting the corresponding compound of formula (I) wherein $R^{11a}$ is replaced by a leaving group, with a thiol of formula $R^6SH$ or $R^{15}SH$ or an alkali metal salt thereof;

(g) when $R^2$ in formula (I) is lower alkyl or lower haloalkyl substituted by $OC(O)R^6$, wherein $R^6$ is as defined in claim 1, reacting the corresponding compound of formula (I) wherein the $OC(O)R^6$ group is replaced by a leaving group, with a salt of formula $R^6—CO_2—M_1^+$, wherein $M_1$ is sodium or potassium;

(h) when $R^2$ in formula (I) is lower alkyl or lower haloalkyl substituted by $R^{11a}$ wherein $R^{11a}$ is $CO_2R^7$, $CO_2R^{15}$ or $CO_2R^6$, esterifying the corresponding compound of formula (I) wherein $R^{11a}$ is $CO_2H$, or chlorinating the corresponding compound of formula (I) wherein $R^{11a}$ is $CO_2H$ to give the corresponding acid chloride, followed by reacting with an alcohol of formula $R^7OH$ or $R^{15}OH$ or phenol $R^6OH$;

(i) when $R^2$ in formula (I) is lower alkyl or lower haloalkyl substituted by $R^{11a}$ wherein $R^{11a}$ is $CONR^9R^{10}$, $CONHR^6$ or $CONR^6R^7$ wherein $R^6$, $R^7$, $R^9$ and $R^{10}$ are as defined in claim 1, reacting the corresponding compound of formula (I) in which $R^{11a}$ is $CO_2H$ with a chlorinating agent to produce the carboxylic acid chloride, followed by reacting with an amine of formula $R^9R^{10}NH$, $R^6NH_2$ or $R^6R^7NH$, wherein $R^6$, $R^7$, $R^9$ and $R^{10}$ are as defined in claim 1;

(j) when $R^2$ in formula (I) is lower alkyl or lower haloalkyl substituted by $R^{11a}$ wherein $R^{11a}$ is $CO_2H$, oxidizing the corresponding compound of formula (I) in which $R^2$ is CHO;

(k) when $R^2$ in formula (I) is lower alkyl or lower haloalkyl substituted by $R^{11a}$ wherein $R^{11a}$ is $OSO_2R^6$ or $OSO_2R^7$, reacting the corresponding compound of formula (I) wherein $R^{11a}$ is replaced by hydroxy with a sulphonating agent of formula $R^6SO_2Y$ or $R^7SO_2Y$ wherein Y is a leaving group;

(l) when $R^2$ in formula (I) is lower alkyl or lower haloalkyl substituted by $R^{11a}$ wherein $R^{11a}$ is $OR^6$, reacting the corresponding compound of formula (I) wherein $R^{11a}$ is replaced by a leaving group, with a phenol $R^6OH$ and a base;

(m) when R in formula (I) is lower alkyl or lower haloalkyl substituted by $R^{11a}$ wherein $R^{11a}$ is $OCH_2COR^6$, reacting the corresponding compound of formula (I) wherein $R^{11a}$ is replaced by hydroxy, with a halide of formula $R^6COCH_2Z$ wherein Z is chloro or bromo;

(n) when $R^2$ in formula (I) is $CH_2CO^2H$, reacting the corresponding compound of formula (I) wherein $R^2$ is replaced by methyl, with a strong base, followed by addition of carbon dioxide;

(o) when $R^2$ in formula (I) is $CH_2CO_2R^7$, $CH_2CO_2R^6$ or $CH_2CO_2R^{15}$, or a bis-substituted product in which $R^2$ is $CH(CO_2R^7)_2$, $CH(CO_2R^6)_2$ or $CH(CO_2R^{15})_2$, reacting the corresponding compound of formula (I) wherein $R^2$ is replaced by methyl, with a strong base, followed by a chloroformate of formula $ClCO_2R^7$, $ClCO_2R^6$ or $ClCO_2R^{15}$;

(p) when $R^3$ in formula (I) is a bicycloalkene, subjecting to the Diels Alder reaction the corresponding compound wherein $R^3$ is vinyl with a cycloalkadiene;

(q) when $R^3$ in formula (I) is a bicycloalkane, reducing the corresponding compound wherein $R^3$ is a bicycloalkene;

(r) when $R^3$ in formula (I) is cycloalkyl having from three to eight carbon atoms substituted by an exocyclic optionally halogenated alkylidene group; or a bicycloalkane, bicyclo-alkene, spiro-alkane or spiro-alkene, reacting the corresponding alkene, alkylidene or cycloalkene compound with a dihaloalkane and an organometallic reagent;

(s) when Q in formula (I) is $-C(OR^{14})(OR^{14a})-$, reacting a compound of formula (I) wherein Q is $-C(=O)-$ with an alcohol of formula $R^{14}-OH$ or a diol of formula $HO-R^{14e}-OH$ wherein $R^{14e}$ is a $C_2$ or $C_3$ alkylene chain optionally substituted by one or more lower alkyl radicals; or (t) when m, p, q, r or t in formula (I) is one or two, oxidizing the sulphur atom of the corresponding compound of formula (I) wherein m, p, q, r or t is zero or one;

optionally followed by converting the compound of formula (I) thus obtained into an agriculturally acceptable salt thereof.

21. A compound having the formula (I):

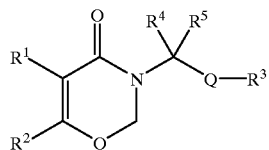

(I)

wherein:

$R^1$ is phenyl which is unsubstituted or which has from one to five substituents which are the same or different selected from the group consisting of halogen, hydroxy, lower alkyl, lower haloalkyl, lower alkoxy, lower haloalkoxy, $-S(O)_mR^7$, $-CO_2R^7$, $-COR^7$, cyano, nitro, $-O(CH_2)_nCO_2R^7$, $-OR^6$, $-CH_2OR^7$, $-CH_2S(O)_pR^7$, $-CH_2N(R^7)SO_2R^{7a}$, $-CH_2CN$, $-CH_2P(=O)(OR^7)(OR^{7a})$, $-CH_2P(=O)(OR^7)R^{7a}$, lower alkenyl, lower haloalkenyl, $R^6$, $NR^9R^{10}$ and $NHCOR^7$;

$R^4$ and $R^5$ independently are lower alkyl;

Q is $-C(=O)-$;

$R^6$ is phenyl which is unsubstituted or which has one or more substituents which are the same or different selected from the group consisting of halogen, lower alkyl, lower haloalkyl, lower alkoxy, lower haloalkoxy, $-S(O)_mR^7$, cyano and nitro;

$R^7$ and $R^{7a}$ independently are lower alkyl or lower haloalkyl;

$R^9$ and $R^{10}$ are hydrogen, lower alkyl or lower haloalkyl;

$R^2$ is a straight- or branched-chain optionally halogenated alkyl, alkenyl or alkynyl radical having up to ten carbon atoms;

$R^3$ is cycloalkyl having from three to eight carbon atoms or cycloalkenyl having four to eight carbon atoms, the cycloalkyl or cycloalkenyl ring having a substituent E which is selected from the group consisting of $CO_2H$, $CO_2R^7$, lower alkenyl, lower haloalkenyl, $R^6$, $NR^9R^{10}$, lower alkoxy, lower haloalkoxy, $S(O)_mR^7$, $COR^7$, $COR^6$, $CH_2COR^6$, $COCH_2R^6$, $CO_2CH_2R^6$, $S(O)_qR^6$, CN, $S(O)_qCH_2R^6$, $S(O)_rR^{15}$, $CH_2OR^7$, CHO, $COR^{12}$, $NO_2$, $CONHR^6$, $CONR^6R^7$, $CH_2OH$, or one of the cycloalkyl carbon atoms forms part of a carbonyl group, or the cycloalkyl or cycloalkenyl ring in addition to E has one or more halogen or $R^7$ substituents;

$R^{12}$ is cycloalkyl having from three to seven carbon atoms or cycloalkenyl having five or six carbon atoms, which is unsubstituted or is substituted by one or more $R^{13}$;

$R^{13}$ is halogen, lower alkyl or lower haloalkyl;

$R^{15}$ is cycloalkyl having from three to seven carbon atoms which is unsubstituted or substituted by one or more $R^{13}$;

m, p, q, and r each represent zero, one or two; and n represents one or two;

or an agriculturally acceptable salt thereof.

22. A compound according to claim 21, wherein $R^1$ is phenyl.

23. A compound according to claim 21, wherein $R^2$ is methyl.

24. A compound according to claim 21, wherein each of $R^4$ and $R^5$ is methyl.

25. A compound according to claim 21, wherein $R^3$ is substituted cyclopentyl.

26. The compound according to claim 21, which is:

ethyl 1-[2-(2,3-dihydro-6-methyl-4-oxo-5-phenyl-4H-1,3-oxazin-3-yl)-2-methylpropionyl]cyclopentylcarboxylate;

ethyl 1-[2-(2,3-dihydro-6-methyl-4-oxo-5-phenyl-4H-1,3-oxazin-3-yl)-2-methylpropionyl]cyclopent-3-enylcarboxylate;

methyl 1-[2-(2,3-dihydro-6-methyl-4-oxo-5-phenyl-4H-1,3-oxazin-3-yl)-2-methylpropionyl]cyclopentylcarboxylate; or benzyl 1-[2-(2,3-dihydro-6-methyl-4-oxo-5-phenyl-4H-1,3-oxazin-3-yl)-2-methylpropionyl]cyclopentylcarboxylate.

27. A herbicidal composition comprising a herbicidally effective amount of a compound of formula (I) as claimed in claim 21, or an agriculturally acceptable salt thereof, and at least one member selected from the group consisting of an agriculturally acceptable diluent or carrier and a surface-active agent.

28. A method for the control of weeds at a locus which comprises applying to said locus a herbicidally effective amount of a compound of formula (I) as claimed in claim 21, or an agriculturally acceptable salt thereof.

29. A method for the control of weeds at a locus which comprises applying to said locus a herbicidally effective amount of a composition as claimed in claim 27.

30. A method according to claim 28, wherein the locus is an area used, or to be used, for the growing of crops and the compound of formula (I) is applied at an application rate of from about 0.001 to about 1.0 kg/ha.

31. A process for the preparation of a compound of formula (I) as defined in claim 21, which comprises:

(a) oxidizing a compound corresponding to formula (I) but wherein Q is —CH(OH)—;

(b) when the compound of formula (I) has the formula (Ie):

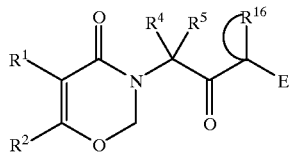

(Ie)

wherein $R^1$, $R^2$, $R^4$ and $R^5$ and E are as defined in claim 21 and $R^{16}$ is $C_2$–$C_7$ alkylene or $C_3$–$C_7$ alkenylene, each of which is unsubstituted or substituted by one or more halogen or $R^7$, reacting a compound of formula (III):

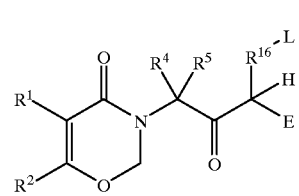

(III)

wherein L is a leaving group, $R^{16}$ is as defined above and the other symbols are as defined in claim 21, with a base;

(c) reacting a compound of formula (IV):

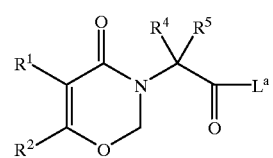

(IV)

wherein $L^a$ is a leaving group, with an organometallic reagent of formula (V):

$$R^3—M \qquad (V)$$

wherein $R^3$ is as defined in claim 21 and M is a metal or metal halide; or (d) when m, p, q or r in formula (I) is one or two, oxidizing the sulphur atom of the corresponding compound of formula (I) wherein m, p, q or r is zero or one;

optionally followed by converting the compound of formula (I) thus obtained into an agriculturally acceptable salt thereof.

* * * * *